(12) United States Patent
Rice et al.

(10) Patent No.: US 11,149,047 B2
(45) Date of Patent: Oct. 19, 2021

(54) ARYL IMIDAZOLES FOR TREATMENT OF CANCER

(71) Applicant: Aptose Biosciences Inc., Mississauga (CA)

(72) Inventors: William G. Rice, Del Mar, CA (US); Stephen H. Howell, La Jolla, CA (US); Cheng-Yu Tsai, La Jolla, CA (US)

(73) Assignee: Aptose Biosciences, Inc., Mississauga (CA)

( * ) Notice: Subject to any disclaimer, the term of this patent is extended or adjusted under 35 U.S.C. 154(b) by 0 days.

(21) Appl. No.: 16/174,938

(22) Filed: Oct. 30, 2018

(65) Prior Publication Data

US 2019/0169215 A1    Jun. 6, 2019

Related U.S. Application Data

(60) Provisional application No. 62/578,938, filed on Oct. 30, 2017.

(51) Int. Cl.
    *A61K 31/44*      (2006.01)
    *A61K 31/53*      (2006.01)
    (Continued)

(52) U.S. Cl.
    CPC ........ *C07F 15/025* (2013.01); *A61K 31/4745* (2013.01); *A61K 31/517* (2013.01);
    (Continued)

(58) Field of Classification Search
    CPC .......................... A61K 31/4745; A61K 31/555
    (Continued)

(56) References Cited

U.S. PATENT DOCUMENTS 3,279,918 A    10/1966   Cassiers
3,297,710 A    1/1967   Silversmith
(Continued)

FOREIGN PATENT DOCUMENTS

CA    1195325    10/1985
CA    2351694    7/1993
(Continued)

OTHER PUBLICATIONS

Kreige et al. "Sensitivity to First-Line Chemotherapy for Metastatic Breast Cancer in BRCA1 and BRCA2 Mutation Carriers", J Clin Oncol, 2009, vol. 27, No. 23, pp. 3764-3771. (Year: 2009).*
(Continued)

*Primary Examiner* — Shengjun Wang
(74) *Attorney, Agent, or Firm* — Cooley LLP

(57) ABSTRACT

The present invention relates to a method of preventing, reducing, or treating cancer in a subject, comprising administering a therapeutically effective amount of (Continued)

or a pharmaceutically acceptable salt, free base, hydrate, complex, or chelate (including metal chelates, such as iron, zinc and others) thereof to the subject, wherein the subject has a mutation in a DNA repair gene.

23 Claims, 35 Drawing Sheets

Specification includes a Sequence Listing.

(51) Int. Cl.

| | | |
|---|---|---|
| C07F 15/02 | (2006.01) | |
| C07D 471/14 | (2006.01) | |
| A61K 31/517 | (2006.01) | |
| A61P 35/00 | (2006.01) | |
| A61K 31/555 | (2006.01) | |
| A61K 31/4745 | (2006.01) | |
| A61K 45/06 | (2006.01) | |

(52) U.S. Cl.
CPC ............ *A61K 31/555* (2013.01); *A61K 45/06* (2013.01); *A61P 35/00* (2018.01); *C07D 471/14* (2013.01)

(58) Field of Classification Search
USPC ........................................................ 514/287
See application file for complete search history.

(56) References Cited

U.S. PATENT DOCUMENTS

| | | |
|---|---|---|
| 3,714,181 A | 1/1973 | Lantos |
| 4,089,747 A | 5/1978 | Bruschi |
| 4,423,046 A | 12/1983 | Carlson |
| 4,466,976 A | 8/1984 | Klose et al. |
| 4,585,771 A | 4/1986 | Klose et al. |
| 4,705,855 A | 11/1987 | Desideri et al. |
| 4,720,459 A | 1/1988 | Winkelhake |
| 4,721,670 A | 1/1988 | Osada et al. |
| 4,758,421 A | 7/1988 | Chang et al. |
| 4,762,706 A | 8/1988 | McCormick et al. |
| 4,902,705 A | 2/1990 | Hirota et al. |
| 4,970,226 A | 11/1990 | Sun |
| 5,011,472 A | 4/1991 | Aebischer |
| 5,023,252 A | 6/1991 | Hsieh |
| 5,024,935 A | 6/1991 | McClune |
| 5,047,318 A | 9/1991 | Snyder |
| 5,081,230 A | 1/1992 | Carney |
| 5,161,389 A | 11/1992 | Rockenfeller et al. |
| 5,300,631 A | 4/1994 | Weinberg et al. |
| 5,328,671 A | 7/1994 | Rockenfeller et al. |
| 5,441,716 A | 8/1995 | Rockenfeller et al. |
| 5,443,956 A | 8/1995 | Carney |
| 5,496,702 A | 3/1996 | Bishop |
| 5,501,959 A | 3/1996 | Lancaster et al. |
| 5,514,550 A | 5/1996 | Findlay |
| 5,656,644 A | 8/1997 | Adams |
| 5,686,455 A | 11/1997 | Adams |
| 5,693,589 A | 12/1997 | Goswami |
| 5,700,826 A | 12/1997 | Mjalli et al. |
| 5,753,687 A | 5/1998 | Mjalli |
| 5,809,775 A | 9/1998 | Tarabulski et al. |
| 5,916,891 A | 6/1999 | Adams |
| 5,945,418 A | 8/1999 | Bemis |
| 6,060,216 A | 5/2000 | Ichikawa |
| 6,117,609 A | 9/2000 | Maeda |
| 6,194,441 B1 | 2/2001 | Roberts |
| 6,266,955 B1 | 7/2001 | Liang et al. |
| 6,268,370 B1 | 7/2001 | Adams |
| 6,288,212 B1 | 9/2001 | Hancock |
| 6,521,655 B1 | 2/2003 | Beers |
| 6,589,966 B1 | 7/2003 | Torti et al. |
| 6,852,727 B2 | 2/2005 | Goulet et al. |
| 7,115,645 B2 | 10/2006 | Halfbrodt et al. |
| 7,291,404 B2 | 11/2007 | Aziz et al. |
| 7,364,868 B2 | 4/2008 | Ruppert et al. |
| 7,479,376 B2 | 1/2009 | Waldman et al. |
| 7,695,926 B2 | 4/2010 | Perez et al. |
| 7,718,685 B2 | 5/2010 | Shin et al. |
| 7,785,817 B2 | 8/2010 | Waldman et al. |
| 7,799,528 B2 | 9/2010 | Civin et al. |
| 7,884,120 B2 | 2/2011 | Al-Qawasmeh |
| 7,888,118 B2 | 2/2011 | Shin et al. |
| 7,989,089 B2 | 8/2011 | Wang et al. |
| 8,148,392 B2 | 4/2012 | Huesca et al. |
| 8,394,815 B2 | 3/2013 | Al-Qawasmeh |
| 8,969,372 B2 | 3/2015 | Huesca |
| 8,987,305 B2 | 3/2015 | Al-Qawasmeh |
| 9,567,643 B2 | 2/2017 | Rice |
| 10,080,739 B2 | 9/2018 | Huesca et al. |
| 2002/0119955 A1 | 8/2002 | Doyle et al. |
| 2004/0127527 A1 | 7/2004 | Mistuya et al. |
| 2004/0176601 A1 | 9/2004 | Goulet |
| 2004/0235073 A1 | 11/2004 | Ruppert et al. |
| 2004/0265628 A1 | 12/2004 | Wang et al. |
| 2005/0186442 A1 | 8/2005 | Gros |
| 2005/0195793 A1 | 9/2005 | Dalton et al. |
| 2005/0282285 A1 | 12/2005 | Radhamohan et al. |
| 2007/0105929 A1 | 5/2007 | Al-Qawasmeh |
| 2007/0123553 A1 | 5/2007 | Huesca |
| 2009/0232767 A1 | 9/2009 | Frankel |
| 2010/0168417 A1* | 7/2010 | Huesca ............... C07D 471/14 540/597 |
| 2010/0261174 A1 | 10/2010 | Grande et al. |
| 2010/0311683 A1 | 12/2010 | Beach et al. |
| 2011/0097343 A1 | 4/2011 | Atanackovic et al. |
| 2011/0152337 A1 | 6/2011 | Al-Qawasmeh |
| 2011/0171221 A1 | 7/2011 | Vieweg et al. |
| 2011/0281277 A1 | 11/2011 | Lee |
| 2011/0306602 A1 | 12/2011 | Wabnitz et al. |
| 2012/0100131 A1 | 4/2012 | Takayangi |
| 2012/0172244 A1 | 7/2012 | Buechler et al. |
| 2012/0251509 A1 | 10/2012 | Waldman et al. |
| 2013/0011411 A1 | 1/2013 | Pestell et al. |
| 2013/0034862 A1 | 2/2013 | Fantl et al. |
| 2013/0177632 A1 | 7/2013 | Al-Qawasmeh |
| 2013/0253842 A1 | 9/2013 | Sherwood et al. |
| 2014/0011279 A1 | 1/2014 | Yamanaka et al. |
| 2015/0099775 A1 | 4/2015 | Rice |
| 2015/0104392 A1 | 4/2015 | Rice |
| 2015/0374669 A1 | 12/2015 | Huesca |
| 2017/0335400 A1 | 11/2017 | Rice |
| 2019/0062842 A1 | 2/2019 | Rice |

FOREIGN PATENT DOCUMENTS

| | | |
|---|---|---|
| CN | 1289774 | 9/1999 |
| CN | 1289775 | 9/1999 |
| DE | 3141063 | 10/1985 |
| DE | 3422175 | 12/1985 |
| DE | 10323591 | 12/2004 |
| EP | 0077024 | 4/1983 |
| EP | 0165588 | 12/1985 |
| EP | 0812829 | 12/1997 |
| EP | 1428831 | 6/2004 |
| JP | 02258017 | 10/1990 |
| JP | 11199582 | 7/1999 |
| JP | 2000-273088 | 10/2000 |
| JP | 2001-506997 | 5/2001 |
| JP | 2002-275458 | 9/2002 |
| JP | 2002-364578 | 12/2002 |
| JP | 2004-528206 | 9/2004 |
| JP | 2006-503817 | 2/2006 |
| WO | WO-1993/014081 | 7/1993 |
| WO | WO-1994/011685 | 5/1994 |
| WO | WO-1995/003297 | 2/1995 |
| WO | WO-1996/018626 | 6/1996 |
| WO | WO-1998/027108 | 6/1997 |
| WO | WO-1997/036587 | 10/1997 |
| WO | WO-1998/014081 | 4/1998 |
| WO | WO-1998/027065 | 6/1998 |
| WO | WO-1999/001128 | 1/1999 |
| WO | WO-1999/001205 | 1/1999 |

(56) References Cited

FOREIGN PATENT DOCUMENTS

| | | |
|---|---|---|
| WO | WO-1999/002155 | 1/1999 |
| WO | WO-1999/007701 | 2/1999 |
| WO | WO-2000/059541 | 3/2000 |
| WO | WO-2000/033836 | 6/2000 |
| WO | WO-2000/068206 | 11/2000 |
| WO | WO-2000/068266 | 11/2000 |
| WO | WO-2000/078761 | 12/2000 |
| WO | WO-2001/026467 | 4/2001 |
| WO | WO-2002/024680 | 3/2002 |
| WO | WO-2002/046168 | 6/2002 |
| WO | WO-2002/072576 | 9/2002 |
| WO | WO-2002/083111 | 10/2002 |
| WO | WO-2003/004023 | 1/2003 |
| WO | WO-2003/032984 | 4/2003 |
| WO | WO-2003/066579 | 8/2003 |
| WO | WO-2003/087026 | 10/2003 |
| WO | WO-2004/005264 | 1/2004 |
| WO | WO-2004/016086 | 2/2004 |
| WO | WO-2004/042207 | 5/2004 |
| WO | WO-2005/047266 | 5/2005 |
| WO | WO-2006/012903 | 2/2006 |
| WO | WO-2006/081824 | 8/2006 |
| WO | WO-2006/126177 | 11/2006 |
| WO | WO-2007/000170 | 1/2007 |
| WO | WO-2008/125883 | 10/2008 |
| WO | WO-2010/102393 | 9/2010 |
| WO | WO-2012/006032 | 1/2012 |
| WO | WO-2013/149039 | 10/2013 |
| WO | WO-2015/051302 | 4/2015 |
| WO | WO-2015/051304 | 4/2015 |
| WO | WO-2015/108986 | 7/2015 |
| WO | WO-2019/089511 | 5/2019 |

OTHER PUBLICATIONS

Konecny et al. "PARP inhibitors for BRCA1/2-mutated and sporadic ovarian cancer: current practice and future directions", Br J Cane, Oct. 13, 2016, vol. 115(10), pp. 1157-1173. (Year: 2016).*
Mudasir et al. "DNA Binding of Iron(II)-Phenanthroline Complexes: Effect of Methyl Subtitution on Thermodynamic Parameters", Z. Naturforsch, 2008, vol. 63b, pp. 37-46. (Year: 2008).*
Abdel-Meguid et al. (1994). "An Orally Bioavailable HIV-1 Protease Inhibitor Containing an Imidazole-Derived Peptide Bond Replacement: Crystallographic and Pharmacokinetic Analysis." Biochemistry. 33: 11671-11677.
Abdel-Rahman et al. (2005). "Comprehensive characterization of HNPCC-related colorectal cancers reveals striking molecular features in families with no germline mismatch repair gene mutations," Oncogene, 24:1542-1551.
Adams et al. (2001). "Pyrimidinylimidazole Inhibitors of p38: Cyclic N-1 Imidazole Substituents Enhance p38 Kinase Inhibition and Oral Activity." Bioorganic and Medicinal Chemistry Letters. 11: 2867-2870.
Alakhov et al. (1999). "Block copolymer-based formulation of doxombicin. From cell screen to clinical trials," Colloids and Surfaces B: Biointerfaces, vol. 16, pp. 113-134.
Albitar et al. (2002). "Myelodysplastic syndrome is not merely "preleukemia"." Blood. 100(3): 791-798.
Allen et al. (2002). "Controlling the physical behavior and biological performance of liposome formulations through use of surface grafted poly(ethylene glycol)," Biosciences Reports, vol. 22(2), pp. 225-250.
Allen et al. (1992). "Stealth liposomes: an improved sustained release system for 1-beta-D-arabinofuranosylcytosine," Cancer Res., vol. 52, pp. 2431-2439.
Al-Sarraj et al. (2005). "Specificity of transcriptional regulation by the zinc finger transcription factors Sp1, Sp3, and Egr-1," J Cell Biochem., vol. 94(1), pp. 153-167.
Andrews (2001). "Cellular zinc sensors: MTF-1 regulation of gene expression," Biometals, vol. 14, pp. 223-237.

Antolini et al (1999). "Analogues of 4,5-bis(3,5-Dichlorophenyl)-2-Trifluoromethyl-1 H-Imidazole as Potential Antibacterial Agents." Bioorganic and Medicinal Chemistry Letters. 9(7): 1023-1028.
Armesto et al. (1988). "A New Site Selective Synthesis of Benzoin Esters, Synthesis of Symmetrically and Unsymmetrically Substituted Benzils." Synthesis. 1988(10): 799-801.
Arroyo et al. (1977). "Therapy of Murine Aspergillosis with Amphotericin B in Combination with Rifampin or 5-Fluorocytosine." Antimicrobial Agents and Chemotheraphy. pp. 21-25.
Bhaduri et al. (1996). "Potential Antifertility Agents: Syntheses of 2,4,5-Substituted Imidazoles." Indian Journal of Chemistry; 4(9): 419-420.
Bian et al. (2002). "Syntheses, spectroscopic and crystal structural studies of novel imidazo[4,5-f]1,10-phenanthroline derivatives and their Eu(III) ternary complexes with dibenzoylmethane," Polyhedron, vol. 21, pp. 313-319.
Bian et al. (2003). "The Convenient Synthesis of Amphiphilic Phenanthroline Derivatives," Synthetic Communications, vol. 33(20), pp. 3477-3482.
Bing et al. (2004). "Synthesis of efficient blue and red light emitting phenanthroline derivatives containing both hole and electron transporting properties," Tetrahedron Letters, vol. 45(33), pp. 6361-6363.
Bishop et al. (1996). "A randomized study of high-dose cytarabine in induction in acute myeloid leukemia." Blood. 87(5): 1710-1717.
Botana et al. (2004). "p-(1 H-Phenanthro[9,1 0-d]imidazo/-2-y/)-Substituted Calix[4]arene, a Deep Cavity for Guest Inclusion." Organic Letters. 6(7): 1091-1094.
Boyd et al. (1992). "Data Display and Analysis Strategies for the NCI Disease-Oriented In Vitro Antitumor Drug Screen," In Cytotoxic Anticancer Drugs: Models and Discovery and Development, Klimar Academic, Hingham, MA, pp. 11-34.
Bu et al. (1996). "A novel approach to synthesis of tricyanovinylthiophene for heterocyclic imidazole nonlinear optical chromophores," Tetrahedron Letters. 37 (41): 7331-7334.
Buss et al. (2004). "Iron Chelators in Cancer Chemotherapy." Curr.Top Med. Chem. 4(15): 1623-1635.
Cairo et al. (1995). "Induction of Ferritin Synthesis by Oxidative Stress," J. Biol. Chem., vol. 270(2), pp. 700-703.
Cammack et al. (1993). "EPR Spectroscopy of Iron," Methods Enzymol., vol. 227, Academic Press, Inc. pp. 353-384.
Cantley. (2002). "The phosphoinositide 3-kinase pathway," Science, vol. 296. pp. 1655-1657.
CAS Registry No. 309285-51-6, entered Registry file on STN on Dec. 18, 2000.
CAS Registry No. 330449-52-0, entered Registry file on STN on Apr. 6, 2001.
CAS Registry No. 330449-64-4, entered into Registry file in STN on Apr. 6, 2001.
CAS Registry No. 332148-67-1, entered Registry file on STN on Apr. 21, 2001.
CAS Registry No. 404904-57-0, entered Registry file on STN on Apr. 10, 2002.
CAS Registry No. 416872-13-4, entered into Registry file in STN on May 16, 2002.
Cercek et al. (2013). "Phase I study of LOR-253, a novel inducer of Krüppel-like factor 4, in patients with advanced solid tumors." Eur. J. Cancer; 49(Suppl. 2):S179-S180, Abstract 864, 2 pages.
Cercek et al. (2015). "Phase I study of Compound I HCI, an Inducer of KLF4, in Patients with Advanced or Metastatic Solid Tumors," Invest. New Drugs. 33(5): 1086-92.
Chao et al. (2000). "Synthesis, electrochemical and spectroscopic properties of ruthenium(II) complexes containing 1,3-bis([1,10]phenanthroline-[5,6-d]imidazol-2-yl)benzene." Polyhedron;19 (16-17): 1975-1983.
Chao et al. (2001). "Mono-, di- and tetra-nuclear ruthenium(II) complexes containing 2,2?-p-phenylenebis(imidazo[4,5-f?]phenanthroline): synthesis, characterization and third-order nonlinear optical properties." J. Chem. Soc., Dalton Trans.; 1920-1926.
Chaston et al. (2003). "Examination of the Antiproliferative Activity of Iron Chelators." Clin. Cancer Research (2003); 9(1): 402-414.
Chawengsaksophak et al. (1997). "Homeosis and intestinal tumours in Cdx2 mutant mice," Nature, 386(6620):84-7—Abstract.

(56) References Cited

OTHER PUBLICATIONS

Chen et al. (2000). "Gut-enriched Krüppel-like factor represses cyclin D1 promoter activity through Sp1 motif," Nucleic Acids Research, vol. 28(15), pp. 2969-2976.
Chen et al. (2001). "Krüppel-like Factor 4 (Gut-enriched Krüppel-like Factor) Inhibits Cell Proliferation by Blocking G1/S Progression of the Cell Cycle." J. Biol. Chem. 276(32): 30423-30428.
Chen et al. (2002). "A possible tumor suppressor role of the KLF5 transcription factor in human breast cancer." Oncogene; 21: 6567-6572.
Chen et al. (2002). "Gut-enriched Krupel-like Factor Represses Ornithine Decarboxylase Gene Expression and Functions as Checkpoint Regulator in Colonic Cancer Cells," J. Biol. Chem., vol. 277(48), pp. 46831-46839.
Chen et al. (2003). "Transcriptional Profiling of Krüppel-like Factor 4 Reveals a Function in Cell Cycle Regulation and Epithelial Differentiation," J. Mol. Biol., vol. 326(3), pp. 665-677.
Chen et al. (2004). "Krüppel-like factor 4 is transactivated by butyrate in colon cancer cells," J. Nutr., vol. 134(4) pp. 792-798.
Chen et al. (2005). "Bleomycins: towards better therapeutics." Nat. Rev. Cancer (2005); 5(2): 102-112.
Chi, K. (1994). "Palladium Catalyst in DMSO for the Oxidation of Tolans to Benzils." Synthetic Communications. 24(15): 2119-2122.
CN 201480064470.2, Search Report with English translation, dated Jul. 24, 2017, 8 pages.
Cohen, S.R. et al. (1995). "The McGill Quality of Life Questionnaire: a measure of quality of life appropriate for people with advanced disease. A preliminary study of validity and acceptability," Palliative Medicine, vol. 9, pp. 207-219.
Coyle-Rink, J. et al. (2002). "Developmental Expression of Wnt Signaling Factors in Mouse Brain," Cancer Biology & Therapy, vol. 1(6), pp. 640-645.
Crittenden. "An interpretation of familial aggregation based on multiple genetic and environmental factors". Ann. N. Y. Acad. Sci. 91 (3): 769-80.
Crosasso, P. et al.(2000). "Preparation, characterization and properties of sterically stabilized paclitaxel-containing liposomes," J. Controlled Release, vol. 63, pp. 19-30.
Cuenda et al. (1995). "SB 203580 is a specific inhibitor of a MAP kinase homologue which is stimulated by cellular stresses and interleukin-1." Federation of European Biochemical Societies Letters. 364: 229-233.
Cuenda et al. (1997). "Activation of stress-activated protein kinase-3 (SAPK3) by cytokines and cellular stresses is mediated via SAPKK3 (MKK6); comparison of the specificities of SAPK3 and SAPK2 (RK/p38)," The EMBO Journal. 16(2): 295-305.
Cukier et al. (2013). "Abstract 4649: Utilizatrion of KLF-4 as a pharmacodynamic biomarker for in vivo anticancer activity of a novel small molecule drug LOR-253," Cancer Res. 73(8 Supplement):Abstract 4649, 4 pages.
Da Costa et al. (1999). "CDX2 is mutated in a colorectal cancer with normal APC/b-catenin signaling," Oncogene, 18(35):5010-5014.
Dang, D.T., et al. (2000). "Decreased expression of the gut-enriched Krüppel-like factor gene in intestinal adenomas of multiple intestinal neoplasia mice and in colonic adenomas of familial adenomatous polyposis patients." FEBS Letters. 476(3): 203-207.
Dang, D.T. et al. (2001). "Expression of the gut-enriched Krüppel-like factor (Krüppel-like factor 4) gene in the human colon cancer cell line RKO is dependent on CDX2," Oncogene, vol. 20(35) (2001) pp. 4884-4890.
Dang, D.T. et al. (2002). "Opposing effects of Krüppel-like factor 4 (gut-enriched Krüppel-like factor) and Krüppel-like factor 5 (intestinal-enriched Krüppel-like factor) on the promoter of the Krüppel-like factor 4 gene," Nucleic Acids Res., vol. 30(13) pp. 2736-2741.
Dang, D.T., et al. (2003). "Overexpression of Krüppel-like factor 4 in the human colon cancer cell line RKO leads to reduced tumorigenecity." Oncogene; 22: 3424-3430.
Database WPI; Section Ch. Week 199940, Derwent Publications Ltd., London, GB, AN 1999-474062(XP002268773) & JP 11199582 (English abstract) A (Sagami Chem Res Cent), Jul. 27, 1999, 4 pages.
Davies et al. (2017). "HRDetect is a Predictor of BRCA1 and BRCA2 Deficiency Based on Mutational Signatures," Nat. Med. 23(4): 517-525.
Degrolard-Courcet et al. (2013). "Development of primary early-onset colorectal cancers due to biallelic mutations of the FANCD1/BRCA2 gene," European Journal of Human Genetics, vol. 22, Iss. 8, pp. 979-987.
Delgado et al. (2012). "MYC oncogene in myeloid neoplasias." Clin. Transl. Oneal. vol. 15, pp. 87-94.
Demirayak et al. (1989). "Synthesis of Certain Derivatives of Ethyl a-[(phenanthro[9, I 0-d]imidazol-2-yl)phenoxy ]alkanoate." Acta Pharmaceutica Turcica. 31 (1): 19-25.
Dexter (1987). "Growth factors involved in haemopoiesis," J. Cell Sci. 88: 1-6.
Diekema et al. (2001). "Survey of Infections due to *Staphylococcus* Species: Frequency of Occurrence and Antimicrobial Susceptibility of Isolates Collected in the United States, Canada, Latin America, Europe, and the Western Pacific Region for the SENTRY Antimicrobial Surveillance Program, 1997-1999." Clinical Infectious Diseases; 32:S114-132.
Dora et al. (1979). "Synthesis of Some Fused 2-arylimidazoles and their Derivatives." Journal of Indian Chemical Society. 56(6): 620-624.
Dos Santos et al. (2002). "Improved retention of idarubicin after intravenous injection obtained for cholesterol-free liposomes," Biochim Biophys. Acta., vol. 1561, pp. 188-201.
Dos Santos et al. (2004). "pH gradient loading of anthracyclines into cholesterol-free liposomes: enhancing drug loading rates through use of ethanol," Biochim. Biophys. Acta, vol. 1661, pp. 47-60.
Downey et al. (1980). "Degradation of DNA by 1,-10-phenanthroline." Biochem Biophys Res Commun. 93(1): 264-270.
Drenan et al. (2004). "FKBP12-Rapamycin-associated Protein or Mammalian Target of Rapamycin (FRAP/mTOR) Localization in the Endoplasmic Reticulum and the Golgi Apparatus," J. Biol. Chem., vol. 279(1), pp. 772-778.
Drummond et al. (1999). "Optimizing liposomes for delivery of chemotherapeutic agents to solid tumors." Pharmacological Reviews, vol. 51(4), pp. 691-743.
Eisenstein et al. (1998). "Iron Regulatory Proteins, Iron Responsive Elements and Iron Homeostasis." J. Nutr., vol. 128(12), pp. 2295-2298.
Ekwall (1983). "Screening of Toxic Compounds in Mammalian Cell Cultures." Annals New York Academy of Sciences. 407(1): 64-77.
Embree et al. (1998) "Pharmacokinetic behavior of vincristine sulfate following administration of vincristine sulfate liposome injection," Cancer Chemothr. Pharmacol., vol. 41, pp. 347-352.
Enoiu et al. (2012). "Repair of Cisplatin-induced DNA Interstrand Crosslinks by a Replication-independent Pathway Involving Transcription-coupled Repair and Translesion Synthesis." Nucleic Acids Res. 40(18): 8953-64.
Estey (2014). "Treatment of acute myelogenous leukemia". Oncology (Williston Park) 16 (3): 343-52, 355-6; discussion 357, 362, 365-6, 2002—retrieved online at http://www.cancernetwork.com Dec. 9, 2014.
Extended European Search Report in European Patent Application No. 14850583.7, dated May 2, 2017, 10 pages.
Faber, et al. (2013). "CDX2-driven leukemogenesis involves KLF4 repression and deregulated PPAR? signaling", J Clin Invest. 123(1): 299-314.
Fenaux et al. (1999). "A randomized comparison of all transretinoic acid (ATRA) followed by chemotherapy and ATRA plus chemotherapy and the role of maintenance therapy in newly diagnosed acute promyelocytic leukemia. The European APL Group". Blood 94 (4): 1192-200.
Fields et al. (1993). "Dual-attribute continuous monitoring of cell proliferation/cytotoxicity," Am. Biotechnol. Lab., vol. 11, pp. 48-50.
File et al. (2004). "Antimicrobial therapy of community-acquired pneumonia," Infect. Dis. Clin. North Am., vol. 18, pp. 993-1016.

(56) References Cited

OTHER PUBLICATIONS

Fischer et al. (1961). "Dissociation Constants of the Conjugate Acids of Substituted Benzyl Phenyl Ketones and of Alkyl-substituted Benzophenones." Journal of American Chemical Society; 83: 4208-4210.
Flatmark et al. (1976). "Mitochondrial 'Non-Heme Non-FeS Iron' and It's Significance in the Cellular Metabolism of Iron," Proteins of Iron Metabolism, Brown, Aisen, Fielding and Crichton, eds., New York, Grun & Stratton, pp. 349-358.
Florean et al. (2011). "Epigenomics of leukemia: from mechanisms to therapeutic applications". Epigenomics. 3(5): 581-609.
Foley et al. (1965). "Continuous culture of human lymphoblasts from peripheral blood of a child with acute leukemia." Cancer. 18: 522-529.
Foster et al. (2000). "Increase of GKLF Messenger RNA and Protein Expression during Progression of Breast Cancer." Cancer Res. 60(22): 6488-6495.
Foster et al. (1999). "Oncogene expression cloning by retroviral transduction of adenovirus E1A-immortalized rat kidney RK3E cells: transformation of a host with epithelial features by c-MYC and the zinc finger protein GKLF." Cell Growth Differ. 10(6): 423-434.
Fruman et al. (1998). "Phosphoinositide kinases," Annu. Rev. Biochem., vol. 67, pp. 481-507.
Fruman et al. (1999). "Phosphoinositide binding domains: embracing 3-phosphate," Cell, vol. 97(7), pp. 817-820.
Gabizon et al. (1990). "Effect of liposome composition and other factors on the targeting of liposomes to experimental tumors: biodistribution and imaging studies," Cancer Res., vol. 50, pp. 6371-6378.
Gaidenko, T.A. et al., "The PrpC serine threonine phosphatase and PrkC kinase have opposing physiological roles in stationary-phase Bacillus subtilis cells," J. of Bacteriol., vol. 184(22) (2002) pp. 6109-6114.
Gales et al. (2001). "Characterization of Pseudomonas aeruginosa Isolates: Occurrence Rates, Antimicrobial Susceptibility Patterns, and Molecular Typing in the Global SENTRY Antimicrobial Surveillance Program, 1997-1999." Clinical Infectious Diseases. 32:S146-155.
Gao et al. (2002). "Synthesis and electroluminescence properties of an organic europium complex," Journal of Alloys and Compounds 358(1-2):188-192.
Ghaleb et al. (2005). "Krüppel-like factors 4 and 5: the yin and yang regulators of cellular proliferation." Cell Research. 15(2): 92-96.
Ghaleb et al. (2007). "Krüppel-like factor 4 exhibits antiapoptotic activity following ?-radiation-induced DNA damage." Oncogene. 26: 2365-2373.
Ghannoum et al. (1996). "Susceptibility Testing of Fungi: Current Status of Correlation of In Vitro Data with Clinical Outcome." Journal of Clinical Microbiology. 34: 489-495.
Golde and Gasson. (1988). "Hormones That Stimulate the Growth of Blood Cells." Scientific American, pp. 62-70.
Goldman. (2017). "Lorus Therapeutics, Inc. The Next Major Oncology Player," Goldman Small Cap Research, 13 pages (2012), http://www.baystreet.ca/articles/research_reports/goldman_research/LOR-1 0.9.12-[3].pdf [retrieved on Apr. 12, 2017].
Goto et al. (1999). "Improved efficacy with non simultaneous administration of netilmicin and minocycline against methicillin-resistant Staphylococcus aureus in in vitro and in vivo models." International Journal of Antimicrobial Agents. 11(1): 39-46.
Gower et al. (1989). "Determination of Desferrioxamine-Available Iron in Biological Tissues by High-Pressure Liquid Chromatography." Analytical Biochemistry, vol. 180, pp. 126-130.
Greenberg et al. (2011). "Myelodysplastic Syndromes," Journal of the National Comprehensive Cancer Network. 9(1): 30-56.
Greenstein et al. (2003). "Characterization of the MM.1 human multiple myeloma (MM) cell lines: a model system to elucidate the characteristics, behavior, and signaling of steroid-sensitive and -resistant MM cells." Exp Hematol. 31(4): 271-282.
Grimmett (1984). "Imidazoles and their Benzo Derivatives: (iii) Synthesis and Applications, 4.08.1 Ring Synthesis from Non-Heterocyclic Compounds," Comprehensive Heterocyclic Chemistry: the Structure, Reaction, Synthesis and Uses of Heterocyclic Compounds, Katrizky and Rees, eds., vol. 5, Pergamon Press, Oxford, pp. 457-498.
Gross et al. (2000). "Identification of the Copper Regulon in *Saccharomyces cerevisiae* by DNA Microarrays," J. Biol. Chem., vol. 275(41), pp. 32310-32316.
Guan et al. (2003). "Bright Red Light-Emitting Electroluminescence Devices based on a functionalize Europium Complex." New Journal of Chemistry 27(12): 1731-1734.
Guijarro et al. (1999). "The Reaction of Active Zinc with Organic Bromides." Journal of American Chemical Society. 21(7): 4155-4157.
Hanai et al. (2000). "Prediction of retention factors of phenolic and nitrogen-containing compounds in reversed-phase liquid chromatography based on logP and pKa obtained by computational chemical calculation," Journal of Liquid Chromatography & Related Technologies, vol. 23(3), pp. 363-385.
Haroon et al. (2004). "Loss of metal transcription factor-I suppresses tumor growth through enhanced matrix deposition," FASEB J., vol. 18(11), pp. 1176-1184.
Heerding et al. (2001). "1,4 Disubstituted Imidazoles are Potential Antibacterial Agents Functioning as Inhibitors of Enoyl Acyl Carrier Protein Reductase (FabI)." Biorganic and Medicinal Chemistry Letters. 11: 2061-2065.
Hiort et al. (1993). "DNA binding of ? - and ?-[Ru(phen)2DPPZ]2+." J. Am. Chem. Soc., vol. 115, pp. 3448-3454.
Hoban et al. (2001). "Worldwide Prevalence of Antimicrobial Resistance in *Streptococcus pneumoniae*, Haemophilus influenzas, and Moraxella catarrhalis in the SENTRY Antimicrobial Surveillance Program, 1997-1999." Clinical Infectious Diseases. 32:S81-93.
Hollingshead et al. (1995). "In Vivo Cultivation of Tumor Cells in Hollow Fibers," Life Sciences, vol. 57(2), pp. 131-141.
Horig et al. (2004). "From bench to clinic and back: Perspective on the 1st IQPC Translational Research conference." Journal of Translational Medicine. 2(1): 44.
Horwitz et al. (1996). "Anticipation in familial leukemia". Am. J. Hum. Genet. 59 (5): 990-998.
Huesca et al. (2002). "Adhesion and Virulence Properties of Epidemic Canadian Methicillin-Resistant *Staphylococcus aureus* Strain 1: Identification of Novel Adhesion Functions Associated with Plasmin-Sensitive Surface Protein." The Journal of Infectious Diseases. 185: 1285-1296.
Huesca et al. (2009). "A novel small molecule with potent anticancer activity inhibits cell growth by modulating intracellular labile zinc homeostasis." Mol Cancer Ther. 8: 2586-2596.
Hughes-Davies et al. (2003). "EMSY links the BRCA2 pathway to sporadic breast and ovarian cancer." Cell. 115(5): 523-35.
Iacobucci et al. (2012). "Cytogenetic and molecular predictors of outcome in acute lymphocytic leukemia: recent developments", Curr Hematol Malig Rep. 7(2): 133-143.
International Preliminary Examination Report for PCTCA0301229, dated Dec. 3, 2004.
International Preliminary Report on Patentability, dated May 15, 2006, International Application No. PCT/IB2004/052433, 8 pages.
International Preliminary Report on Patentability for International Application No. PCT/IB2006/051675, dated Nov. 29, 2007, 6 pages.
International Preliminary Report on Patentability for International Application No. PCT/US2014/059142, dated Apr. 5, 2016, 9 pages.
International Preliminary Report on Patentability for PCT Application No. PCT/US14/59140, dated Apr. 5, 2016, 8 pages.
International Search Report (ISR) of the International Searching Authority, dated Feb. 26, 2004; International Application No. PCT/CA2003/001229.
International Search Report of the International Searching Authority, dated Apr. 4, 2005; International Application No. PCT/IB2004/052433, 5 pages.
International search Report for International Application No. PCT/IB2006/051675, dated Jan. 3, 2007, 4 pages.

(56) References Cited

OTHER PUBLICATIONS

International Search Report issued by the International Searching Authority for PCT Application No. PCT/US14/59140, dated Dec. 31, 2014, 3 pages.
International Search Report issued by the International Searching Authority for PCT Application No. PCT/US2014/059142, dated Dec. 31, 2014, 3 pages.
International Search Report of the International Searching Authority, dated Feb. 7, 2019; International Application No. PCT/US2018/058103, 5 pages.
Isikdağ et al. (1995). "QSAR of Inhibitory Activities by 2,4,5-Trisubstituted Imidazole Derivatives on Tubifex Worms." Acta Pharmaceutica Turcica. 37(1): 19-24.
Isikdağ et al. (1999). "Synthesis and analgesic activities of 2-substituted-1 H-phenantro [9, 10-d] imidazoles," Boll. Chim. Farmaceutico, 138:453-456.
Ito et al. (1979). "Photochemical Reaction of Imidazoles with Unsaturated Nitriles. Chemistry of Encounter Complex and Ion Pair," J. Org. Chem. 44:41-49.
Ivashkevich et al. (2012). "Use of the Gamma-H2AX Assay to Monitor DNA Damage and Repair in Translational cancer Research." Cancer Lett. 327(1-2): 123-33.
Iwahi et al. (1982). "Virulence of *Escherichia coli* in Ascending Urinary-Tract Infection in Mice." Journal of Medical Microbiology. 15: 303-316.
Janoff. (1999). "Liposomal delivery of drugs, genes and vaccines," Liposomes: Rational Design, Biotechnology Advances, vol. 17, pp. 511-513.
Jasin, M. (2002). "Homologous repair of DNA damage and tumorigenesis: the BRCA connection." Oncogene. 21(58): 8981-93.
Kaczynski et al. (2003). "Sp1- and Krüppel-like transcription factors." Genome Biology. 4(2): 206.1-206.8.
Karahoca and Momparler. (2013). "Pharmacokinetic and pharmacodynamic analysis of 5-aza-2'-deoxycytidine (decitabine) in the design of its dose-schedule for cancer therapy." Clin Epigenetics. 5(1): 3, pp. 1-16.
Khanna et al. (2001). "DNA double-strand breaks: signaling, repair and the cancer connection." Nature genetics. 27(3): 247.
Kihara et al. (2001). "Beclin-phosphatidylinositol 3-kinase complex functions at the trans-Golgi network," EMBO Rep., vol. 2(4), pp. 330-335.
Kimura et al. (2002). "Preparation of 4-( 4,5-Diphenyl- IH-imidazol-2-yl) benzaldehyde and Its Practical Synthetic Use in the Synthesis of Unsymmetrically Substituted Imidazoles." New Technologies & Medicine. 3(1) :30-34.
Kimura et al. (2012). "Antiproliferative and Antitumor Effects of Azacitidine Against the Human Myelodysplastic Syndrome Cell Line SKM-1." Anticancer Research. 32: 795-798.
Kindermann et al. (2004)."Identification of Genes Responsive to Intracellular Zinc Depletion in the Human Colon Adenocarcinoma Cell Line HT-29." The Journal of Nutrition. 134(1): 57-62.
Kindermann et al. (2005). "Zinc-sensitive genes as potential new target genes of the metal transcription factor-1 (MTF-1)." Biochemistry and Cell Biology. 83(2): 221-229.
King et al. (1992). "Physiological pharmacokinetic parameters for cis-dichlorodiammineplatinum (II) (DDP) in the mouse," J. Pharmacokinet. Biophar., vol. 20 (1), pp. 95-99.
Kitano et al. (1991). "Suppression of proliferation of human epidermal keratinocytes by 1,25-dihydroxyvitamin D3," Euro J. Clin. Invest., vol. 21, pp. 53-58.
Klose et al. (2000). "The Suckling Mouse Model of Cholera." Trends in Microbiology. 8: 189-191.
Kozlov et al. (1992). "Intracellular free iron in liver tissue and liver homogenate: Studies with electron paramagnetic resonance on the formation of paramagnetic complexes with desferal and nitric oxide," Free Radical Biology and Medicine, vol. 13, pp. 9-16.
Krieg, B. and Manecke, G. (1967). "Synthesis and Semiconductor Properties of Aryl-substituted Imidazoles." ("Synthese and Halbleitereigenschaften arylsubstitulerter Imidazole.") Z. Naturforsch; 22b: 132-141, and English translation.

Kurtz et al. (2015). "Broad Activity of APTO-253 in AML and other Hematologic Malignancies Correlates with KFL4 Expression Level [abstract]," Blood. 126: 1358.
Langmade et al. (2000). "The Transcription Factor MTF-1 Mediates Metal Regulation of the Mouse ZnT1 gene," J. Biol. Chem., vol. 275(44), pp. 34803-34809.
Lantos (1975). "Reaction of Phenanthrenequinone with Ammonium Acetate," J. Org. Chem., 40(11): 1641-1642.
Ledermann et al. (2012). "Olaparib Maintenance Therapy in Platinum-Sensitive Relapsed Ovarian Cancer," N. Engl. J Med. 366(15): 1382-92.
Lee et al. (1994). "A Protein Kinase Involved in the Regulation of Inflammatory Cytokine Biosynthesis." Nature. 327: 739-745.
Lengerke et al. (2008). "BMP and Wnt specify hematopoietic fate by activation of the Cdx-Hox pathway", Cell Stem Cell. 2(1): 72-82.
Lengerke et al. (2012). "Caudal genes in blood development and leukemia", Ann N Y Acad Sci. 1266: 47-54.
Lewis. (1998). "Muscarine, imidazole, oxazole, thiazole and peptide alkaloids, and other miscellaneous alkaloids." Natural Product Reports (1998); 15: 371-395.
Lewis (1998). "Muscarine, imidazole, oxazole, thiazole and peptide alkaloids, and other miscellaneous alkaloids." Natural Product Reports. 15: 417-437.
Lewis. (1999). "Miscellaneous alkaloids: Amaryllidaceae, Sceletium, muscarine, imidazole, oxazole, peptide and other miscellaneous alkaloids." Natural Product Reports. 16: 389-416.
Lichtlen et al. (2001). "Putting its fingers on stressful situations: the heavy metal-regulatory transcription factor MTF-1," Bioessays, vol. 23(11), pp. 1010-1017.
Liggins et al. (1997). "Solid-state characterization of paclitaxel," J. Pharm. Sci., vol. 86 (12), pp. 1458-1563.
Linden. (2002). "Treatment options for vancomycin-resistant enterococcal infections," Drugs, vol. 62, pp. 425-441.
List et al. (1990). "The myelodysplastic syndromes: biology and implications for management", J. Clinical Onc. 8(8): 1424-1441.
Liu et al. (2000). "Synthesis, Characterization and Antitumor Activity of a Series of Polypyridyl Complexes," Metal Based Drugs, 7(6):343-348.
Liu et al. (2004). "Polymer-drug compatibility: a guide to the development of delivery systems for the anticancer agent, ellipticine," J. Pharm. Sci., vol. 93(1), pp. 132-143.
Liu et al. (2005). "Influence of serum protein on polycarbonate-based copolymer micelles as a delivery system for a hydrophobic anti-cancer agent," J. Controlled Release, vol. 103, pp. 481-497.
Lock et al. (2004). "Molecular mechanisms of growth inhibition induced by novel aryl-imidazole compounds in human cancer cells" Presented at IBC's 9th Annual World Congress Drug Discovery Technology Meeting (Boston Aug. 8-13, 2004) Abstract.
Lockshin et al. (2004). "Apoptosis, autophagy and more," Int. J. Biochem. Cell Biol., vol. 36(12), pp. 2405-2419.
LoGrasso et al. (1997). "Kinetic Mechanism for p38 MAP Kinase." Biochemistry. 36: 10422-10427.
Lombardi et al. (2007). "Molecular characterization of human multiple myeloma cell lines by integrative genomics: insights into the biology of the disease. Genes Chromosomes." Cancer. 46(3): 226-238.
Low et al. (2001). "Clinical Prevalence, Antimicrobial Susceptibility, and Geographic Resistance Patterns of Enterococci: Results from the SENTRY Antimicrobial Surveillance Program, 1997-1999." Clinical Infectious Diseases. 32: S133-145.
Lowy. (1998). "*Staphylococcus aureus* infections," N. Engl. J. Med, vol. 339(8), pp. 520-532.
Lukyanov et al. (2002). "Polyethylene glycol-diacyllipid micelles demonstrate increased accumulation in subcutaneous tumors, in mice," Phar. Res., vol. 19(10), pp. 1424-1429.
Lum et al. (2014). "Abstract 4544: Induction of KLF4 by LOR-253 as an innovative therapeutic approach to induce apoptosis in acute myeloid leukemia." Cancer Res. 74(19 supplement):Abstract 4544, 4 pages.
Malik et al. (2014). "miR-2909-mediated regulation of KLF4: a novel molecular mechanism for differentiating between B-cell and T-cell pediatric acute lymphoblastic leukemias." Mol Cancer; 13: 175, 15 pages.

(56) References Cited

OTHER PUBLICATIONS

Mann et al. (2001). "1, 10-phenanthroline inhibits glycosylphosphatidylinositol anchoring by preventing phosphoethanolamine addition to glycosylphosphatidylinositol anchor precursors." Biochemistry. 40(5): 1205-1213.
Martini et al. (2002). "Iron Treatment Downregulates DMTI and IREG1 mRNA Expression in Caco-2 cells," J. Nutr., vol. 132(4), pp. 693-696.
McCabe et al. (1993). "Chelation of intracellular zinc triggers apoptosis in mature thymocytes." Lab. Invest. 69(1): 101-110.
McCorkle et al. (1978). "Development of a system distress scale," Cancer Nursing, vol. 1, pp. 373-378.
McLay et al. (2001). "The Discovery of RPR 200765A, a p38 MAP Kinase Inhibitor Displaying a Good Oral Anti-Arthritic Efficacy." Bioorganic & Medicinal Chemistry. 9: 537-554.
Medicines in Development for Infectious Diseases 2010, "Biopharmaceutical Research Continues Against Infectious Diseases with 395 Medicines and Vaccines in Testing," 36 pages.
Meijer et al. (2004). "Regulation and role of autophagy in mammalian cells," Int. J. Biochem. Cell Biol., vol. 36(12), pp. 2445-2462.
Meng-Er et al. (1988). "Use of all-trans retinoic acid in the treatment of acute promyelocytic leukemia". Blood. 72 (2): 567-572.
Michie. (1998). "The value of animal models in the development of new drugs for the treatment of the sepsis syndrome," Journal for Antimicrobial Chemotherapy. 41 (Sppl. A): 47-49.
Mirza et al. (2016). "Niraparib Maintenance Therapy in Platinum-Sensitive, Recurrent Ovarian Cancer," N. Engl. J Med. 375(22): 2154-64.
Mizumura et al. (2001). "Cisplatin-incorporated polymeric micelles eliminate nephrotoxicity, while maintaining antitumor activity," Japanese Journal of Cancer Research, vol. 92, pp. 328-336.
Moghimi et al. (1998). "Serum-mediated recognition of liposomes by phagocytic cells of the reticuloendothelial system—the concept of tissue specificity," Adv. Drug Deliv. Rev., vol. 32, pp. 45-60.
Moghimi et al. (2003). "Real-time evidence of surface modification at polystyrene lattices by poloxamine 908 in the presence of serum: in vivo conversion of macrophage-prone nanoparticles to stealth entities by poloxamine 908," FEBS. Lett., vol. 547, pp. 177-182.
Monks et al. (1991). "Feasibility of a High-flux Anticancer Drug Screen Using a Diverse Panel of Cultured Human Tumor Cell Lines," J. Natl. Cancer Inst., vol. 83(11), pp. 757-766.
Moribe et al. (1999). "Encapsulation characteristics of nystatin in liposomes: effects of cholesterol and polyethylene glycol derivatives," International Journal of Pharmaceutics, vol. 188, pp. 193-202.
Moylan et al. (1993). "Synthesis and Nonlinear Optical Properties of Donor-Acceptor 875 Substituted Triaryl Azole Derivatives." Chemistry of Materials. 5(10): 1499-1508.
Musolino et al. (2010). "Epigenetic therapy in myelodysplastic syndromes." European Journal of Haematology. 84(6): 463-473.
Nakanishi et al. (2001). "Development of the polymer micelle carrier system for doxorubicin," J. Controlled Release, vol. 74, pp. 295-302.
Narla et al. (2001). "KLF6, a Candidate Tumor Suppressor Gene Mutated in Prostate Cancer." Science. 294 (1551): 2563-2566.
Niell et al. (2004). "BRCA1 and BRCA2 Founder Mutations and the Risk of Colorectal Cancer," Journal of the National Cancer Institute, vol. 96, Iss. 1, pp. 15-21.
Nielson et al. (1993). "Non-Transferrin-Bound-Iron in Serum and Low-Molecular-Weight-Iron in the Liver of Dietary Iron-Loaded Rats," In. J. Biochem., vol. 25(2), pp. 223-232.
Nilsson et al. (1970). "Established immunoglobulin producing myeloma (IgE) and lymphoblastoid (IgG) cell lines from an IgE myeloma patient." Clin Exp Immunol. 7(4): 477-489.
Nippon Kagaku Zasshi vol. 92 (1971), pp. 365-370, and English Abstract.

O'Brien et al. (2000). "Investigation of the Alamar Blue (resazurin) fluorescent dye for the assessment of mammalian cell cytotoxicity," Eur. J. Biochem., vol. 267, pp. 5421-5426.
Ogawa (1989). "Hemopoietic stem cells: stochastic differentiation and humoral control of proliferation." Environ. Health Presp. 80: 199-207.
Ohnishi et al. (2003). "Downregulation and growth inhibitory effect of epithelial-type Krüppel-like transcription factor KLF4, but not KLF5, in bladder cancer." Biochem. Biophys. Res. Commun. 308(2): 251-256.
Öllinger et al. (1997). "Nutrient Deprivation of Cultured Rat Hepatocytes Increases the Desferrioxamine-available Iron Pool and Augments the Sensitivity to Hydrogen Peroxide," J. Biol. Chem., vol. 272(38), pp. 23707-23711.
Olynk et al. (1994). "Differential Production of TNK by Kupffer cells after phagocytosis of E. coli and C. albicans." American Journal of Physiology. 10: 1-8.
Pan et al. (1994). "DNA-binding proteins as site-specific nucleases," Molecular Microbiology. 12(3): 335-342.
Pandya et al. (2004). "Nuclear Localization of KLF4 Is Associated with an Aggressive Phenotype in Early-Stage Breast Cancer." Clin. Cancer Res. 10(8): 2709-2719.
Patel. (2003). "Clinical impact of vancomycin-resistant enterococci," J. Antimicrob. Chemother., vol. 51(Suppl. S3) pp. 13-21.
Pechkin et al. (2002). "Synthesis and Properties of 2-(2-Furyl)-and 2-(2-Thienyl)-1-methylphenanthro[9, 1 0-d]imidazoles." Russian Journal of Organic Chemistry (Translation of Zhurnal Organicheskoi Khimii). 38(5): 726-730.
Petrat et al. (2002). "The Chelatable Iron Pool in Living Cells: a Methodically Defined Quantity," Biol.Chem., vol. 383(3-4), pp. 489-502.
Pfaller and Yu. (2001). "Antifungal Susceptibility Testing." Infectious Disease Clinics of North America. 15: 1227-1245.
Pfaller et al. (1997). "Antifungal Susceptibility Testing: Technical Advances and Potential Clinical Applications." Clinical Infectious Diseases. 24: 776-784.
Pozharskii et al. (1971). "Synthesis and Transformations of 2-(2-Furyl)- and 2-[ß-2-Furyl)Vinyl] Phenanthr [9, 10] Imidazoles," Chem. Het. Comp., 7: 950-952.
Press Release—Aug. 9, 2004—"Lorus Therapeutics Inc to Present Results of Novel Anticancer Small Molecule Studies," http://www.lorusthera.com/news-events/pressrelease-lorus-therapeutics-inc-present-results-323.php.
Press Release—Aug. 23, 2005—"Lorus Identifies Novel Class of Lead Drug Candidates from Small Molecule Anticancer Program."
Press Release—May 12, 2004—"Lorus Announces Discovery of Novel Low Molecular Weight Compounds with Anticancer and Antibacterial Activity." BioFinance conference, Toronto, CA, http://www.lorusthera.com/news-events/press-release-lorus-announces-discovery-novel-low-302.php.
Qayyum et al. (2014). "Adult T-cell leukemia/lymphoma". Arch Pathol Lab Med. 38(2): 282-286.
Radice. (2002). "Mutations of BRCA genes in hereditary breast and ovarian cancer." J Exp Clin Cancer Res. 21(3 Suppl): 9-12.
Rameh et al. (1999). "The role of phosphoinositide 3-kinase lipid products in cell function," J. Biol. Chem., vol. 274(13), pp. 8347-8350.
Richardson. (2002). "Iron chelators as therapeutic agents for the treatment of cancer." Crit. Rev. Oncol. Hematol. 42(3): 267-281.
Roshal et al. (2003). "The Electronic Transitions and Spectra of Hetarylphenanthroimidazole Derivatives," J. Phys. Chem. 77: 1709-1714.
Rouhi et al. (2013). "Deregulation of the CDX2-KLF4 axis in acute myeloid leukemia and colon cancer." Oncotarget. 4(2): 174-175.
Rowland et al. (2005). "The KLF4 tumour suppressor is a transcriptional repressor of p53 that acts as a context-dependent oncogene." Nat Cell Biol. 5(7): 1074-1082, Abstract.
Rowland et al. (2006). "KLF4, p21 and context-dependent opposing forces in cancer.". Nat Rev Cancer. 6(1):11-23, Abstract.
Rubinstein et al. (1990). "Comparison of In Vitro Anticancer-Drug-Screening Data Generated with a Tetrazolium Assay Versus a Protein Assay Against a Diverse Panel of Human Tumor Cell Lines," J. Natl. Cancer Inst., vol. 82, pp. 1113-1118.

(56) References Cited

OTHER PUBLICATIONS

Saandi et al. (2013). "Regulation of the tumor suppressor homeogene Cdx2 by HNF4? in intestinal cancer." Oncogene. 32(32): 3782-3788, Abstract.
Sarshar et al. (2000). "2,4,5-Trisubstituted Imidazoles: Novel Nontoxic Modulators of P-glycoprotein Mediated Multidrug Resistance. Part 1." Biorganic and Medicinal Chemistry Letters. 10: 2599-2601.
Sarshar et al. (1996). "Imidazole Libraries on Solid Support." Tetrahedron Letters. 37: 835-838.
Schafer et al. (2008). "Failure is an option: learning from unsuccessful proof-of-concept trials." Drug Discovery Today. 13 (21/22): 913-916.
Schmelz et al. (2005). "Induction of gene expression by 5-Aza-2?-deoxycytidine in acute myeloid leukemia (AML) and myelodysplastic syndrome (MDS) but not epithelial cells by DNA-methylation-dependent and -independent mechanisms." Leukemia. 19(1): 103-111.
Schoenhals et al. (2013). "Krüppel-like factor 4 blocks tumor cell proliferation and promotes drug resistance in multiple myeloma," Haematologica. 98: 1442-1449.
Scholl et al. (2007). "The homeobox gene CDX2 is aberrantly expressed in most cases of acute myeloid leukemia and promotes leukemogenesis." J. Clin. Invest. 117(4): 1037-1048.
Scialli et al. (1997). "Protective effect of liposome encapsulation on paclitaxel developmental toxicity in the rat," Teratology, vol. 56, pp. 305-310.
Sharma et al. (1997). "Activity of paclitaxel liposome formulations against human ovarian tumor xenografts," Int. J. Cancer, vol. 71, pp. 103-107.
Sherr et al. (1995). "Inhibitors of mammalian G1 cyclin-dependent kinases," Genes and Development, vol. 9(10), pp. 1149-1163.
Shibata et al. (2000). "Therapeutic efficacy of J-111, 225, a novel trans-3, 5-disubstituted pyrrolidinylthio-1 methylcarbapenem, against experimental murine systemic infections." Journal of Antimicrobial Chemotherapy. 45: 379-382.
Shie et al. (2000). "Gut-enriched Krüppel-like factor represses cyclin D1 promoter activity through Sp1 motif," Nucleic Acids Res., vol. 28(15), pp. 2969-2976.
Shie et al. (2000). "Role of gut-enriched Krüppel-like factor in colonic cell growth and differentiation," Am. J. Physiol. Gastrointest. Liver Physiol., vol. 279(4), pp. 0806-0814.
Shields, J.M. et al., "Identification and Characterization of a Gene Encoding a Gut enriched Krüppel-like Factor Expressed during Growth Arrest," The Journal of Biological Chemistry, vol. 271(33) (1996) pp. 20009-20017.
Shulman et al. (1977). "Action of 1,1 0-phenanthroline transition metal chelates on P388 mouse lymphocytic leukaemic cells," Chem.-Biol. Interacteractions. 16(1): 89-99.
Siegel et al. (1995). "Doxorubicin encapsulated in sterically stabilized liposomes for the treatment of a brain tumor model: biodistribution and therapeutic efficacy," J. Neurosurg., vol. 83, pp. 1029-1037.
Sigman et al. (1979). "Oxygen-dependent cleavage of DNA by the 1,1 0-phenanthroline cuprous complex," J Biol Chem. 254(24): 12269-12272.
Simor et al. (1999). "Characterization and proposed nomenclature of epidemic strains of methicillin-resistant *Staphylococcus aureus* in Canada." Canada Communicable Disease Report. 25-12: 105-108.
Sircar et al. (1923). "Dyes Derived from Phenanthraquinone. Part III. Phenanthriminazoles," J. Chem. Soc., 123:1559-1565.
Skehan et al. (1990). "New Colorimetric Cytotoxicity Assay for Anticancer-Drug Screening," J. Natl. Cancer Inst., vol. 82, pp. 1107-1112.
Sopik et al. (2014). "BRCA1 and BRCA2 Mutations and the Risk for Colorectal Cancer," Clinical Genetics, vol. 87, Iss. 5, pp. 411-418.
Springman et al. (1995). "Zinc content and function in human fibroblast collagenase," Biochemistry. 34( 48): 15713-15720.

Steck et al. (1943). "Reactions of Phenanthraquinone and Retenequinone with Aldehydes and Ammonium Acetate in Acetic Acid Solution." J. Am. Chem. Soc. 65: 452-456.
Sternberg. (1994). "The Emerging Fungal Threat." Science. 266: 1632-1634.
Subramaniam et al. (1998). "Tissue, cell type, and breast cancer stage-specific expression of a TGF-β inducible early transcription factor gene." J. Cell Biochem. 68(2): 226-236.
Tallman et al. (1997) "All-trans-retinoic acid in acute promyelocytic leukemia". N. Engl. J. Med. 337(15): 1021-1028.
Tanaseichuk et al. (1971). "Nitrogen-Containing Heterocyclic Free Radicals. VI. N-Methylindolyldiphenylimidazoles." Uch. Zap., Mord. Univ., No. 81, 95-97 (From: Ref. Zh., Khim. 1972, Abstr. No. 12zh318 D (and English Chemical Abstract No. 43368).
Tanaseichuk et al. (1971). "Study of Nitrogen-Containing Heterocyclic Free Radicals. Part V. Synthesis of 2-(N-Methylindolyl-3)-4(5)-Phenyl-5(4) *p*-Phenyl-Substituted Imidazoles." Uch. Zap. Mord. Univ. 81: 95-97.
Tardi et al. (1996). "Iposomal doxorubicin," J. Drug Targeting, vol. 4(3), pp. 129-140.
Thaler et al. (1988). "Evaluation of Single-Drug and Combination Antifungal Therapy in an Experimental Model of Candidiasis in Rabbits with Prolonged Neutropenia." The Journal of Infectious Diseases 158(1): 80-88.
Torchilin et al. (2003). "Immunomicelles: Targeted pharmaceutical carriers for poorly soluble drugs," Proc. Natl. Acad. Sci., USA, vol. 100, pp. 6039-6044.
Totsuka et al. (1999). "Combined effects of vancomycin and imipenem against methicillin-resistant *Staphylococcus au reus* (MRSA) in vitro and in vivo." Journal of Antimicrobial Chemotherapy. 44: 455-460.
Tsai et al. (2018). "APTO-253 Is a New Addition to the Repertoire of Drugs that Can Exploit DNA BRCA1/2 Deficiency," Small Molecule Therapeutics, vol. 17, Iss. 6, pp. 1167-1170.
Tutt et al. (2002). "The relationship between the roles of BRCA genes in DNA repair and cancer predisposition." Trends Mol Med. 8(12): 571-6.
Vanhaesebroeck et al. (1999). "Signaling by distinct classes of phosphoinositide 3-kinases," Exp. Cell Res., vol. 253(1), pp. 239-254.
Vassilev et al. (2001). "Cell-based screening approach for antitumor drug leads which exploits sensitivity differences between normal and cancer cells: identification of two novel cell-cycle inhibitors," Anti-Cancer Drug Design, vol. 16, pp. 7-17.
Walsh et al. (1990). "Effects of Preventive, Early, and Late Antifungal Chemotherapy with Fluconazole in Different Granulocytopenic Models of Experimental Disseminated Candidiasis." The Journal of Infectious Diseases. 161: 755-760.
Wang et al. (2012). "siRNA targeting of Cdx2 inhibits growth of human gastric cancer MGC-803 cells." World J Gastroenterol. 18(16): 1903-1914.
Wang et al. (2002). "Down-regulation of gut-enriched Krüppel-like factor expression in esophageal cancer." World J. Gastroenterol. 8(6): 966-970.
Wei et al. (2005). "Drastic Down-regulation of Krüppel-Like Factor 4 Expression Is Critical in Human Gastric Cancer Development and Progression." Cancer Research. 65(7): 2746-2754.
Weissig et al. (1998). "Accumulation of protein-loaded long-circulating micelles and liposomes in subcutaneous Lewis lung carcinoma in mice," Phar. Res., vol. 15(10), pp. 1552-1556.
Wermuth et al. (1998). The Practice of Medicinal Chemistry, Academic Press, 243-248.
Wermuth et al. (1998). Technomics Corporation, 1, p. 243-248 (Japanese Version)—(Corresponding to C.G. Wermuth, The Practice of Medicinal Chemistry, Molecular Variations Based on Isosteric Replacements, 1996, 203-237, Academic Press (English version).
West et al (1992). "Simple Assays of Retinoid Activity as Potential Screens for Compounds That May Be Useful in Treatment of Psoriasis," J. Investigative Derm., vol. 99, pp. 95-100.
Wicking et al. (1998). "CDX2, a human homologue of *Drosophila caudal*, is mutated in both alleles in a replication error positive colorectal cancer." Oncogene. 17(5): 657-659.

(56) References Cited

OTHER PUBLICATIONS

Wood et al. (2007). "The Genomic Landscapes of Human Breast and Colorectal Cancers." Science. 318(5853): 11081113.
Written Opinion dated May 24, 2004 for International Application No. PCT/CA2003/01229, 6 pages.
Written Opinion for International Application No. PCT/IB2006/051675, dated Jan. 3, 2007, 5 pages.
Written Opinion issued by the International Searching Authority for PCT Application No. PCT/US2014/059140, dated Dec. 31, 2014, 7 pages.
Written Opinion issued by the International Searching Authority for PCT Application No. PCT/US2014/059142, dated Dec. 31, 2014, 7 pages.
Written Opinion dated Feb. 7, 2019 for International Application No. PCT/US2018/058103, 7 pages.
Xiong et al. (1999). "Interaction of polypyridyl ruthenium(II) complexes containing non-planar ligands with DNA." J. Chem. Soc., Dalton Trans. pp. 19-23.
Xiu et al. (1996). "A Novel Approach to Synthesis of Tricyanovinylthiophene for heterocyclic Imidazole Nonlinear OpticalChromophores." Tetrahedron Letters. 37(41): 7331-7334.
Xu et al. (2003). "Effects of the ancillary ligands of polypyridyl ruthenium (ii) complex(es) on the DNA-binding behaviors," New J. Chem. 27: 1255-1263.
Xu et al. (2003). "Synthesis and spectroscopic RNA binding studies of [Ru(phen)2MHPIP]2+." Inorg. Chem. Commun., vol. 6, pp. 766-768.
Xu et al. (2003). "Effects of ligand planarity on the interaction of polypyridyl Ru(II) complexes with DNA," J. Royal Society of Chemistry., Dalton Trans., vol. 11, pp. 2260-2268.
Yagi et al. (1999). "Genomic structure and alterations of homeobox gene CDX2 in colorectal carcinomas." Br. J. Cancer. 79(3-4): 440-444.
Yamada et al. (1990). "Synthesis of 2,9-Dichloro-1, 10-phenanthroline from N,N'-Annelated Phenanthrolinediones," Bull. Soc. Chem. Jpn., vol. 63(9), pp. 2710-2712.
Yamamoto et al. (2001). "Long-circulating poly(ethylene glycol)-poly(D,L-lactide) block copolymer micelles with modulated surface charge," J. Controlled Release, vol. 77, pp. 27-38.
Yanke et al. (2000). "A CD-1 mouse model of infection with *Staphylococcus aureus*: Influence of gender on infection with MRSA and MSSA isolates." Canada Journal of Microbiology. 46: 920-926.
Yasunaga et al. (2004). "Identification of Aberrantly Methylated Genes in Association with Adult T-Cell Leukemia." Cancer Res. 64(17): 6002-6009.
Yegorov et al. (1993). "Simultaneous Determination of Fe(III) and Fe(II) in Water Solutions and Tissue Homogenates Using Desferal and 1,10-Phenanthrolin," Free Radic. Biol. Med., vol. 15. pp. 565-574.
Yokoyama et al. (1998). "Characterization of physical entrapment and chemical conjugation of adriamycin in polymeric micelles and their design for in vivo delivery to a solid tumor," J. of Controlled Release, vol. 50, pp. 79-92.
Yoon et al. (2003). "Krüppel-like Factor 4 Mediates p53-dependent G1/S Cell Cycle Arrest in Response to DNA Damage." J Biol Chem. 278(4): 2101-2105.
Zalewski et al. (1993). "Correlation of apoptosis with change in intracellular labile Zn(II) using Zinquin [(2-methyl-8-p-toluenesulphonamido-6-quinolyloxy)acetic acid], a new specific fluorescent probe for Zn(II)," Biochem. J., vol. 296(Pt. 2), pp. 403-408.
Zeytinoglu et al. (2003). "Mutagenicity Assay in Salmonella for Thirteen 2-Substituted-JH-phenanthro (9,10-d) Imidazoles", Drug and Chemical Toxicology. 26(4): 245-257.
Zhang. (1996). "Bacterial signaling involving eukaryotic-type protein kinases," Mol. Microb., vol. 20(1), pp. 9-15.
Zhang et al. (2000). "2,4,5-Trisumstituted Imidazoles: Novel Nontoxic Modulators of P-glycoprotein Mediated Multidrug Resistance. Part 2." Bioorganic & Medicinal Chemistry Letters. 10: 2603-2605.
Zhang et al. (2000). "The gut-enriched Krüppel-like factor (Krüppel-like factor 4) mediates the trans activating effect of p53 on the p21 WAF1/Cip 1 promoter," J. Biol. Chem., vol. 275 (24), pp. 18391-18398.
Zhang et al (2003). "Design of New Polypyridyl Ligands and Their Effects on DNA binding Mechanisms of Complexes," Chemical Journal of Chinese Universities, vol. 24(10)(2003) pp. 1753-1755 (Article and Abstract).
Zhang et al. (2005). "Development and characterization of a novel Cremophor® EL free liposome-based paclitaxel (LEP-ETU) formulation," Eur. J. Pharm. Biophar., vol. 59, pp. 177-187.
Zhang et al. (2016). "Inhibition of c-Myc by APT0-253 as an Innovative Therapeutic Approach to Induce Cell Cycle Arrest and Apoptosis in Acute Myeloid Leukemia," 58th American Society of Hematology Annual Meeting and Exposition, San Diego, CA, pp. 1 of 1.
Zhao et al. (2004). "Identification of Krüppel-like factor 4 as a potential tumor suppressor gene in colorectal cancer," Oncogene, vol. 23(2), pp. 395-402.
Zhao et al. (2004). "Role of zinc and iron chelation in apoptosis mediated by tachpyridine, an anti-cancer iron chelator." Biochemical Pharmacology. 67(9): 1677-1688.
Zhuang et al. (2003). Synthesis and character of two new NI-phenanthroline fluorescence probe for nucleic acid determination, College of Environment Science and Engineering, Huaxue Shiji, vol. 25(6), pp. 325-328 (with English Abstract).
ClinicalTrials.gov Identifier: NCT01432145, A Clinical Trial in Patients With Breast Cancer Susceptibility Gene (BRCA) Defective Tumours (6MP), First Posted—Sep. 12, 2011, Last Update Posted—Jul. 9, 2019, retrieved from https://clinicaltrials.gov/ct2/show/results/NCT01432145, 11 pages.
De Luca et al., "BRCA1 Loss Induces GADD153-Mediated Doxorubicin Resistance in Prostate Cancer," Mol Cancer Res. Aug. 2011; 9(8): 1078-1090.
Roberts et al., "Results of a phase II clinical trial of 6-mercaptopurine (6MP) and methotrexate in patients with BRCA-defective tumours," British Journal of Cancer (2020) 122:483-490.

* cited by examiner (a) — intracellular Compound 1 after treatment with Compound 1
(b) — intracellular Fe(CMPD I)₃ after treatment with Compound 1
(c) — intracellular Compound 1 after treatment with Fe(CMPD I)₃
(d) — intracellular Fe(CMPD I)₃ after treatment with Fe(CMPD I)₃

(a) – intracellular Compound 1 in Raji
(b) – intracellular Fe(CMPD I)$_3$ in Raji
(c) – intracellular Compound 1 in Raji/CMPD I R
(d) – intracellular Fe(CMPD I)$_3$ in Raji/CMPD I R

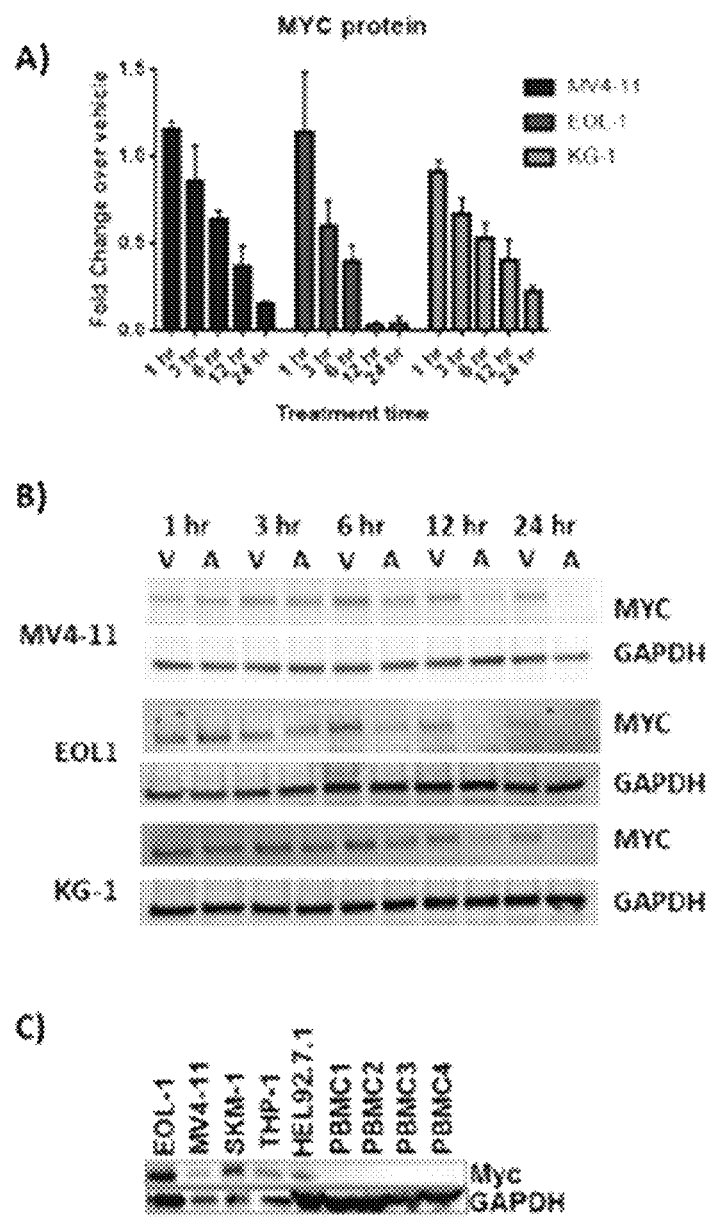

D)

E)

F)

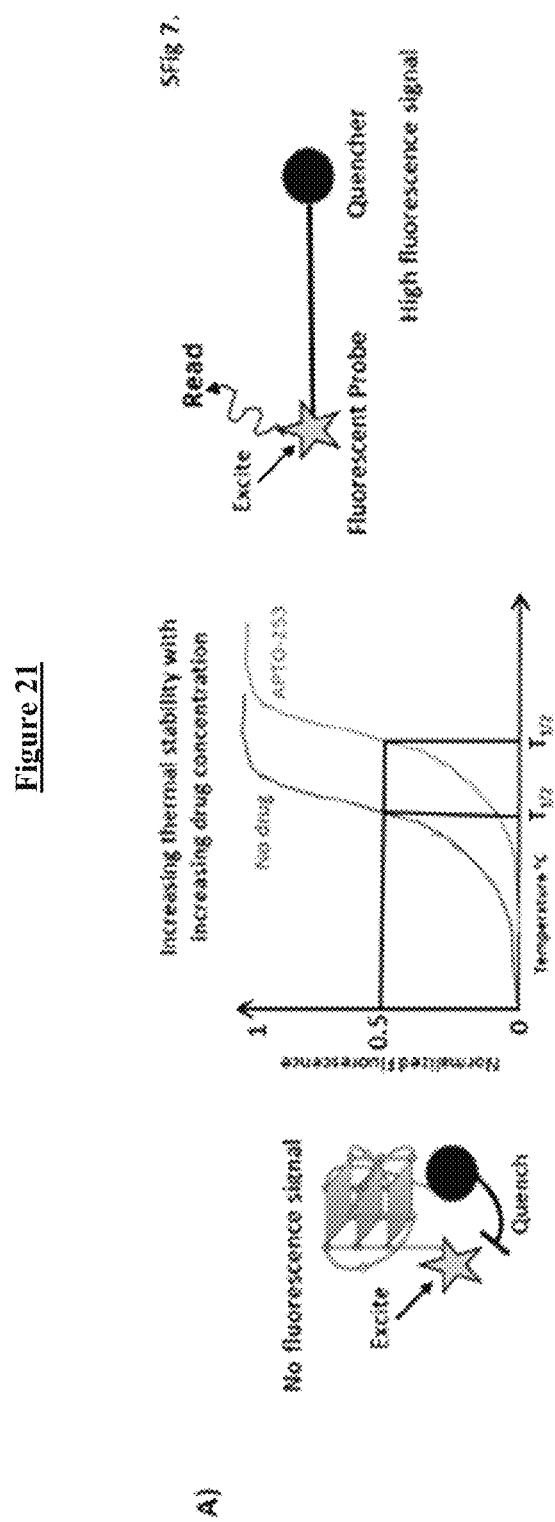

```
                          SEQUENCE LISTING

<160> NUMBER OF SEQ ID NOS: 15

<210> SEQ ID NO 1
<211> LENGTH: 19
<212> TYPE: DNA
<213> ORGANISM: Artificial Sequence
<220> FEATURE:
<223> OTHER INFORMATION: ABCG2 oligonucleotide primer

<400> SEQUENCE: 1
ttaggattga agccaaagg                                                  19

<210> SEQ ID NO 2
<211> LENGTH: 21
<212> TYPE: DNA
<213> ORGANISM: Artificial Sequence
<220> FEATURE:
<223> OTHER INFORMATION: ABCG2 oligonucleotide primer

<400> SEQUENCE: 2
taggcaattg tgaggaaaat a                                               21

<210> SEQ ID NO 3
<211> LENGTH: 20
<212> TYPE: DNA
<213> ORGANISM: Artificial Sequence
<220> FEATURE:
<223> OTHER INFORMATION: MYC oligonucleotide primer

<400> SEQUENCE: 3
gagcagcagc gaaagggaga                                                 20

<210> SEQ ID NO 4
<211> LENGTH: 20
<212> TYPE: DNA
<213> ORGANISM: Artificial Sequence
<220> FEATURE:
<223> OTHER INFORMATION: MYC oligonucleotide primer

<400> SEQUENCE: 4
cagccgagca ctctagctct                                                 20

<210> SEQ ID NO 5
<211> LENGTH: 19
<212> TYPE: DNA
<213> ORGANISM: Artificial Sequence
<220> FEATURE:
<223> OTHER INFORMATION: MYC oligonucleotide primer

<400> SEQUENCE: 5
```

```
ccgcatccac gaaactttg                                          19

<210> SEQ ID NO 6
<211> LENGTH: 23
<212> TYPE: DNA
<213> ORGANISM: Artificial Sequence
<220> FEATURE:
<223> OTHER INFORMATION: MYC oligonucleotide primer

<400> SEQUENCE: 6
gggtgttgta agttccagtg caa                                     23

<210> SEQ ID NO 7
<211> LENGTH: 27
<212> TYPE: DNA
<213> ORGANISM: Artificial Sequence
<220> FEATURE:
<223> OTHER INFORMATION: 28s RNA oligonucleotide primer

<400> SEQUENCE: 7
agtagcaaat attcaaacga gaacttt                                 27

<210> SEQ ID NO 8
<211> LENGTH: 21
<212> TYPE: DNA
<213> ORGANISM: Artificial Sequence
<220> FEATURE:
<223> OTHER INFORMATION: 28s RNA oligonucleotide primer

<400> SEQUENCE: 8
acccatgttc aactgctgtt c                                       21

<210> SEQ ID NO 9
<211> LENGTH: 20
<212> TYPE: DNA
<213> ORGANISM: Artificial Sequence
<220> FEATURE:
<223> OTHER INFORMATION: MYC oligonucleotide primer

<400> SEQUENCE: 9
cagtagaaat acggctgcac                                         20

<210> SEQ ID NO 10
<211> LENGTH: 20
<212> TYPE: DNA
<213> ORGANISM: Artificial Sequence
<220> FEATURE:
<223> OTHER INFORMATION: MYC oligonucleotide primer

<400> SEQUENCE: 10
ttcgggtagt ggaaaaccag                                         20

<210> SEQ ID NO 11
<211> LENGTH: 33
<212> TYPE: DNA
<213> ORGANISM: Artificial Sequence
<220> FEATURE:
<223> OTHER INFORMATION: G-quadruplex Telomere oligonucleotide
<220> FEATURE:
<221> NAME/KEY: misc_feature
<222> LOCATION: (1)..(1)
<223> OTHER INFORMATION: FAM (fluorescein) fluorescent dye covalently
      attached
<220> FEATURE:
<221> NAME/KEY: misc_feature
<222> LOCATION: (33)..(33)
<223> OTHER INFORMATION: BHQ1 (Black Hole Quencher 1) non-fluorescent
```

-continued chromophore covalently attached

<400> SEQUENCE: 11
gggttagggt tagggttagg gttagggtta ggg                                33

<210> SEQ ID NO 12
<211> LENGTH: 29
<212> TYPE: DNA
<213> ORGANISM: Artificial Sequence
<220> FEATURE:
<223> OTHER INFORMATION: G-quadruplex MYC oligonucleotide
<220> FEATURE:
<221> NAME/KEY: misc_feature
<222> LOCATION: (1)..(1)
<223> OTHER INFORMATION: FAM (fluorescein) fluorescent dye covalently
      attached
<220> FEATURE:
<221> NAME/KEY: misc_feature
<222> LOCATION: (29)..(29)
<223> OTHER INFORMATION: BHQ1 (Black Hole Quencher 1) non-fluorescent
      chromophore covalently attached

<400> SEQUENCE: 12 ccatgggag ggtggagggt ggggaaggt                                      29

<210> SEQ ID NO 13
<211> LENGTH: 33
<212> TYPE: DNA
<213> ORGANISM: Artificial Sequence
<220> FEATURE:
<223> OTHER INFORMATION: G-quadruplex KIT oligonucleotide
<220> FEATURE:
<221> NAME/KEY: misc_feature
<222> LOCATION: (1)..(1)
<223> OTHER INFORMATION: FAM (fluorescein) fluorescent dye covalently
      attached
<220> FEATURE:
<221> NAME/KEY: misc_feature
<222> LOCATION: (33)..(33)
<223> OTHER INFORMATION: BHQ1 (Black Hole Quencher 1) non-fluorescent
      chromophore covalently attached

<400> SEQUENCE: 13
ttatagggag ggcgctggga ggagggagga gac                                33

<210> SEQ ID NO 14
<211> LENGTH: 33
<212> TYPE: DNA
<213> ORGANISM: Artificial Sequence
<220> FEATURE:
<223> OTHER INFORMATION: G-quadruplex rRNA oligonucleotide
<220> FEATURE:
<221> NAME/KEY: misc_feature
<222> LOCATION: (1)..(1)
<223> OTHER INFORMATION: FAM (fluorescein) fluorescent dye covalently
      attached
<220> FEATURE:
<221> NAME/KEY: misc_feature
<222> LOCATION: (33)..(33)
<223> OTHER INFORMATION: BHQ1 (Black Hole Quencher 1) non-fluorescent
    chromophore
      covalently attached

<400> SEQUENCE: 14
aataagggtg gcgggggta gaggggggta ata                                 33

<210> SEQ ID NO 15
<211> LENGTH: 20
<212> TYPE: DNA
<213> ORGANISM: Artificial Sequence
<220> FEATURE:

```
<223> OTHER INFORMATION: G-quadruplex ds_DNA oligonucleotide
<220> FEATURE:
<221> NAME/KEY: misc_feature
<222> LOCATION: (1)..(1)
<223> OTHER INFORMATION: FAM (fluorescein) fluorescent dye covalently
      attached
<220> FEATURE:
<221> NAME/KEY: misc_feature
<222> LOCATION: (10)..(11)
<223> OTHER INFORMATION: linked by Spacer 18 which is a hexaethylene
      glycol chain that is 18 atoms long
<220> FEATURE:
<221> NAME/KEY: misc_feature
<222> LOCATION: (20)..(20)
<223> OTHER INFORMATION: BHQ1 (Black Hole Quencher 1) non-fluorescent
      chromophore covalently attached

<400> SEQUENCE: 15
tatagctata tatagctata                                              20
```

ARYL IMIDAZOLES FOR TREATMENT OF CANCER

CROSS REFERENCE TO RELATED APPLICATIONS

This application claims the benefit of U.S. Provisional Application No. 62/578,938, filed on Oct. 30, 2017, the contents of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LOTH_057_01US_SeqList_ST25, date recorded: Nov. 29, 2018, file size ~4.63 kilobytes).

FIELD OF THE INVENTION

The present invention generally relates to a method of preventing, reducing, or treating cancer in a subject.

BACKGROUND

Proteins encoded by the breast cancer susceptibility genes (BRCA proteins) have been associated with a predisposition to breast, ovarian and other cancers. These proteins are ubiquitously expressed thereby implicating them in many processes fundamental to all cells including DNA repair and recombination, checkpoint control of cell cycle and transcription.

Specifically, genetic susceptibility to breast cancer has been linked to mutations of certain genes (e.g., BRCA-1 and BRCA-2). Proteins encoded by these genes are believed to work to preserve chromosome structure, but their precise role is unclear due to them being involved in a multitude of processes. It is postulated that a mutation causes a disruption in the protein which causes chromosomal instability in BRCA deficient cells thereby predisposing them to neoplastic transformation.

About 10% of breast cancer cases cluster in families, some due to mutations in the BRCA-1 and BRCA-2 genes, giving rise to higher cancer risk. Mutations in other genes linked to tumor suppression may account for cancer predisposition. These include mutations in p53 tumor suppression, the STK11/LKB, protein kinase or the PTEN phosphatase.

Deficits in homologous recombination in tumors provide the opportunity for selective killing of tumor cells; however, the drugs currently used to exploit this opportunity cause serious myelosuppression which limits dose. Therefore, there is still an unmet need of high priority in the art to identify drugs for which loss of BRCA1 or BRCA2 function results in hypersensitivity but that do not cause myelosuppression.

SUMMARY OF THE INVENTION

The present disclosure is related to a method of preventing, reducing, or treating cancer in a subject.

In an embodiment, the present disclosure relates to a method of preventing, reducing, or treating cancer in a subject, comprising administering a therapeutically effective amount of compound I,

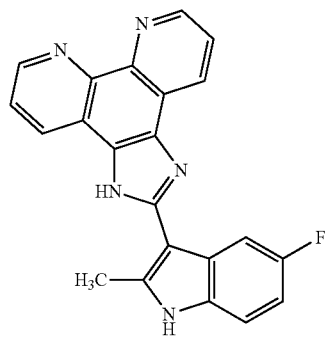 [SMILES: Cc1[nH]c2ccc(F)cc2c1-c1nc2c3cccnc3c3ncccc3c2[nH]1]

or a pharmaceutically acceptable salt, free base, hydrate, complex, or chelate (including metal chelates, such as iron, zinc and others) thereof to the subject, wherein the subject has a mutation in a DNA repair gene. In certain embodiments, the DNA repair gene is a homologous recombinant gene. For example, the DNA repair gene is a gene in the homologous recombination (HR) dependent deoxyribonucleic acid (DNA) double strand break (DSB) repair pathway. In some embodiments, the DNA repair gene is one or more genes selected from the group consisting of BRCA-1, BRCA-2, ATM, ATR, CHK1, CHK2, Rad51, RPA and XRCC3. For example, the DNA repair gene is BRCA-1 and/or BRCA-2. In an embodiment, the subject is human.

In an embodiment, the subject is heterozygous for a mutation in a DNA repair gene. In certain embodiments, the subject is heterozygous for a mutation in a gene in the homologous recombination (HR) dependent deoxyribonucleic acid (DNA) double strand break (DSB) repair pathway. In one embodiment, the subject is heterozygous for a mutation in BRCA1 or BRCA2. In another embodiment, the subject is homozygous for a mutation in BRCA1 or BRCA2.

In an embodiment, the cancer is selected from the group consisting of a hematologic cancer, colorectal cancer, ovarian cancer, breast cancer, cervical cancer, lung cancer, liver cancer, pancreatic cancer, cancer of the lymph nodes, leukemia, renal cancer, colon cancer, prostate cancer, brain cancer, cancer of the head and neck, bone cancer, carcinoma of the larynx and oral cavity, Ewing's sarcoma, skin cancer, kidney cancer, and cancer of the heart. In certain embodiments, the cancer is selected from the group consisting of breast cancer, lung cancer, ovarian cancer, cancer of the lymph nodes, colon cancer, leukemia, renal cancer, and prostate cancer. In one embodiment, the cancer is breast cancer.

In some embodiments, the cancer is a hematological malignancy. Examples of hematological malignancies include, but are not limited to, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), eosinophilic leukemia, mantle cell lymphoma, myelodysplastic syndromes (MDSs) (e.g. high-risk MDS), myeloproliferative disorders (MPD), and multiple myeloma (MM). In some embodiments, the cancer is acute myeloid leukemia. In some embodiments, the cancer is chronic myeloid leukemia. In some embodiments, the cancer is a lymphoma. In some embodiments, the cancer is high-risk myelodysplastic syndrome.

In an embodiment, the cancer is a BRCA-associated cancer. In certain embodiments, the BRCA-associated cancer has one or more mutations of the BRCA-1 and/or BRCA-2 genes.

In an embodiment, the method of the present disclosure further comprises the administering of a therapeutically effective amount of a second therapeutically active agent. The second therapeutically active agent is administered before, during, or after the subject has been administered

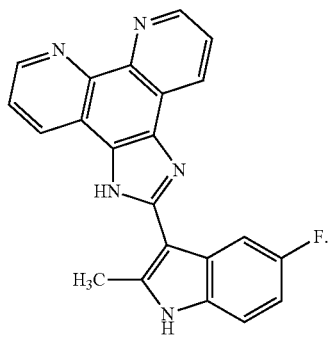 [SMILES: Cc1[nH]c2ccc(F)cc2c1-c1nc2c3cccnc3c3ncccc3c2[nH]1]

The second therapeutically active agent is selected from one or more of the group consisting of immunotherapeutic agents, anticancer agents, and angiogenic agents. In one embodiment, the second therapeutically active agent is a PARP inhibitor. For example, the PARP inhibitor is olaparib.

In an embodiment, the subject experiences less than a 90% decrease in bone marrow activity relative to a subject who was not administered a therapeutically effective amount of

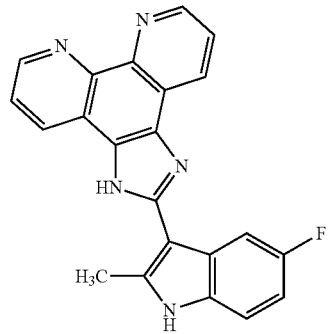 [SMILES: Cc1[nH]c2ccc(F)cc2c1-c1nc2c3cccnc3c3ncccc3c2[nH]1]

or a pharmaceutically acceptable salt, free base, hydrate, complex, or chelate (including metal chelates, such as iron, zinc and others) thereof. For example, the subject may experience less than a 10% decrease in bone marrow activity or no decrease in bone marrow activity.

In an embodiment, the subject already has cancer. In certain embodiments, the subject already having cancer experiences a reduction or decrease in size of a tumor associated with a cancer. For example, the subject experiences complete elimination of the tumor associated with cancer. In certain embodiments, the subject already having cancer experiences an inhibition, decrease, or reduction of neo-vascularization or angiogenesis in a tumor associated with a cancer.

In another embodiment, the present disclosure relates to a method for killing cancer cells, comprising contacting said cells with a therapeutically effective amount of

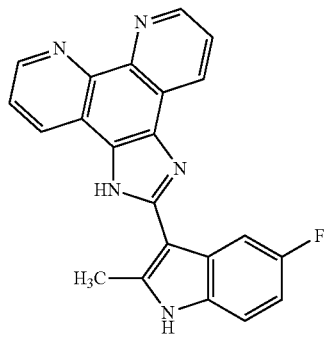 [SMILES: Cc1[nH]c2ccc(F)cc2c1-c1nc2c3cccnc3c3ncccc3c2[nH]1]

or a pharmaceutically acceptable salt, free base, hydrate, complex, or chelate (including metal chelates, such as iron, zinc and others) thereof. In one embodiment, the cancer cells have a deficiency in one or more genes selected from the group consisting of BRCA-1, BRCA-2, ATM, ATR, CHK1, CHK2, Rad51, RPA and XRCC3.

In another embodiment, the present disclosure relates to a method for inducing cell cycle arrest in cancer cells, comprising contacting said cells with a therapeutically effective amount of cells thereby predisposing them to neoplastic transformation.

In another embodiment, the present disclosure relates to a method of preventing, reducing or treating cancer in a subject, comprising administering a therapeutically effective amount of one or more molecules of

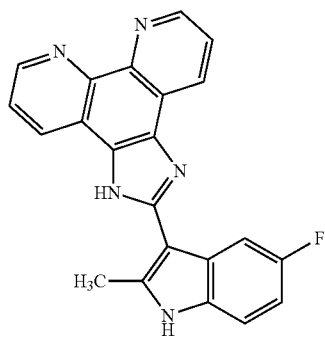 [SMILES: Cc1[nH]c2ccc(F)cc2c1-c1nc2c3cccnc3c3ncccc3c2[nH]1]

in complex with one or more metal atoms, wherein the subject has a mutation in a DNA repair gene. In one embodiment, the one or more metal atoms are selected from the group consisting of iron, zinc, aluminum, magnesium, platinum, silver, gold, chromium, nickel, titanium, copper, scandium, zirconium, vanadium, molybdenum, manganese, tungsten and cobalt. In one embodiment, the one or more metal atoms are iron. In certain embodiments, the complex has the following structure:

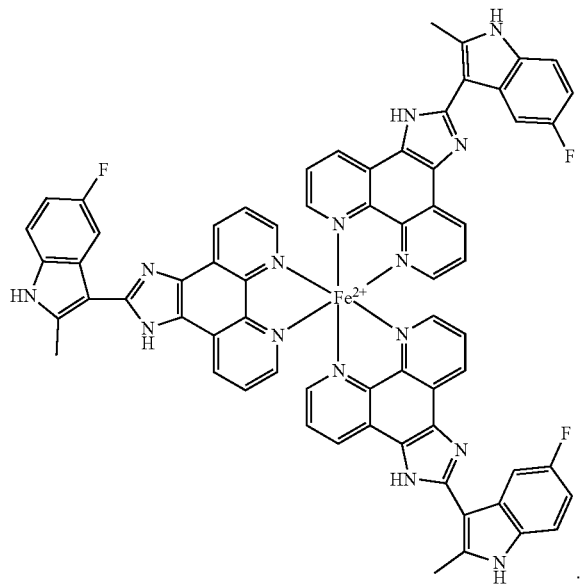

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION

Figure 1:
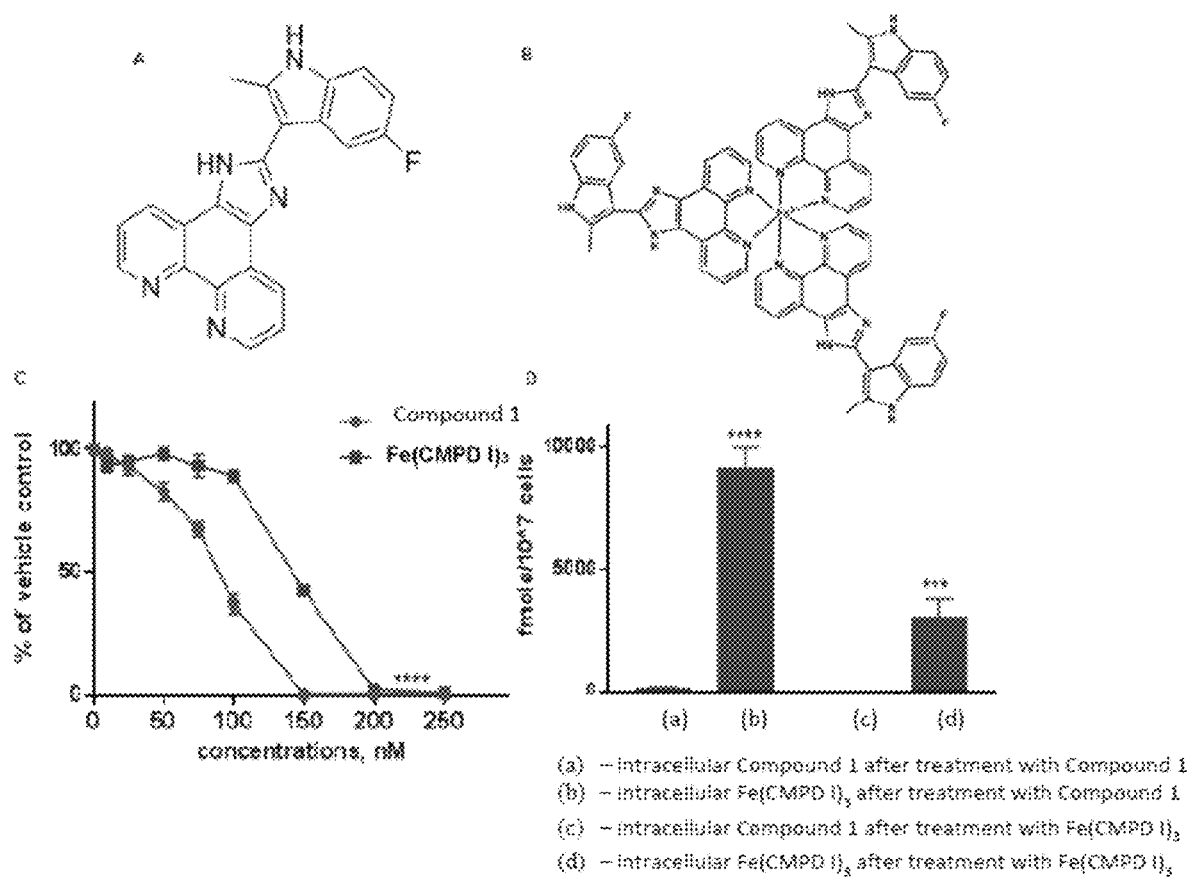
FIG. 1 shows that Fe(COMPOUND I)$_3$ is an active intracellular form of COMPOUND I. (A) Structure of COMPOUND I. (B) Structure of Fe(COMPOUND I)$_3$. (C) Relative cytotoxicity of COMPOUND I (■) and Fe(COMPOUND I)$_3$ (●) in the Raji cells. (D) The intracellular accumulation of COMPOUND I (■) and Fe(COMPOUND I)$_3$ (■) in Raji cells exposed to 0.5 μM COMPOUND I or Fe(COMPOUND I)$_3$ for 6 h. Vertical bars, ±SEM; where missing SEM is less than the size of the symbol; *, P<0.001; **, p<0.0001.

In view of the foregoing challenges relating to the identification of drugs for which loss of BRCA1 or BRCA2 function results in cellular hypersensitivity but that do not cause myelosuppression in an individual, COMPOUND I has been identified. It was unexpectedly discovered that COMPOUND I causes DNA damage, and cells deficient in homologous recombination are as hypersensitive to this drug as they are to olaparib, which is an FDA-approved PARP inhibitor. COMPOUND I joins the limited repertoire of drugs which can exploit defects in homologous recombination while not causing myelosuppression.

Mechanistic studies on the mechanisms of action and resistance to COMPOUND I were also undertaken, so as to identify synthetic lethal interactions that can guide combination drug studies. As described herein, COMPOUND I is converted intracellularly into an Fe complex (Fe(COMPOUND I)$_3$) which is an active form of the drug. COMPOUND I generated DNA damage at early time points as documented by γH2AX accumulation and foci formation. BRCA1- and BRCA2-deficient cells were found to be hypersensitive to COMPOUND I to a degree comparable to that of olaparib. Resistance to COMPOUND I in Raji cells is associated with up-regulation of the efflux transporter ABCG2 and resistance is partially reversed by ABCG2 inhibition. The ability of COMPOUND I to exploit homologous recombination deficiency is of particular interest because, unlike all the other drugs for which loss of this repair function results in hypersensitivity, COMPOUND I does not produce myelosuppression even at the maximum tolerated dose.

COMPOUND I is of interest because it is a member of a novel class of compounds that exhibits potent cytotoxicity against a wide range of both solid tumor and hematologic malignancies and does not cause myelosuppression. The key findings reported herein are that the COMPOUND I monomer can be converted intracellularly to an active complex containing a ferrous Fe atom and three molecules of COMPOUND I, whose intracellular concentration may exceed that of the native drug. COMPOUND I and/or its complex with iron causes DNA damage, in which the DNA repair requires the function of both BRCA1 and BRCA2 as evidenced by synthetic lethality with COMPOUND I. In the case of Raji lymphoma cells, acquired resistance is associated with reduced drug uptake and marked over-expression of the ABCG2 drug efflux pump whose inhibition partially reverses resistance.

Compared with many other chemotherapeutic agents used to treat lymphoma, the cellular accumulation of COMPOUND I is relatively slow, but it appears to be rapidly converted to Fe(COMPOUND I)$_3$ as this complex is present as soon as the native form of the drug is detected in the cell. By 6 h the cellular content of the Fe(COMPOUND I)$_3$ exceeded that of the native form by ~18-fold. The potency of the Fe(COMPOUND I)$_3$ complex is only 2-fold less than that of native drug which can be accounted for by the fact that, while COMPOUND I is neutral, Fe(COMPOUND I)$_3$ is much larger and contains a $2^+$ charge which would be expected to impair transmembrane influx. The fact that no native drug was detectable in cells incubated with the Fe(COMPOUND I)$_3$ complex strongly suggests that Fe(COMPOUND I)$_3$ is an active intracellular form of the drug. Drugs containing the 2,10 indole ring structure are known to chelate Fe and Zn. In the case of COMPOUND I, while the Fe chelate was abundant in cells, a Zn chelate was not detectable. Indeed, the Fe chelate levels were high enough that cells exposed to COMPOUND I became pink in color. The high level of Fe(COMPOUND I)$_3$ raises the question of whether its formation depletes cells of Fe to the point where cellular metabolism is impaired and this remains an interesting point for further investigation. Without being bound by any particular theory, chelation may be facilitated by the intracellular environment, as no extracellular Fe(COMPOUND I)$_3$ was detected when COMPOUND I was incubated with complete tissue culture medium.

The observation that deficiency in homologous recombination produced by loss of BRCA1/2 function results in hypersensitivity to certain types of DNA damaging drugs has been exploited to increase the effectiveness of the platinum-containing drugs cisplatin and carboplatin, and the PARP inhibitors olaparib and niraparib particularly in the case of ovarian cancer. Ledermann et al., "Olaparib Maintenance Therapy in Platinum-Sensitive Relapsed Ovarian Cancer," *N. Engl. J. Med.*, 2012; 366 (15):1382-92; Mirza et al., "Niraparib Maintenance Therapy in Platinum-Sensitive, Recurrent Ovarian Cancer," *N. Engl. J. Med.*, 2016; 375 (22):2154-64, both of which are incorporated by reference. Various degrees of homologous recombination deficiency have been identified at lower frequency in a variety of other tumors. Davies et al., "HRDetect is a Predictor of BRCA1 and BRCA2 Deficiency Based on Mutational Signatures," *Nat. Med.* 2017; 23 (4):517-525, which is hereby incorporated by reference. The ability of COMPOUND I to exploit homologous recombination deficiency is of particular interest because, unlike all the other drugs for which loss of this repair function results in hypersensitivity, COMPOUND I does not produce myelosuppression even at the maximum tolerated dose. Cercek et al., "Phase 1 study of COMPOUND I HCl, an Inducer of KLF4, in Patients with Advanced or Metastatic Solid Tumors," *Invest. New Drugs*, 2015; 33 (5):1086-92, which is hereby incorporated by reference. Thus, COMPOUND I joins the limited repertoire of drugs which can take advantage of this important therapeutic window. The observations reported herein identify γ-H2AX as a potential biomarker of clinical drug effect and point the way toward more detailed studies of how COMPOUND I causes DNA damage. Ivashkevich et al., "Use of the Gamma-H2AX Assay to Monitor DNA Damage and Repair in Translational cancer Research," *Cancer Lett,* 2012; 327 (1-2):123-33, which is hereby incorporated by reference.

Development of acquired resistance to COMPOUND I in the Raji lymphoma cells was associated with reduced accumulation of COMPOUND I and the Fe(COMPOUND I)$_3$ complex. There was 16.5±1.94 fold more intracellular Fe(COMPOUND I)$_3$ in the Raji sensitive cells than the resistant cells which corresponds perfectly to the relative resistance of the Raji/COMPOUND IR over the sensitive cells (16.7±3.9 fold). RNA-seq analysis of the Raji/COMPOUND IR cells pointed most directly to over-expression of ABCG2 as a possible mechanism of resistance. Western blot analysis confirmed up-regulation at the protein level, and that ABCG2 was functional and directly involved in COMPOUND I resistance was established by the ability of its inhibitor to partially reverse resistance to COMPOUND I as well as topotecan. The fact that accumulation of Fe(COMPOUND I)$_3$ was reduced in the resistant cells incubated with the pre-formed complex suggests that the Fe(COMPOUND I)$_3$ as well as the native drug may be a substrate for the ABCG2 transporter. None of the known classes of drugs for which increased ABCG2 confers resistance have obvious structural similarity to COMPOUND I or Fe(COMPOUND I)$_3$. Thus, the discovery that ABCG2 can mediate resistance to COMPOUND I expands the range of known substrates for this important transporter. Whether ABCG2 can be used as a biomarker for sensitivity to COMPOUND I will need to be explored in a large panel of cell lines. A search of the Connectivity Map (https://portals.broadinstitute.org/cmap/) did not disclose any significant similarity between the cytotoxicity pattern of COMPOUND I and any of the other drugs thus far tested in the large panel of cell lines further highlighting the uniqueness of this compound.

Given that the specific inhibitor of ABCG2, Ko143, did not completely reverse acquired COMPOUND I resistance, it seems likely that other mechanisms also contribute to the phenotype. In this regard, the cross-resistance to carboplatin is of particular interest. Carboplatin is not a known ABCG2 substrate, but it too causes DNA damage and up-regulation of transcription-coupled repair has been widely reported to contribute to resistance to both carboplatin and cisplatin, both of which produce the same types of adducts in DNA. Enoiu et al., "Repair of Cisplatin-induced DNA Interstrand Crosslinks by a Replication-independent Pathway Involving Transcription-coupled Repair and Translesion Synthesis," *Nucleic Acids Res.* 2012; 40 (18):8953-64, which is hereby incorporated by reference. It remains to be determined whether up-regulation of DNA repair capacity contributes to both carboplatin and COMPOUND I resistance.

Also described herein, it was discovered that COMPOUND I is associated with CDKN1A upregulation and MYC downregulation, followed by $G_0$-$G_1$ cell-cycle arrest and apoptosis in AML cells. Moreover, inhibition of MYC, a well-recognized pivotal oncogene in AML, correlated with the cytotoxicity of COMPOUND I. Differential expression analysis suggested the involvement of DNA damage, including induction of γ-H2AX accumulation, and cellular stress pathways after COMPOUND I treatment. Prior cellular pharmacokinetic studies demonstrated that COMPOUND I is transformed from a monomeric form to a ferrous complex [Fe(COMPOUND I)$_3$] in cells, and that this complex is the principal intracellular form of the drug. In this study, we demonstrate that the parental COMPOUND I and the Fe(COMPOUND I)$_3$ complex bind to and stabilize G-quadruplex (G4) motifs. The Fe(COMPOUND I)$_3$ complex stabilized G4 motifs found in the promoters of key oncogenes (e.g., MYC, KIT), as well as in rRNA genes and telomeres. This stabilization of secondary DNA structures was specific for G4 motifs, as the parental COMPOUND I and Fe(COMPOUND I)$_3$ did not interact with dsDNA. Treatment of MV4-11 AML cells with preformed Fe(COMPOUND I)$_3$ also inhibits MYC expression and induces CDKN1A expression along with induction of apoptotic and DNA damage pathways. Together, the results support the conclusion that the effect of COMPOUND I on the expression of MYC and its downstream target genes, on cell-cycle arrest, and on DNA damage and stress responses can be linked to the action of COMPOUND I and the Fe(COMPOUND I)$_3$ on G-quadruplex DNA motifs.

Definitions

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range can be an endpoint for the range encompassed thereby (e.g., the range 50-80 includes the ranges with endpoints such as 55-80, 50-75, etc.).

COMPOUND I refers to 2-(5-fluoro-2-methyl-1H-indol-3-yl)-1H-imidazo[4,5-f][1,10]phenanthroline, pharmaceutically acceptable salts, esters, prodrugs, hydrates, solvates and isomers thereof, for the structure below.

COMPOUND I

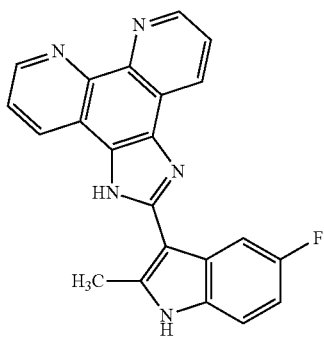 [SMILES: Cc1[nH]c2ccc(F)cc2c1-c1nc2c3cccnc3c3ncccc3c2[nH]1]

Fe(COMPOUND I)₃ refers to the following structure:

Fe(COMPOUND I)₃

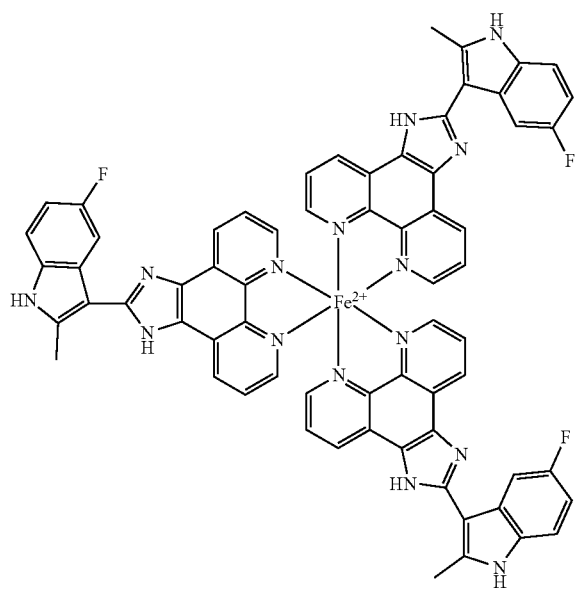

A "pharmaceutically acceptable salt" includes both acid and base addition salts.

A pharmaceutically acceptable salt of COMPOUND I may be a "pharmaceutically acceptable acid addition salt" derived from inorganic or organic acid, and such salt may be pharmaceutically acceptable nontoxic acid addition salt containing anion. For example, the salt may include acid addition salts formed by inorganic acids such as hydrochloric acid, sulfuric acid, nitric acid, phosphoric acid, hydrobromic acid, hydroiodic acid, and the like; organic carbonic acids such as tartaric acid, formic acid, citric acid, acetic acid, trichloroacetic acid, trifluoroacetic acid, gluconic acid, benzoic acid, lactic acid, fumaric acid, maleic acid, and the like; and sulfonic acids such as methanesulfonic acid, benzenesulfonic acid, p-toluenesulfonic acid, naphthalensulfonic acid, and the like.

The pharmaceutically acceptable salt of COMPOUND I may be prepared by conventional methods well-known in the art. Specifically, the "pharmaceutically acceptable salt" in accordance with the present invention may be prepared by, e.g., dissolving COMPOUND I in a water-miscible organic solvent such as acetone, methanol, ethanol or acetonitrile and the like; adding an excessive amount of organic acid or an aqueous solution of inorganic acid thereto; precipitating or crystallizing the mixture thus obtained. Further, it may be prepared by further evaporating the solvent or excessive acid therefrom; and then drying the mixture or filtering the extract by using, e.g., a suction filter.

The term "chelate" as used herein means a molecular entity made up of a central metal associated with at least one bidentate ligand and optionally associated with one or more mono- or multi-dentate ligands. For example, a "chelate" as used means a molecular entity made up of a central metal associated with at least one bidentate ligand of COMPOUND I. In the interaction between the central metal and any of the ligands, the bonds between the ligand and the central metal can include covalent bonds, ionic bonds, and/or coordinate covalent bonds.

The term "complex" or "metal complex" as used herein means a coordination complex of a metal and a ligand. For example, a "complex" or "metal complex" as used herein means a coordination complex of a metal and COMPOUND I.

The term "metal" as used herein means any alkaline, alkaline earth, transition, rare earth, basic, and semi-metals which can coordinate with a ligand. Representative metals include the transition metals, lanthanide, and actinide metals. In some embodiments, the metal has d-orbitals capable of interacting with a ligand. For example, the metal may be iron, zinc, aluminum, magnesium, platinum, silver, gold, chromium, nickel, titanium, copper, scandium, zirconium, vanadium, molybdenum, manganese, tungsten and cobalt. In one embodiment, the metal is iron.

The term "ester" as used herein refers to a chemical moiety having chemical structure of —$(R)_n$—COOR', wherein R and R' are each independently selected from the group consisting of alkyl, cycloalkyl, aryl, heteroaryl (connected to oxygen atom by aromatic ring) and heteroalicyclic (connected by aromatic ring), and n is 0 or 1, unless otherwise indicated.

The term "prodrug" as used herein refers to a precursor compound that will undergo metabolic activation in vivo to produce the parent drug. Prodrugs are often useful because they can be easily administered as compared to parent drugs thereof in some cases. For instance, some prodrugs are bioavailable via oral administration unlike parent drugs thereof often show poor bioavailability. Further, the prodrugs may show improved solubility in the pharmaceutical composition as compared to parent drugs thereof. For instance, COMPOUND I may be administered in the form of an ester prodrug so as to increase drug delivery efficiency since the solubility of a drug can adversely affect the permeability across the cell membrane. Then, once the compound in the form of the ester prodrug enters a target cell, it may be metabolically hydrolyzed into a carboxylic acid and an active entity.

Hydrates or solvates of COMPOUND I are included within the scope of the present invention. As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. The solvent can be water, in which case the solvate can be a hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating particularly pharmaceutically acceptable solvents.

The compounds of the disclosure or their pharmaceutically acceptable salts can contain one or more axes of chirality such that atropisomerization is possible. Atropisomers are stereoisomers arising because of hindered rotation about a single bond, where energy differences due to steric strain or other contributors create a barrier to rotation that is high enough to allow for isolation of individual conformers. The present disclosure is meant to include all such possible isomers, as well as their racemic and optically pure forms whether or not they are specifically depicted herein. Optically active isomers can be prepared using chiral synthons or chiral reagents, or resolved using conventional techniques, for example, chromatography and fractional crystallization. Conventional techniques for the preparation/isolation of individual atropisomers include chiral synthesis from a suitable optically pure precursor or resolution of the racemate (or the racemate of a salt or derivative) using, for example, chiral high pressure liquid chromatography (HPLC).

A "stereoisomer" refers to a compound made up of the same atoms bonded by the same bonds but having different three-dimensional structures, which are not interchangeable. The present invention contemplates various stereoisomers and mixtures thereof as it pertains to atropisomerism.

The terms "treat", "treating" or "treatment" in reference to a particular disease or disorder includes prevention of the disease or disorder, and/or lessening, improving, ameliorating or abrogating the symptoms and/or pathology of the disease or disorder. Generally, the terms as used herein refer to ameliorating, alleviating, lessening, and removing symptoms of a disease or condition. COMPOUND I herein may be in a therapeutically effective amount in a formulation or medicament, which is an amount that can lead to a biological effect, such as DNA damage, apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor).

When treatment as described above refers to prevention of a disease, disorder, or condition, said treatment is termed prophylactic. Administration of said prophylactic agent can occur prior to the manifestation of symptoms characteristic of a proliferative disorder, such that a disease or disorder is prevented or, alternatively, delayed in its progression.

As used herein, the terms "inhibiting" or "reducing" cell proliferation is meant to slow down, to decrease, or, for example, to stop the amount of cell proliferation, as measured using methods known to those of ordinary skill in the art, by, for example, 10%, 20%, 30%, 40%, 50%, 60%, 70%, 80%, 90%, 95%, or 100%, when compared to proliferating cells that are not subjected to the methods, compositions, and combinations of the present application.

As used herein, "cell cycle arrest" refers to the halting of a series of events that take place in the cell leading to its division and replication, which may be caused by a number of factors, including, but not limited to, DNA damage, X-radiation, ionizing radiation, and chemotherapeutic agents. In certain embodiments, "DNA damage" and "cell cycle arrest" are used interchangeably.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

As used herein, "myelosuppression" refers to the suppression of one or more components of hematopoiesis, which manifests in aberrant levels of one or more of the cell types that are the products of this process. For a review of hematopoiesis, and characteristics of hematopoietic cells, see *Clinical Immunology: Principles and Practice*, Vol. 1, Ch. 2, pp. 15-24 (Lewis and Harriman, eds. Mosby—Year Book, Inc. 1996), which pages are hereby incorporated by reference. On a general level, it refers to decreases in white blood cell and/or platelet counts. It also refers, on a more specific level, to suppression, relative to normal levels, of one or more of the following cells that result from hematopoiesis: B-cells, T-cells, natural killer cells, dendritic cells, macrophages, neutrophils, eosinophils, basophils, mast cells and platelets. Other terms may be used interchangeably with myelosuppression and will be readily apparent to a skilled artisan. Non-limiting examples of such terms include "bone marrow suppression," "myelotoxicity," and myeloablation." On the other hand, therefore, "myelorecovery" is the opposite of myelosuppression. Therefore, in one embodiment, the term "bone marrow activity" refers to the levels of the following cells that result from hematopoiesis: B-cells, T-cells, natural killer cells, dendritic cells, macrophages, neutrophils, eosinophils, basophils, mast cells platelets, erythrocytes, platelets, myeloid and lymphoid white blood cells and others that are apparent to a skilled artisan.

The term "subject" as used herein, refers to an animal, such as a mammal or non-mammal. For example, the subject may be a mammal, such as a human, who is in the need of treatment or prevention of cancer. The term subject may be interchangeably used with the term patient in the context of the present invention.

"Mammal" includes humans and both domestic animals such as laboratory animals and household pets (e.g., cats, dogs, swine, cattle, sheep, goats, horses, rabbits), and non-domestic animals such as wildlife and the like. The term "patient" or "subject" as used herein, includes humans and animals.

"Non-mammal" includes a lion-mammalian invertebrate and non-mammalian vertebrae, such as a bird (e.g., a chicken or duck) or a fish.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"An "effective amount" refers to a therapeutically effective amount or a prophylactically effective amount. A "therapeutically effective amount" refers to an amount effective, at dosages and for periods of time necessary, to achieve the desired therapeutic result, such as cancer cell death, reduced tumor size, increased life span or increased life expectancy. A therapeutically effective amount of a compound can vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors or slower cell proliferation. Typically, a prophylactic dose is used in subjects prior to or at an earlier stage of disease, so that a prophylactically effective amount can be less than a therapeutically effective amount.

Methods

The present invention provides methods of preventing, reducing, or treating cancer in a subject.

In one embodiment of the present disclosure, a method is provided for preventing, reducing, or treating cancer in a subject, comprising administering a therapeutically effective amount of

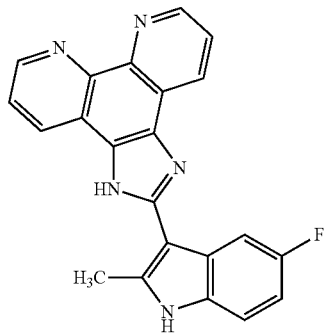 [SMILES: Cc1[nH]c2ccc(F)cc2c1-c1nc2c3cccnc3c3ncccc3c2[nH]1]

(COMPOUND I) or a pharmaceutically acceptable salt, free base, hydrate, complex, or chelate (including metal chelates, such as iron, zinc and others) thereof to the subject, wherein the subject has a mutation in a DNA repair gene. In an embodiment, the subject is a human. In another embodiment, the subject already has cancer.

In another embodiment, the present disclosure relates to a method of preventing, reducing or treating cancer in a subject, comprising administering a therapeutically effective amount of one or more molecules of COMPOUND I in complex with one or more metal atoms, wherein the subject has a mutation in a DNA repair gene. In one embodiment, the one or more metal atoms are selected from the group consisting of iron, zinc, aluminum, magnesium, platinum, silver, gold, chromium, nickel, titanium, copper, scandium, zirconium, vanadium, molybdenum, manganese, tungsten and cobalt. In one embodiment, the one or more metal atoms are iron. In certain embodiments, the complex has the following structure:

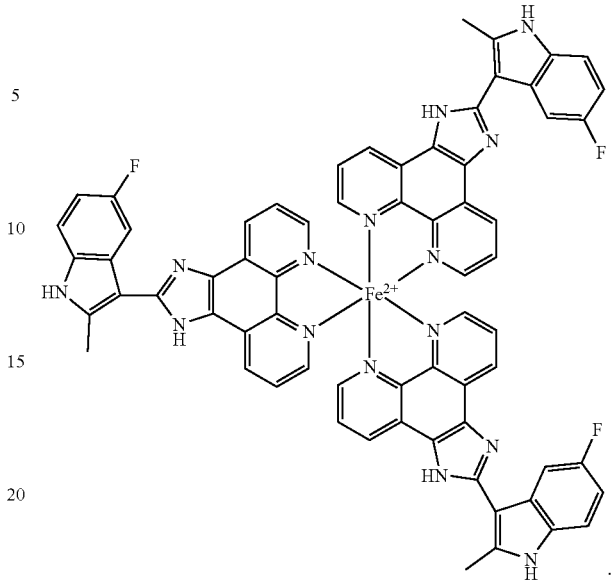

In an embodiment, the DNA repair gene is a homologous recombinant gene. In certain embodiments, the DNA repair gene is a gene in the homologous recombination (HR) dependent deoxyribonucleic acid (DNA) double strand break (DSB) repair pathway. A skilled artisan will appreciate that the HR dependent DNA DSB repair pathway repairs double-strand breaks (DSBs) in DNA via homologous mechanisms to reform a continuous DNA helix. K. K. Khanna and S. P. Jackson, Nat. Genet. 27(3): 247-254 (2001), which is hereby incorporated by reference in its entirety. The components of the HR dependent DNA DSB repair pathway include, but are not limited to, ATM, ATR, CHK1, CHK2, RPA, RAD51, RAD51L1, RAD51C, RAD51L3, DMC1, XRCC2, XRCC3, RAD52, RAD54L, RAD54B, BRCA1, BRCA2, RAD50, MRE11A and NBS1. Other proteins involved in the HR dependent DNA DSB repair pathway include regulatory factors such as EMSY. Hughes-Davies et al, Cell, Vol 115, pp 523-535, which is hereby incorporated by reference in its entirety. Thus, in certain embodiments, the DNA repair gene is one or more genes selected from the group consisting of BRCA-1, BRCA-2, ATM, ATR, CHK1, CHK2, Rad51, RPA, and XRCC3. In certain embodiments, the DNA repair gene is BRCA-1 and/or BRCA-2.

In an embodiment of the present disclosure, the subject is heterozygous for a mutation in a DNA repair gene. In certain embodiments, the subject is heterozygous for a mutation in a gene in the homologous recombination (HR) dependent deoxyribonucleic acid (DNA) double strand break (DSB) repair pathway. Thus, in certain embodiments, the gene in the homologous recombination (HR) dependent deoxyribonucleic acid (DNA) double strand break (DSB) repair pathway is one or more genes selected from the group consisting of BRCA-1, BRCA-2, ATM, ATR, CHK1, CHK2, Rad51, RPA and XRCC3. In certain embodiments, the DNA repair gene is BRCA-1 and/or BRCA-2.

In an embodiment of the present disclosure, the subject is homozygous for a mutation in a DNA repair gene. In certain embodiments, the subject is homozygous for a mutation in a gene in the homologous recombination (HR) dependent deoxyribonucleic acid (DNA) double strand break (DSB) repair pathway. Thus, in certain embodiments, the gene in the homologous recombination (HR) dependent deoxyribonucleic acid (DNA) double strand break (DSB) repair pathway is one or more genes selected from the group consisting of BRCA-1, BRCA-2, ATM, ATR, CHK1, CHK2, Rad51, RPA and XRCC3. In certain embodiments, the DNA repair gene is BRCA-1 and/or BRCA-2.

In an embodiment, the subject is administered a therapeutically effective amount of COMPOUND I, or a pharmaceutically acceptable salt, free base, hydrate, complex, or chelate (including metal chelates, such as iron, zinc and others) thereof for the treatment or prevention of cancer. A skilled artisan will appreciate that within the context of the present disclosure, a variety of cancers may be treated or prevented. Thus, in an embodiment, the cancer is selected from the group consisting of heme cancer, colorectal cancer, ovarian cancer, breast cancer, cervical cancer, lung cancer, liver cancer, pancreatic cancer, cancer of the lymph nodes, leukemia, renal cancer, colon cancer, prostate cancer, brain cancer, cancer of the head and neck, bone cancer, carcinoma of the larynx and oral cavity, Ewing's sarcoma, skin cancer, kidney cancer, and cancer of the heart. In certain embodiments, the cancer is selected from the group consisting of breast cancer, lung cancer, cancer of the lymph nodes, colon cancer, leukemia, renal cancer, and prostate cancer. In one embodiment, the cancer is breast cancer. In some embodiments, the cancer is a hematological malignancy. Examples of hematological malignancies include, but are not limited to, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), eosinophilic leukemia, mantle cell lymphoma, myelodysplastic syndromes (MDSs) (e.g. high-risk MDS), myeloproliferative disorders (MPD), and multiple myeloma (MM). In some embodiments, the cancer is acute myeloid leukemia. In some embodiments, the cancer is chronic myeloid leukemia. In some embodiments, the cancer is a lymphoma. In some embodiments, the cancer is high-risk myelodysplastic syndrome.

In an embodiment, the subject is administered a therapeutically effective amount of COMPOUND I, or a pharmaceutically acceptable salt, free base, hydrate, complex, or chelate (including metal chelates, such as iron, zinc and others) thereof for the treatment or prevention of a BRCA-associated cancer. A skilled artisan will appreciate that a variety of cancers are associated with BRCA. In an embodiment, the BRCA-associated cancer has one or more mutations of the BRCA-1 and/or BRCA-2 genes.

The cancer cells may have a phenotype which is characteristic of a deficiency in a component of HR dependent DNA DSB repair pathway i.e. activity of a component of the pathway is reduced or abolished in the cancer cells. Cancer cells with such a phenotype may be deficient in a component of the pathway, for example a component listed above i.e. expression and/or activity of the component may be reduced or abolished in the cancer cells, for example by means of mutation, polymorphism or epigenetic modification, such as hypermethylation, in the encoding nucleic acid or in a gene encoding a regulatory factor.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2 i.e. expression and/or activity of BRCA1 and/or BRCA2 may be reduced or abolished in the cancer cells, for example by means of mutation, polymorphism or epigenetic modification, such as hypermethylation, in the encoding nucleic acid or in a gene encoding a regulatory factor, for example the EMSY gene which encodes a BRCA2 regulatory factor (Hughes-Davies et al, Cell, Vol 115, pp 523-535, which is hereby incorporated by reference).

BRCA1 and BRCA2 are known tumor suppressors whose wild-type alleles are frequently lost in tumors of heterozygous carriers (Jasin M. Oncogene. 2002 Dec. 16; 21(58): 8981-93; Tutt et al Trends Mol Med. (2002)8(12):571-6). The association of BRCA1 and/or BRCA2 mutations with breast cancer is well-characterized in the art (Radice P J Exp Clin Cancer Res. 2002 September; 21 (3 Suppl):9-12, which is hereby incorporated by reference). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In other preferred embodiments, the cancer cells may have an ATM, ATR, CHK1, CHK2, Rad51, DSS1, RPA and/or XRCC3 deficient phenotype i.e. the activity of one or more of these components is reduced or abolished in the cancer cells. Cancer cells may, for example, be deficient in ATM, ATR, CHK1, CHK2, Rad51, DSS1, RPA and/or XRCC3 i.e. expression and/or activity of ATM, ATR, CHK1, CHK2, Rad51, DSS1, RPA and/or XRCC3 may be reduced or abolished in the cancer cells, for example by means of mutation, polymorphism or epigenetic modification, such as hypermethylation, in the encoding nucleic acid or in a gene encoding a regulatory factor.

In an embodiment, the subject having a mutated DNA-repair gene that is administered a therapeutically effective amount of COMPOUND I, or a pharmaceutically acceptable salt, free base, hydrate, complex, or chelate (including metal chelates, such as iron, zinc and others) thereof is an animal. In certain embodiments, the subject is a mammal. Thus, the subject within the context of the present disclosure may be human, domestic animals (e.g., laboratory animals), household pets (e.g., cats, dogs, swine, cattle, sheep, goats, horses, rabbits), and non-domestic animals such as wildlife and the like. In one embodiment, the subject is a human.

Myelosuppression

In an embodiment, the method of the present disclosure is directed to administering a therapeutically effective amount of COMPOUND I, or a pharmaceutically acceptable salt, free base, hydrate, complex, or chelate thereof to a subject, wherein the incidence of myelosuppression in said subject is prevented or lowered relative to a subject who was not administered a therapeutically effective amount of COMPOUND I. In certain embodiments, the subject who was not administered a therapeutically effective amount of COMPOUND I has been administered a chemotherapeutic agent that is not COMPOUND I for the treatment or prevention of cancer. Thus, in one embodiment, the method of the present disclosure is directed to administering a therapeutically effective amount of COMPOUND I, or a pharmaceutically acceptable salt, free base, hydrate, complex, or chelate (including metal chelates, such as iron, zinc and others) thereof to a subject, wherein the incidence of myelosuppression in said subject is prevented or lowered relative to a subject who has been administered a chemotherapeutic agent that is not COMPOUND I. As used herein, myelosuppression generally refers to the suppression of one or more components of hematopoiesis (e.g., bone marrow activity), which manifests in aberrant levels of one or more of the cell types that are the products of this process. The suppression of one or more components of hematopoiesis (e.g., bone marrow activity) may refer to, for example, the suppression of white blood cell counts and/or platelet counts. Accordingly, in an embodiment, a method of the present disclosure is provided for preventing, reducing, or treating cancer in a subject, comprising administering a therapeutically effective amount of COMPOUND I or a pharmaceutically acceptable salt, free base, hydrate, complex, or chelate (including metal chelates, such as iron, zinc and others) thereof to the subject, wherein the subject has a mutation in a DNA repair gene and wherein the subject experiences less than a 90% decrease in bone marrow activity relative to a subject who was not administered a therapeutically effective amount of COMPOUND I. For instance, the subject experiences less than a 90%, 85%, 80%, 75%, 70%, 65%, 60%, 55%, 50%, 45%, 40%, 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25% decrease in bone marrow activity relative to a subject who was not administered a therapeutically effective amount of COMPOUND I. In an embodiment, the subject administered a therapeutically effective amount of COMPOUND I experiences less than a 10% decrease in bone marrow activity relative to a subject who was not administered a therapeutically effective amount of COMPOUND I. In an embodiment, the subject administered a therapeutically effective amount of COMPOUND I experiences no decrease in bone marrow activity relative to a subject who was not administered a therapeutically effective amount of COMPOUND I.

In an embodiment, a method is provided for treating cancer in a subject, comprising administering a therapeutically effective amount of COMPOUND I, or a pharmaceutically acceptable salt, free base, hydrate, complex, or chelate (including metal chelates, such as iron, zinc and others) thereof to the subject, wherein the subject has a mutation in a DNA repair gene. In certain embodiments, various pathological conditions associated with cancer, and which are readily apparent to a skilled artisan, may be treated in a subject having cancer by administering a therapeutically effective amount of COMPOUND I or a pharmaceutically acceptable salt, free base, hydrate, complex, or chelate (including metal chelates, such as iron, zinc and others) thereof. Accordingly, in one embodiment, the subject experiences a reduction or decrease in size of a tumor associated with a cancer. The reduction or decrease in tumor size may be anywhere from about a 1% reduction or decrease in tumor size to about a 100% reduction or decrease in tumor size, including all integers and ranges therebetween. For instance, the reduction or decrease in tumor size may be about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In one embodiment, the subject experiences complete elimination of the tumor associated with cancer (i.e., 100% reduction or decrease in tumor size). In another embodiment, the subject experiences inhibition, decrease, or reduction of neo-vascularization or angiogenesis in a tumor associated with a cancer. The decrease or reduction of neo-vascularization or angiogenesis in a tumor associated with a cancer may be anywhere from about a 1% reduction or decrease in neo-vascularization or angiogenesis to about a 100% reduction or decrease in neo-vascularization or angiogenesis, including all integers and ranges therebetween. For instance, the reduction or decrease in neo-vascularization or angiogenesis may be about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In one embodiment, the subject experiences complete reduction or decrease in neo-vascularization or angiogenesis associated with cancer (i.e., 100% reduction or decrease in neo-vascularization or angiogenesis).

In one embodiment, the present disclosure is directed to a method for killing cancer cells, comprising contacting said cells with a therapeutically effective amount of COMPOUND I, or a pharmaceutically acceptable salt, free base, hydrate, complex, or chelate (including metal chelates, such as iron, zinc and others) thereof. In certain embodiments, the cancer cells have a deficiency in one or more genes selected from the group consisting of BRCA-1, BRCA-2, ATM, ATR, CHK1, CHK2, Rad51, RPA and XRCC3.

In one embodiment, the present disclosure relates to a method for inducing cell cycle arrest in cancer cells, comprising contacting said cells with a therapeutically effective amount of

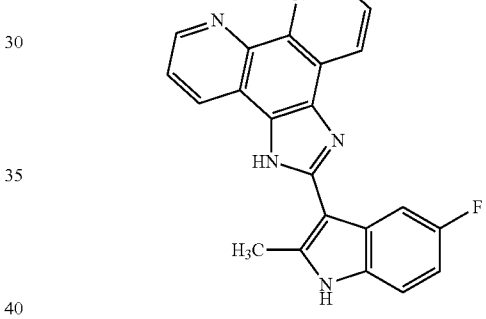

or a pharmaceutically acceptable salt, free base, hydrate, complex, or chelate (including metal chelates, such as iron, zinc and others) thereof. In certain embodiments, the cancer cells have a deficiency in one or more genes selected from the group consisting of BRCA-1, BRCA-2, ATM, ATR, CHK1, CHK2, Rad51, RPA and XRCC3.

In one embodiment, a method for stabilizing G-quadruplexes (G4s) in a subject is provided where the method comprises administering to the subject a therapeutically effective amount of COMPOUND I, or a pharmaceutically acceptable salt, free base, hydrate, complex, or chelate (including metal chelates, such as iron, zinc and others) thereof. In another embodiment, a method for stabilizing G-quadruplexes (G4s) in a subject is provided where the method comprises administering to the subject a therapeutically effective amount of a pharmaceutical combination comprising COMPOUND I, or a pharmaceutically acceptable salt, free base, hydrate, complex, or chelate (including metal chelates, such as iron, zinc and others) thereof, and at least one additional therapeutically active agent, as described herein. In some embodiments, a method for stabilizing G-quadruplexes (G4s) in a subject is provided where the method comprises administering to the subject a therapeutically effective amount of a pharmaceutical combination comprising COMPOUND I, or a pharmaceutically acceptable salt, free base, hydrate, complex, or chelate (including metal chelates, such as iron, zinc and others) thereof, and administering radiotherapy or at least one additional therapeutically active agent before, during, or after the subject has been administered the aforementioned compound.

In one embodiment, COMPOUND I, or a pharmaceutically acceptable salt, free base, hydrate, complex, or chelate (including metal chelates, such as iron, zinc and others) thereof, is administered at a dose from about 1 mg/day to about 3 g/day. In certain embodiments, COMPOUND I, or a pharmaceutically acceptable salt, free base, hydrate, complex, or chelate (including metal chelates, such as iron, zinc and others) thereof, is administered at a dose from about 1 mg/day to about 200 mg/day. In certain embodiments, COMPOUND I, or a pharmaceutically acceptable salt, free base, hydrate, complex, or chelate (including metal chelates, such as iron, zinc and others) thereof, is administered at a dose from about 50 mg/day to about 200 mg/day.

Combination Therapy

In one embodiment, the present invention provides a combination therapy comprising COMPOUND I with at least one additional therapeutically active agent.

In one embodiment, the present invention provides a method of treating a condition associated with cell proliferation in a patient in need thereof. In one embodiment, the present invention provides a method of treating cancer or tumors. The method comprises co-administering to a patient in need thereof a therapeutically effective amount of COMPOUND I, or a pharmaceutically acceptable salt, free base, hydrate, ester, solvate and/or prodrug thereof and at least one additional therapeutically active agent. In one embodiments, at least one additional therapeutically active agent is Olaparib.

The term "co-administration" or "coadministration" refers to administration of (a) COMPOUND I, or a pharmaceutically acceptable salt, free base, hydrate, complex, or chelate (including metal chelates, such as iron, zinc and others) thereof and (b) at least one additional therapeutically active agent, together in a coordinated fashion. For example, the co-administration can be simultaneous administration, sequential administration, overlapping administration, interval administration, continuous administration, or a combination thereof. In one embodiment, COMPOUND I, or a pharmaceutically acceptable salt, free base, hydrate, complex, or chelate (including metal chelates, such as iron, zinc and others) thereof and at least one additional therapeutically active agent are formulated into a single dosage form. In another embodiment, COMPOUND I, or a pharmaceutically acceptable salt, free base, hydrate, complex, or chelate (including metal chelates, such as iron, zinc and others) thereof and at least one additional therapeutically active agent are provided in a separate dosage forms.

Pharmaceutical Formulations

In another embodiment, the present invention provides a pharmaceutical composition and/or combination comprising a therapeutically effective amount of COMPOUND I or a pharmaceutically acceptable salt, free base, hydrate, complex, or chelate (including metal chelates, such as iron, zinc and others) thereof, as disclosed herein, as the active ingredient, combined with a pharmaceutically acceptable excipient or carrier. The excipients are added to the formulation for a variety of purposes.

In some embodiments, COMPOUND I or a pharmaceutically acceptable salt, free base, hydrate, complex, or chelate (including metal chelates, such as iron, zinc and others) thereof and at least one therapeutically active agent may be formulated into a single pharmaceutical composition and/or combination. In some embodiments, COMPOUND I or a pharmaceutically acceptable salt, free base, hydrate, complex, or chelate (including metal chelates, such as iron, zinc and others) thereof and at least one therapeutically active agent are formulated into a separate pharmaceutical composition and/or combination comprising a pharmaceutically acceptable excipient or a carrier.

In a specific embodiment, COMPOUND I or a pharmaceutically acceptable salt, free base, hydrate, complex, or chelate (including metal chelates, such as iron, zinc and others) thereof and at least one therapeutically active agent may be formulated into a single pharmaceutical composition and/or combination composition. In another embodiment, the composition may comprise COMPOUND I or a pharmaceutically acceptable salt, free base, hydrate, complex, or chelate (including metal chelates, such as iron, zinc and others) thereof, as disclosed herein, in an amount of about 1 mg to about 1 g. In another embodiment, the amount is about 5 mg to about 500 mg. In another embodiment, the amount is about 20 mg to about 400 mg. In another embodiment, the amount is about 50 mg to about 300 mg. In another embodiment, the amount is about 100 mg to about 200 mg. In another embodiment, the compound is a salt, ester, solvate or prodrug of COMPOUND I.

In another embodiment, the pharmaceutical composition may comprise a concentration of COMPOUND I or a pharmaceutically acceptable salt, free base, hydrate, complex, or chelate (including metal chelates, such as iron, zinc and others) thereof at about 0.1 mg/ml to about 10 mg/ml. In another embodiment, the concentration is about 0.5 mg/ml to about 5 mg/ml. In another embodiment, the concentration is about 0.75 mg/ml to about 4.5 mg/ml. In another embodiment, the concentration is about at 3 mg/ml to about 5 mg/ml.

In another embodiment, the compound is a salt, ester, solvate or prodrug of COMPOUND I. In another embodiment, the composition may comprise COMPOUND I, or a pharmaceutically acceptable salt, free base, hydrate, ester, solvate and/or prodrug thereof, and a PARP inhibitor. In another embodiment, the PARP inhibitor is Olaparib.

In another embodiment, the composition may comprise COMPOUND I, or a pharmaceutically acceptable salt, free base, hydrate, ester, solvate and/or prodrug thereof and Olaparib, wherein the amount of Olaparib in the composition is about 10 mg to about 800 mg. In another embodiment, the amount of Olaparib is about 20 mg to about 600 mg. In another embodiment, the amount of Olaparib is about 100 mg to about 500 mg. In another embodiment, the amount of Olaparib is about 300 mg to about 400 mg.

Pharmaceutical acceptable excipients may be added to the composition/formulation. For example, diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT(r)), potassium chloride, powdered cellulose, sodium chloride, sorbitol, and talc.

Solid pharmaceutical compositions and/or combinations that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition and/or combination in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition and/or combination, the composition and/or combination is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions and/or combinations may also be dyed using any pharmaceutically acceptable colorant to improve their appearance and/or facilitate patient identification of the product and unit dosage level.

In liquid pharmaceutical compositions and/or combinations may be prepared using COMPOUND I, or a pharmaceutically acceptable salt, free base, hydrate, ester, solvate and/or prodrug thereof, of the present invention and any other solid excipients where the components are dissolved or suspended in a liquid carrier such as water, vegetable oil, alcohol, polyethylene glycol, propylene glycol, glycerin, or macrogol 15 hydroxystearate (Solutol).

Liquid pharmaceutical compositions and/or combinations may contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions and/or combinations may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition and/or combination may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions and/or combination of the present invention include powders, granulates, aggregates and compacted compositions and/or combinations. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions, aerosols and elixirs.

The dosage form of the present invention may be a capsule containing the composition and/or combination, preferably a powdered or granulated solid composition and/or combination of the invention, within either a hard or soft shell. The shell may be made from gelatin and optionally contain a plasticizer such as glycerin and sorbitol, and an opacifying agent or colorant.

A composition and/or combination for tableting or capsule filling may be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may be tableted, or other excipients may be added prior to tableting, such as a glidant and/or a lubricant.

A tableting composition and/or combination may be prepared conventionally by dry blending. For example, the blended composition and/or combination of the actives and excipients may be compacted into a slug or a sheet and then comminuted into compacted granules. The compacted granules may subsequently be compressed into a tablet.

As an alternative to dry granulation, a blended composition and/or combination may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting; however, they are not subjected to a final tableting step.

The active ingredient and excipients may be formulated into compositions and/or combinations and dosage forms according to methods known in the art.

In one embodiment, a dosage form may be provided as a kit comprising COMPOUND I, or a pharmaceutically acceptable salt, free base, hydrate, ester, solvate and/or prodrug thereof and pharmaceutically acceptable excipients and carriers as separate components. In one embodiment, a dosage form may be provided as a kit comprising COMPOUND I, or a pharmaceutically acceptable salt, free base, hydrate, ester, solvate and/or prodrug thereof, at least one additional therapeutically active agent, and pharmaceutically acceptable excipients and carriers as separate components. In some embodiments, the dosage form kit allow physicians and patients to formulate an oral solution or injection solution prior to use by dissolving, suspending, or mixing COMPOUND I, or a pharmaceutically acceptable salt, free base, hydrate, ester, solvate and/or prodrug thereof with pharmaceutically acceptable excipients and carriers. In one embodiment, a dosage form kit which provides COMPOUND I, or a pharmaceutically acceptable salt, free base, hydrate, ester, solvate and/or prodrug thereof which has improved stability when compared to pre-formulated formulations of COMPOUND I, or a pharmaceutically acceptable salt, free base, hydrate, ester, solvate and/or prodrug thereof.

In one embodiment, pharmaceutical formulations or compositions and/or combinations of the present invention contain 25-100% or 50-100% by weight of COMPOUND I, or a pharmaceutically acceptable salt, free base, hydrate, ester, solvate and/or prodrug thereof, as described herein, in the formulation or composition and/or combination.

In another embodiment, the methods of the present invention include administering a therapeutically effective amount of Compound I or a pharmaceutically acceptable salt, free base, hydrate, complex, or chelate (including metal chelates, such as iron, zinc and others) thereof in the pharmaceutical formulations or compositions and/or combinations described above. In a specific embodiment, the methods are for preventing, reducing or treating cancer in a subject. In another embodiment, the methods are for killing cancer cells. In another embodiment, the methods are for inducing cell cycle arrest in cancer cells.

The following examples further illustrate the present invention but should not be construed as in any way limiting its scope.

EXAMPLES

Example 1

Materials and Methods for Examples 2-7

Drugs and Reagents

COMPOUND I and deuterated COMPOUND I (COMPOUND I-d6) were provided by APTOSE Biosciences (San Diego, Calif.). Detergent-compatible protein assay kit, DC™ Protein Assay was purchased from BioRad Laboratories, Inc. (Hercules, Calif.). The CellTiter 96® Aqueous One Solution Cell Proliferation Assay (MTS) was were purchased from Promega (Madison, Wis.). PARP, MCL-1, BAD, BIK, $Na^+/K^+$ ATPase antibodies were from Cell Signaling Technology, Inc. (Danvers, Mass.). pSer139 H2AX and ATM antibodies were purchased from Abcam (Cambridge, UK). ABCG2 antibody was obtained from KAMIYA Biomedical (Tukwila, Wash.). Ko143 and was pSer1981-ATM antibody obtained from Millipore Sigma (St. Louis, Mo.). Olaparib was purchased from Selleckchem (Houston, Tex.). Carboplatin and topotecan were obtained from UCSD Moores Cancer Center Pharmacy.

Cell Types and Culture

The human Burkitt lymphoma cell line Raji was obtained from the American Type Tissue Culture Collection and cultured in RPMI 1640 medium (ATCC) supplemented with 10% fetal bovine serum (ATCC,) at 37° C., 5% $CO_2$. The COMPOUND I-resistant Raji (Raji/COMPOUND IR) cell line was generated by exposure to progressively higher concentrations of COMPOUND I over a period of 6 months. CAOV3 cells were obtained from ATCC and cultured in complete DMEM supplemented with 10% fetal bovine serum. MCF7 vector controlled and BRCA1 shRNA subclones were obtained from Dr. Simon Powell (Memorial Sloan-Kettering Cancer Center) and cultured in EMBM with 10% fetal bovine serum. MCF10A and hTERT-IMEC clones were obtained from Dr. Ben Ho Park (Johns Hopkins University). HCT116 $BRCA2^{+/+}$ cells and $BRCA2^{-/-}$ cells were obtained from Dr. Samuel Aparicio (British Columbia Cancer Research Centre). PEO1 and PEO4 cells were obtained from Dr. Sharon Cantor (University of Massachusetts) and these cell lines were cultured under the same conditions as previously published. Sakai et al., Functional restoration of BRCA2 protein by secondary BRCA2 mutations in BRCA2-mutated ovarian carcinoma, *Cancer Res.* 2009; 69 (16):6381-6; Konishi et al., Mutation of a single allele of the cancer susceptibility gene BRCA1 leads to genomic instability in human breast epithelial cells, *Proc. Natl. Acad. Sci.* 2011; 108 (43):17773-8; Xu et al., CX-5461 is a DNA G-quadruplex stabilizer with selective lethality in BRCA1/2 deficient tumours, *Nature Communications* 2017; 8:14432, all of which are hereby incorporated by reference.

Cytotoxicity Study

Cells were plated and treated with the indicated drugs in 96-well plates for 5 days. Cell viability was measured using CellTiter 96 $AQ_{ueous}$ one solution (MTS) cell proliferation assay purchased from Promega, and $IC_{50}$ values were calculated using GraphPad Prism 6 Software.

Biotinylation and Immunoblotting Procedure

To quantify ABCG2 expression, cells were surface-biotinylated with EZ-LINK sulfo-NHS-SS-biotin (Thermo Scientific, Pittsburg, Pa.) and subjected to Western blot analysis as previously reported and subjected to western blot analysis. Tsai C Y, Liebig J K, Tsigelny I F, Howell S B, The copper transporter 1 (CTR1) is required to maintain the stability of copper transporter 2 (CTR2). *Metallomics* 2015; 7:1477-87, which is hereby incorporated by reference.

RNA-seq and qRT-PCR

Total cellular RNA was isolated using the RNeasy mini kit (QIAGEN, Valencia, Calif.) from three independent samples for each experiment. RNA-seq samples were submitted to the IGM Genomics Center, University of California, San Diego, La Jolla, Calif. (http://igm.ucsd.edu/genomics/) for library generation and validation using Agilent Bioanalyzer. Sequencing was performed on Illumina Sequencer HiSeq4000. Bioinformatic Analysis was conducted by OHSU. The forward and reverse primers used for confirmation of ABCG2 over-expression were: 5'-TTA-GGA-TTG-AAG-CCA-AAG-G-3' (SEQ ID NO. 1) and 5'-TAG-GCA-ATT-GTG-AGG-AAA-ATA-3', (SEQ ID NO. 2) respectively.

Cellular Pharmacology of COMPOUND I

Cells exposed to COMPOUND I or Fe(COMPOUND I)$_3$ were homogenized in acetonitrile containing 5 ng of a deuterated COMPOUND I standard. Samples were analyzed at the UCSD Molecular Mass Spectrometry Facility employing an Agilent 1260 liquid chromatograph (LC) system coupled with a Thermo LCQdeca mass spectrometer using positive ion mode electrospray ionization (ESI) as the ion source. The ESI ion source voltage was set at 5 kV, with sheath gas flow rate of 80 units, auxiliary gas flow rate of 20 units, and capillary temperature of 250° C., respectively. A Phenomenex Kinetex Biphenyl column (ID 2.1 mm×length 50 mm, particle size 2.6 μm) was utilized for LC separation using water with 0.1% formic acid as the mobile phase A and acetonitrile with 0.1% formic acid as the mobile phase B. The LC flow rate was set at 0.30 mL/min. The LC gradient increased from 5% mobile phase B to 95% mobile phase B in 10 minutes, held at 95% B for 2 minutes, returned to 5% B in 1 minute, and then held at 5% B for 6 minutes. Under positive ion mode ESI-MS/MS analysis, a major fragmental peak of COMPOUND I was observed at m/z 353 from its molecular ion peak at m/z 368 ([M+H]+) with a normalized collision energy of 45%, and a major fragmental peak of COMPOUND I-d6 at m/z 359 from its molecular ion peak at m/z 374 ([M+H]+) was observed with a normalized collision energy of 45%. Selected reaction monitoring (SRM) mode was used to acquire the m/z 353 and m/z 359 fragmental peaks. The SRM peak area ratio (COMPOUND I/COMPOUND I-d6) related to the amount of spiked COMPOUND I-d6 was used for the quantification of COMPOUND I and Fe(COMPOUND I)$_3$ in the samples. The same column, gradient and flow rate were used for detection of Fe(COMPOUND I)$_3$ which was detected using an Agilent 1100 HPLC and Orbitrap XL (Thermo) mass spectrometer employing a Thermo IonMax ESI interface. The Fe(COMPOUND I)$_3$ eluted around 11.5 minutes with these conditions. A 10:1 flow split was used for the eluent flow rate of 0.3 mL/min, so that approximately 0.030 mL/min was introduced into the ESI after the split. The ion source MS parameters were as follows: capillary temperature 250° C., sheath gas flow 20 units, positive polarity, source voltage 5.0 kV, capillary voltage 22 V, and tube lens 80 V. The Fourier transform MS (Orbitrap) parameters were: FTMS AGC 1e6, FTMS microscans averaged 2, and FTMS full scan maximum ion time 500 ms. The resolution parameter of 15,000 (peak m/z divided by peak width given as full width at half maximum, at 400 m/z) was used. For the MS-MS CID spectra, a normalized collision energy of 45% was used.

Synthesis and Characterization of Fe(COMPOUND I)$_3$

Five molar equivalents of ferrous ion as FeSO$_4$ in a concentrated water stock was added to COMPOUND I in ethanol which produced a deep red precipitate that was subsequently dissolved in DMSO and characterized by HPLC and mass spectrometry. Fe(COMPOUND I)$_3$ was >95% pure and stable in the complete RPMI-1640 media for at least 5 days.

Comet Assay

Comet assay kits were purchased from Trevigen (Gaithersburg, Md.) and neutral comet assay was performed according to the manufacturer's instructions. Images were collected with a Keyence Fluorescent Microscope (Keyence America, Itasca, Ill.) and quantitated with OpenComet software.

Immunofluorescence Staining

Cells were harvested and washed with PBS twice, fixed in Z-fix solution (buffered zinc formalin fixatives, Anatech, Inc, Creek, Mich.) and permeabilized and blocked with 0.3% Triton X-100 in PBS containing 5% bovine serum albumin. The cells were then incubated with γ-H2AX antibody (1:250 dilution in 0.3% Triton X-100 in PBS containing 1% bovine serum albumin) overnight followed by three washes. Cells were incubated for 1 h with fluorescent-conjugated secondary antibodies (1:1000 dilution) followed by three washes. Slides were mounted with ProLong Gold antifade reagent with 4',6-diamidino-2-phenylindole (DAPI) to stain cell nuclei (Molecular Probes). Fluorescence was viewed with Keyence Fluorescent Microscope using a 100× objective and quantitated with Image J software (the National Institutes of Health).

Statistical Analysis

All two-group comparisons utilized Student's t-test with the assumption of unequal variance. Data are presented as mean ±SEM of a minimum of three independent experiments.

Example 2

Cellular Pharmacology of COMPOUND I

Figure 6:
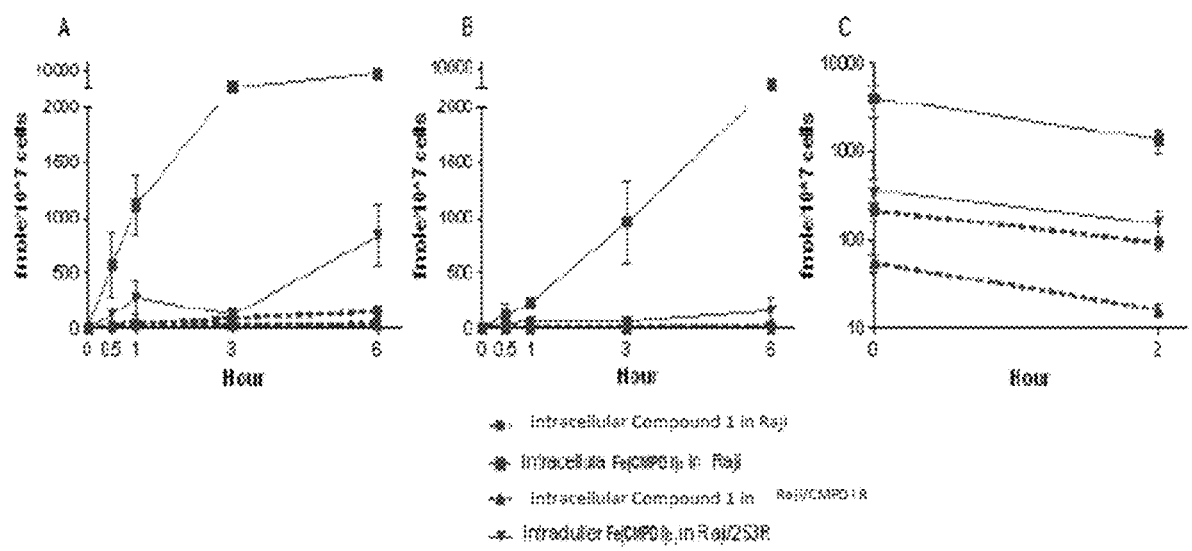
FIG. 6 shows influx and efflux of COMPOUND I and Fe(COMPOUND I)$_3$. (A) Time course of accumulation of COMPOUND I and Fe(COMPOUND I)$_3$ into Raji and Raji/COMPOUND IR cells incubated with 0.5 μM COMPOUND I. (B) Time course of accumulation of Fe(COMPOUND I)$_3$ into Raji and Raji/COMPOUND IR cells incubated with 0.5 μM Fe(COMPOUND I)$_3$. (C) Efflux of COMPOUND I and Fe(COMPOUND I)$_3$ over 2 h from Raji and Raji/COMPOUND IR cells loaded by exposure to 0.5 μM COMPOUND I for 6 h.

Among the cell-types for which COMPOUND I exhibits potent cytotoxicity lymphomas are of interest since most of the standard chemotherapeutic agents used to treat this disease cause myelosuppression which limits dose. For this reason, Raji Burkitt's lymphoma cells were selected for study of the cellular pharmacology of COMPOUND I. The intracellular accumulation of COMPOUND I in the Raji cells was quantified by liquid chromatography tandem mass spectroscopy (LC-MS/MS). COMPOUND I and its internal standard COMPOUND I-d6 eluted from the LC column at ~6.9 minutes with sharp peak profiles. Raji cells accumulated COMPOUND I relatively slowly with content approaching steady-state by 6 h (FIG. 6A).

Careful examination of the LC-MS/MS tracings identified a minor peak that eluted from the LC column at ~8.7 minutes under the same reaction monitoring mode selected for the detection of COMPOUND I. Using LC-HR-ESI-TOFMS (liquid chromatography high resolution electrospray ionization time of flight mass spectrometry) a peak was identified with an m/z 578.65 that also eluted at ~8.7 minutes. High resolution MS/MS analysis with the Obritrap-MS demonstrated that this was a complex of COMPOUND I with ferrous iron at 3 to 1 ratio (FIG. 1B). The structure of the Fe(COMPOUND I)$_3$ ternary complex was characterized by LC-MS-ESI. Two main features of the precursor ion mass spectrum constrained the identification of the structure. The first was the accurate mass measurement of the mass-to-charge ratio (m/z) of its positive two charged ion by high resolution MS. The second feature was the isotope distribution of the measured peak that showed that the structure contained at least one atom of iron. In addition, the MS-MS spectrum of the complex showed two fragment ions, one at 368 m/z that was identical to the free COMPOUND I, and an ion at 789 m/z that was consistent with iron and two remaining COMPOUND I ligands. The calculated mass of the ternary complex, 578.6520 m/z, was in very close agreement with the average m/z result observed on each of several different days, 578.6519 m/z. The difference ratio was −0.2 ppm, measured versus calculated. The inter-day standard deviation was 0.0003 m/z, n=3, and the intra-day mass difference ratio was consistently less than 1.0 ppm. This measure of agreement is within the standard of 3 ppm, which is generally applied for proof-of-structure for synthetic organic products. The presence of iron was confirmed by the isotope pattern that is characteristic of that element. Iron has 4 stable isotopes, $^{54}$Fe, $^{56}$Fe, $^{57}$Fe, and $^{58}$Fe, with natural abundance of 5.85, 91.75, 2.12, and 0.28 percent, respectively. The MS peak that occurs due to the $^{54}$Fe isotope is distinctive because it does not coincide with natural isotopes of carbon, hydrogen and nitrogen of the COMPOUND I ligands. In the spectrum of the complex, its calculated mass is 577.6542 m/z (~1 m/z less than the most abundant isotope peak because the ion is charge plus two). The average mass observed for this peak was 577.6545 m/z, with standard deviation 0.0003 m/z. The difference ratio was 0.5 ppm, inter-day with n=3. The intensity of the $^{54}$Fe peak also consistently measured about 6% of the ion abundance intensity of the main $^{56}$Fe peak, as expected from the natural abundance ratio. For the measurement of the peak positions given above, the results were recalibrated with respect to an internal standard of 391.2843 m/z, an ion of diisooctylphthalate that is ubiquitous due to ambient background.

It was discovered that the Fe(COMPOUND I)$_3$ complex could be synthesized simply by adding FeSO$_4$ to COMPOUND I in ethanol. The purity of Fe(COMPOUND I)$_3$ was documented by HPLC and the complex was found to be stable on storage. The IC$_{50}$ of Fe(COMPOUND I)$_3$ was 145.7±0.5 nM, 1.5-fold less potent than COMPOUND I presumably due to the difficulty of entering cells with its positive doubly charged Fe ion (FIG. 1C). The relative uptake of COMPOUND I and Fe(COMPOUND I)$_3$ was examined by treating Raji cells with 0.5 µM of each compound for 6 h and correcting the intracellular concentrations on the basis of the ionization efficiency of each molecule (FIG. 1D). COMPOUND I-treated cells accumulated more intracellular Fe(COMPOUND I)$_3$ than the Fe(COMPOUND I)$_3$-treated cells, consistent with the difference in the IC$_{50}$ of these two molecules. While the majority of COMPOUND I was converted to Fe(COMPOUND I)$_3$ intracellularly in the COMPOUND I-treated cells, Fe(COMPOUND I)$_3$ did not dissociate intracellularly to produce detectable free COMPOUND I in the Fe(COMPOUND I)$_3$-treated cells. Accordingly, it is believed that Fe(COMPOUND I)$_3$ is the dominant active intracellular form of COMPOUND I.

Example 3

COMPOUND I Causes DNA Damage

Figure 2:
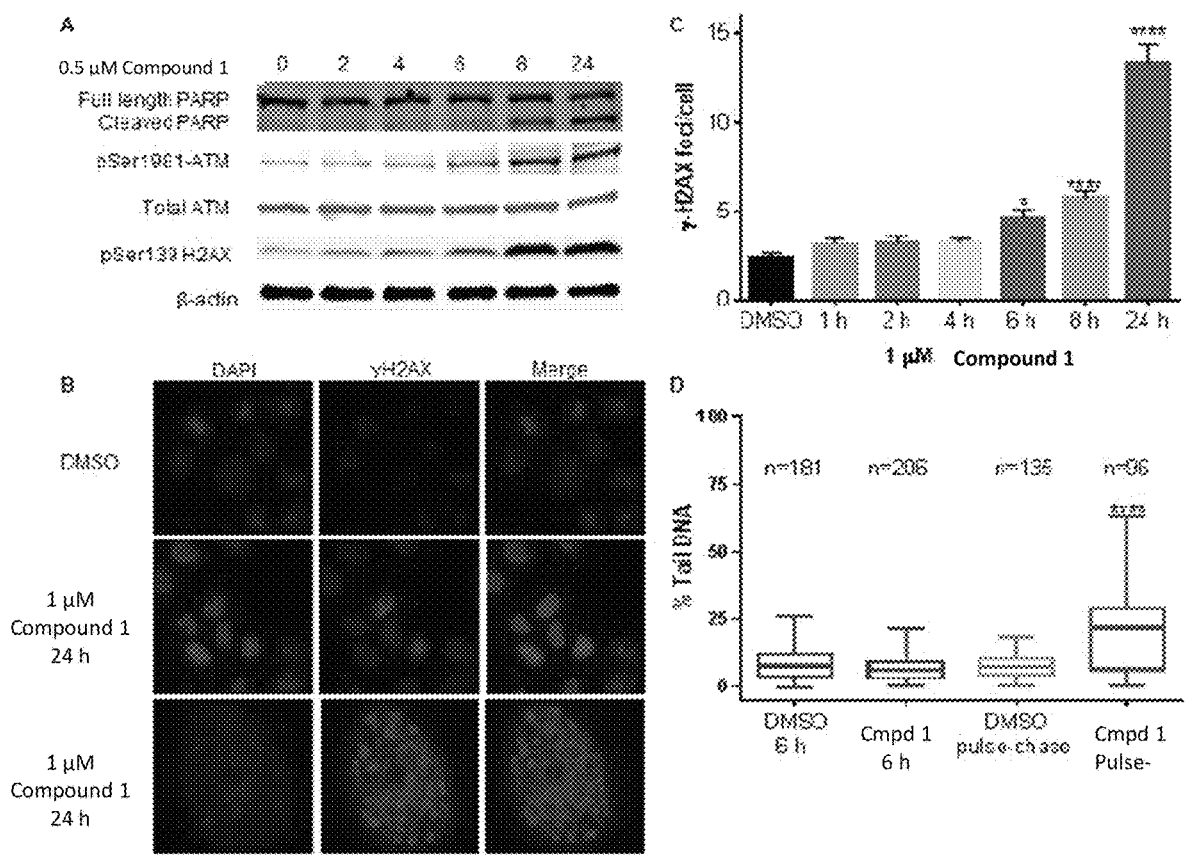
FIG. 2 shows that COMPOUND I causes DNA damage. (A) The accumulation of phospho-ATM, γ-H2AX and cleaved PARP in the Raji cells as a function of duration of exposure to 0.5 μM COMPOUND I. The immunoblot shown is a representative of three independent experiments. (B) Representative immunofluorescent images of nuclear foci formation comparing DMSO- and COMPOUND I-treated CAOV3 cells. (C) Mean ±SEM number of γH2AX foci per cell; N=100. (D) Box and whisker plot showing neutral comment assay quantification of percent tail DNA in CAOV3 cells treated with DMSO or 0.5 μM COMPOUND I for 6 h, N=number of cells examined. Vertical bars, ±SEM; *, p<0.05, ****, p<0.0001.

The structure of COMPOUND I is similar to drugs that bind to quadruplex structures in DNA which results in strand breaks; this led to the investigation of whether COMPOUND I caused damage to DNA. The parental Raji cells were treated with 0.5 µM COMPOUND I for increasing periods of time and induction of DNA damage was assessed by accumulation of the phosphorylated forms of ATM and γH2AX measured by Western blot analysis. FIG. 2A shows that COMPOUND I produced a clear increase in phosphorylated ATM and γH2AX starting at 6 h in Raji cells and that this increased with duration of drug exposure up to 24 h. Cleavage of PARP was detected starting at 8 h indicating the induction of apoptosis. Raji cells have very small nuclei making it difficult to quantify the formation of γH2AX foci, so the human ovarian carcinoma cell line CAOV3 was used for this purpose. FIG. 2B shows representative images of γH2AX foci formation in the CAOV3 cells exposed to DMSO or 1 µM COMPOUND I for 24 h. FIG. 2C shows that an increase in the number of foci was detectable at 1 h and that the number of foci increased more markedly after 8 h. Evidence of DNA damage was further strengthened by the results of the neutral comet assay which mainly detects DNA double strand breaks (FIG. 2D). Although there was no increase in tail DNA when cells were treated with 0.5 µM COMPOUND I for 6 h compared to the DMSO treatment, there was significantly more DNA in the comet tails when cells were treated with COMPOUND I for 6 h and then incubated in drug free media for 18 h (pulse-chase). These results provide strong evidence that COMPOUND I generates DNA damage and produces accumulation of DNA strand breaks capable of triggering apoptosis.

Example 4

BRCA1/2 Deficient Cells are Hypersensitive to COMPOUND I

Figure 3:
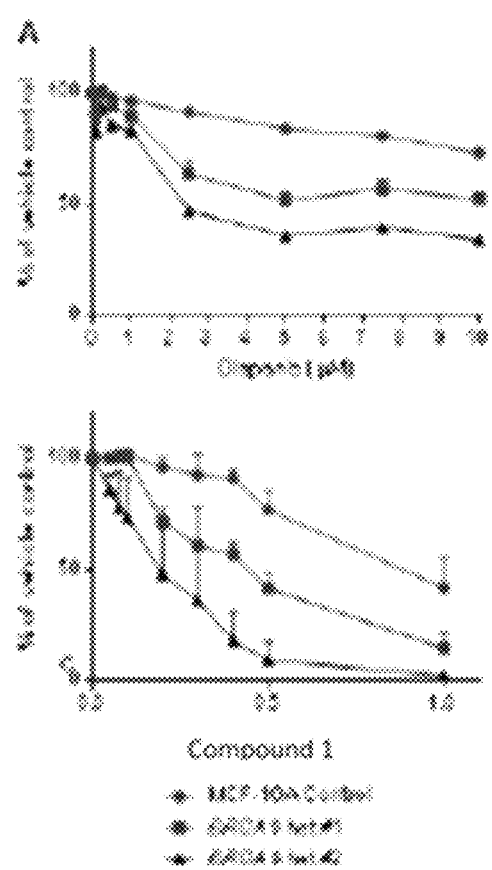
FIG. 3 shows that loss of BRCA1 and BRCA2 function results in hypersensitivity to COMPOUND I. Sensitivity of BRCA1-proficient and -deficient isogenic MCF10A clones (A), hTERT-IMEC clones (B) and MCF7 (C) to olaparib (right) and COMPOUND I (left). Sensitivity of BRCA2-proficient and -deficient isogenic PEO4 and PEO1 (D), and HCT116 BRCA2-deficient clones (E) to olaparib and COMPOUND I. The accumulation of g-H2AFX in the MCF7 control and shBRCA1 clone E7 cells (F) and the BRCA2-proficient HCT116 and the deficient clone B18 cells treated with DMSO or the indicated concentration of COMPOUND I for 24 hours (G). Vertical bars, ±SEM. *, P<0.05; , P<0.01; *, P<0.001.
Figure 3:
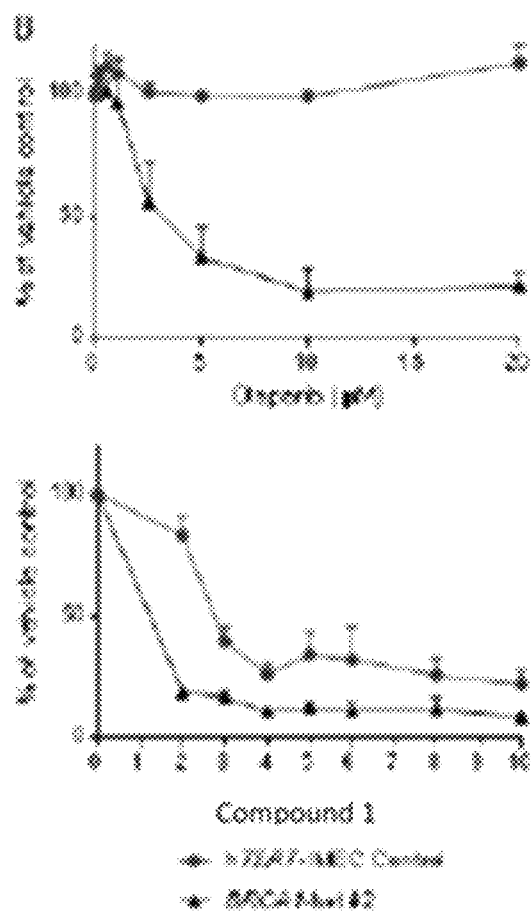
Figure 3:
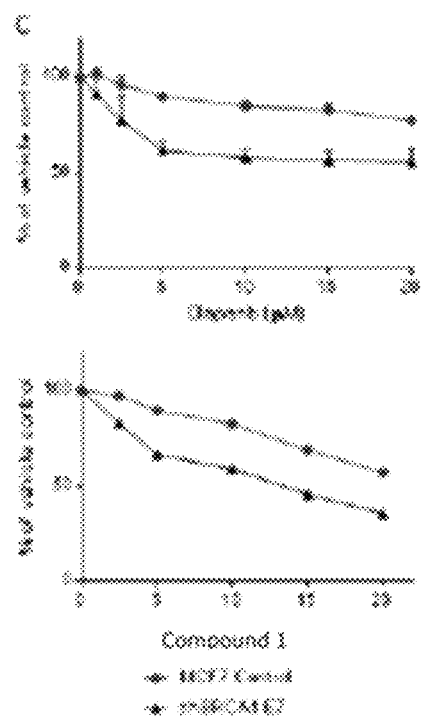
Figure 3:
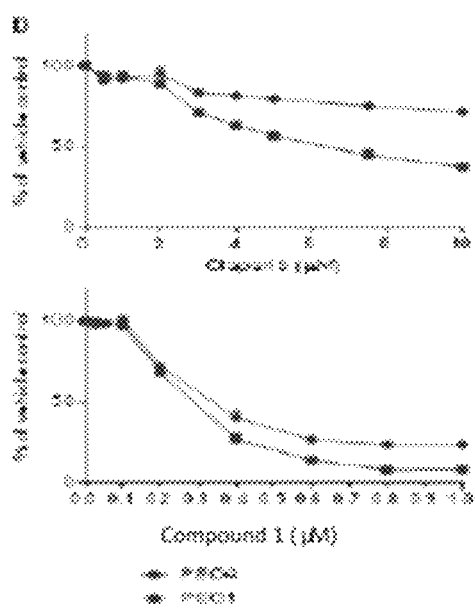
Figure 3:
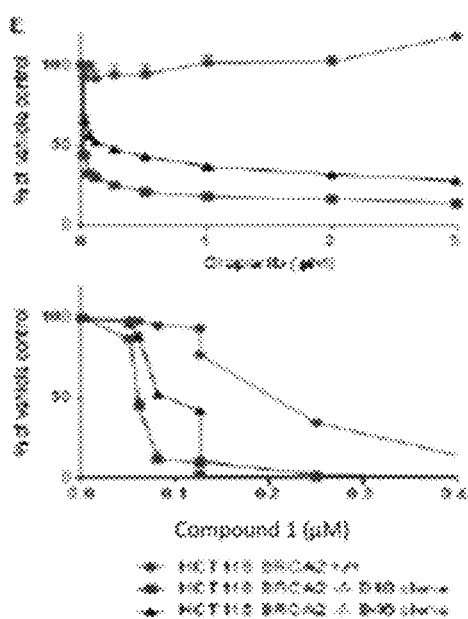
Figure 3:
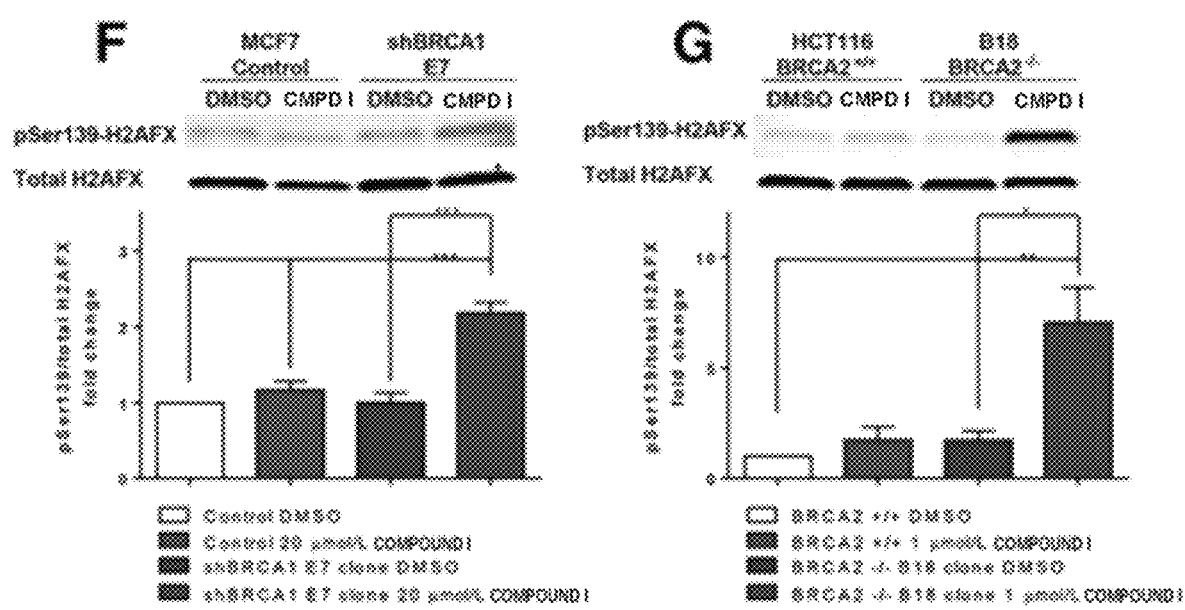

The finding that COMPOUND I produced DNA damage led to the investigation of whether cells deficient in homologous recombination were hypersensitive to this drug. The hypothesis that there would be synthetic lethality between COMPOUND I and BRCA1 deficiency using isogenic pairs of BRCA1-proficient and -deficient human cell lines was tested. Two independent MCF10A subclones, each containing a heterozygous knockin of a 2-bp deletion in BRCA1 that resulted in a premature termination codon (BRCA1-het #1 and #2), were found to be more sensitive to olaparib than clones that underwent random integration of the targeting vector within their genomes (control) confirming the loss of BRCA1 function in the two knockin clones (FIG. 3A, left). These two knockin clones were even more hypersensitive to COMPOUND I (FIG. 3A, right). The effect of impaired BRCA1 function was confirmed in a clone containing the same 2-bp knock-in derived from the hTERT-IMEC cell line, when it too was found to be hypersensitive to both olaparib and COMPOUND I (FIG. 3B). The conclusion that BRCA1-deficient cells are hypersensitive to COMPOUND I was further supported by the results obtained in MCF7 E7 cells in which BRCA1 expression is stably knocked down by the expression of an shRNAi. As shown in FIG. 3C, the E7 clone has a similar degree of hypersensitivity towards olaparib and COMPOUND I. These results in three independent isogenic pairs of BRCA1 competent and BRCA1 incompetent cells indicate that repair of the DNA damage produced by COMPOUND I is in part dependent on homologous recombination and/or other DNA repair pathways in which BRCA1 functions. Whether BRCA2-deficient cells are more sensitive to COMPOUND I was tested using the BRCA2-proficient and BRCA2-deficient ovarian cancer cell lines, PEO4 and PEO1, respectively. PEO1 is BRCA2-deficient and sensitive to cisplatin and a poly(ADP-ribose) polymerase inhibitor AG14361. PEO4 was derived from ascites at the time of relapse with cisplatin resistance and contains a secondary mutation that restores BRCA2 function. Restoration of BRCA2 function increased resistance to both olaparib (FIG. 3D, left), and COMPOUND I (FIG. 3D, right). Similar results were obtained using the BRCA2-proficient HCT116 cells and two BRCA2$^{-/-}$ subclones, B18 and B46 (FIG. 3E). Thus, loss of either BRCA1 or BRCA2 function renders malignant cells hypersensitive to COMPOUND I.

Example 5

Selection for Acquired Drug Resistance

Figure 4:
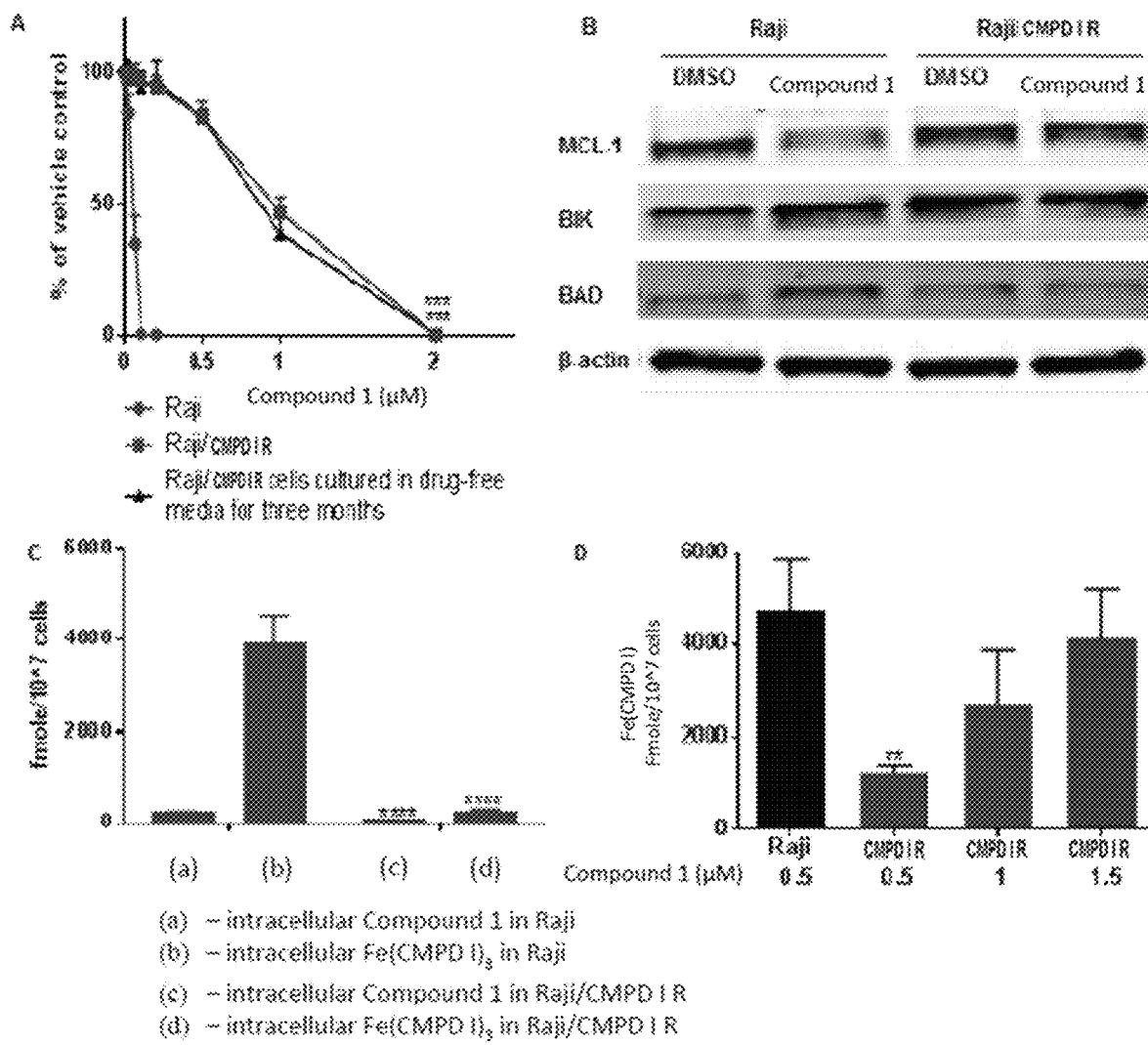
FIG. 4 shows characterization of cells resistant to COMPOUND I (referred to as COMPOUND IR). (A) Concentration-survival curves for Raji (●), Raji/COMPOUND IR (■) Raji/COMPOUND IR and Raji/COMPOUND IR cells after culture in drug-free medium for 3 months (▲). (B) Western blot analysis of proteins involved in apoptosis in Raji and Raji/COMPOUND IR treated with DMSO or COMPOUND I 0.5 μM for 24 h. (C) The intracellular accumulation of COMPOUND I (■) and Fe(COMPOUND I)$_3$ (■) in Raji and Raji/COMPOUND IR cells after a 6 h exposure to 0.5 μM COMPOUND I. (D) The intracellular accumulation of Fe(COMPOUND I)$_3$ in the Raji and Raji/COMPOUND IR cells at 6 h as a function of COMPOUND I concentration. Vertical, bars, ±SEM;  p<0.01; *, p<0.001; ****, p<0.0001.

In order to delineate which effects of COMPOUND I are most closely linked to sensitivity for this drug, a subline of the Raji Burkitt's lymphoma cell line that had acquired resistance (Raji/COMPOUND IR) as a result of repeated exposure to progressively higher concentrations of COMPOUND I over a period of 6 months was developed. Resistance evolved slowly and progressively without an abrupt change at any point during the selection process. The IC$_{50}$ of COMPOUND I for the parental Raji cells was 91.9±22.3 nM when tested using an assay that quantified growth rate during a 120 h exposure to drug. This is in the same range as has been reported for freshly isolated AML blasts and CLL cells. Zhang et al., "Inhibition of c-Myc by ATPO-COMPOUND I as an Innovative Therapeutic Approach to Induce Cell Cycle Arrest and Apoptosis in Acute Myeloid Leukemia [abstract]," *Blood* 2016; 128: 1716; Kurtz et al., "Broad Activity of COMPOUND I in AML and other Hematologic Malignancies Correlates with KFL4 Expression Level [abstract]," *Blood* 2015; 126:1358, both of which are hereby incorporated by reference. The Raji/COMPOUND IR cells were 16.7±3.9-fold resistant to COMPOUND I (IC$_{50}$: 1387.7±98.5 nM). The level of resistance remained stable for at least 3 months during culture in drug-free media (FIG. 4A). Raji/COMPOUND IR cells grew slightly faster than the parental cells but the difference was not statistically significant. At a concentration that induced apoptosis in the Raji sensitive cells, COMPOUND I failed to trigger apoptosis in the Raji/COMPOUND IR cells. When the sensitive cells were treated with 0.5 µM COMPOUND I for 24 h, the pro-apoptotic proteins BIK and BAD increased by 47.5±16.8% and 2.1±0.25-fold, respectively (p<0.05, n=3) and the anti-apoptotic protein MCL-1 decreased by 38.1±2.3% (p<0.001, n=3) compared to the DMSO control. None of these changes were detected in the Raji/COMPOUND IR cells subjected to the same exposure (FIG. 4B).

Example 6

Mechanism of Drug Resistance

Resistance in the Raji/COMPOUND IR cells may be due to alterations in influx or efflux, intracellular detoxification or a change in the primary target of the drug. The intracellular accumulation of both native COMPOUND I and the Fe(COMPOUND I)$_3$ in Raji and Raji/COMPOUND IR cells incubated with either native COMPOUND I or the Fe(COMPOUND I)$_3$ complex was monitored. The rate of accumulation of both forms of the drug was severely reduced in the Raji/COMPOUND IR cells exposed to COMPOUND I (FIG. 6A and Table 1).

TABLE 1

Rate of efflux of COMPOUND I and Fe(COMPOUND I)$_3$ from Raji and Raji/COMPOUND IR cells over first 2 hours (log fmole/10^7 cells/h).

| | Cell line | |
|---|---|---|
| | Raji | Raji/COMPOUND IR |
| COMPOUND I | −0.19 ± 0.025* | −0.26 ± 0.025* |
| | (−0.24~−0.13)$^¥$ | (−0.32~−0.21)$^¥$ |
| Fe (COMPOUND I)$_3$ | −0.22 ± 0.044* | −0.17 ± 0.063* |
| | (−0.32~−0.13)$^¥$ | (−0.32 to −0.014)$^¥$ |

*Mean ± SEM, n = 6
$^¥$95% Confidence Intervals

Figure 7:
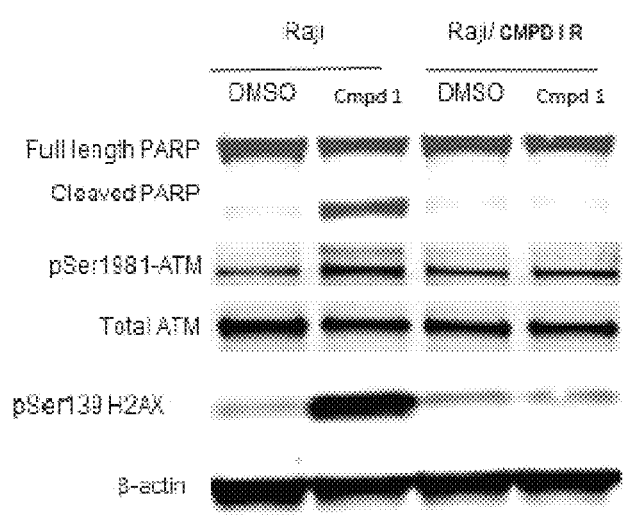
FIG. 7 shows the accumulation of phospho-ATM, γ-H2AX and cleaved PARP in Raji compared to that in Raji/COMPOUND IR cells.

The same was true to lesser extent when the cells were incubated with the Fe(COMPOUND I)$_3$ complex (FIG. 6B). In contrast, there was no apparent difference in the efflux over the first 2 h of either ATPO-COMPOUND I or Fe(COMPOUND I)$_3$ following loading of the cells with either form of the drug. These results indicate that resistance to COMPOUND I in Raji cells is associated with impaired accumulation of both forms of the drug. A more detailed measurement of drug accumulation at 6 h confirmed that the accumulation of both forms of the drug was markedly reduced when the Raji/COMPOUND IR cells were incubated with COMPOUND I; however, the level of the Fe(COMPOUND I)$_3$ complex still exceeded that of the native drug (FIG. 4C). Only when the Raji/COMPOUND IR cells were treated with at least 3 times as much COMPOUND I did the intracellular content of Fe(COMPOUND I)$_3$ finally reach a level similar to that in the sensitive cells (FIG. 4D). Treatment of the Raji/COMPOUND IR cells with 0.5 µM COMPOUND I for 24 h produced no increase in phospho-ATM or phospho-γH2AX, and no detectable PARP cleavage (FIG. 7) consistent with substantially less intracellular COMPOUND I and Fe(COMPOUND I)$_3$ in the resistant cells.

To obtain further insight into the resistance mechanism, RNA-seq analysis was carried out on three independent samples of both the sensitive Raji and resistant Raji/COMPOUND IR cells. A gene-level differential expression analysis was performed by removing all genes with less than 50 reads across all 6 samples as genes with only low level expression can cause irregularities in differential expression analysis. Genes were considered to be differentially expressed if their adjusted p-value was less than the 0.05 level and their fold change was >2 in either direction. Among the 13,791 evaluable genes there were 1,012 that were significantly up-regulated in the Raji/COMPOUND IR cells and 704 genes that were significantly down regulated. The ATP-binding cassette sub-family member ABCG2 was the most up-regulated gene with more than a thousand-fold increase in transcript level (Table 2).

TABLE 2

Rank order of genes up-regulated in Raji/COMPOUND IR cells.

| Gene ID | Gene name | Fold increase | Adjusted p value |
|---|---|---|---|
| ENSG00000118777 | ABCG2 | 1127.3 | 2.24E−05 |
| ENSG00000114200 | BCHE | 173.8 | 3.24E−05 |
| ENSG00000142149 | HUNK | 52.9 | 8.59E−04 |

TABLE 2-continued

Rank order of genes up-regulated in Raji/COMPOUND IR cells.

| Gene ID | Gene name | Fold increase | Adjusted p value |
|---|---|---|---|
| ENSG00000060709 | RIMBP2 | 46.6 | 3.99E−04 |
| ENSG00000165695 | AK8 | 42.5 | 5.74E−04 |
| ENSG00000234323 | RP11-308N19.1 | 41.4 | 3.16E−04 |
| ENSG00000261690 | AC009133.12 | 39.3 | 1.60E−03 |
| ENSG00000161570 | CCL5 | 37.3 | 5.74E−05 |
| ENSG00000168824 | NSG1 | 33.0 | 9.84E−04 |
| ENSG00000154864 | PIEZO2 | 31.6 | 3.88E−04 |

Figure 5:
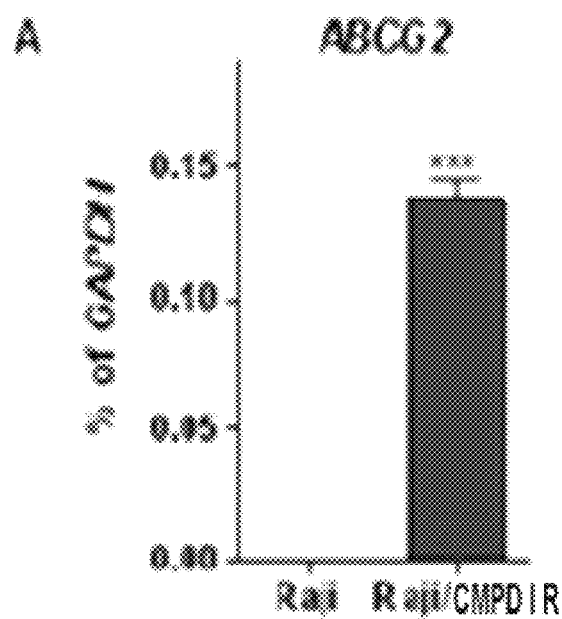
FIG. 5 shows the role of ABCG2 in resistance to COMPOUND I. (A) Relative levels of ABCG2 mRNA in the Raji and Raji/COMPOUND IR. (B) Western blots of biotinylated proteins were probed with anti-ABCG2 antibody. Na/K ATPase served as a loading control. (C) Cytotoxicity of Ko143 in Raji (●) and Raji/COMPOUND IR (■). (D) Concentration-survival curves for Raji (●) and Raji/COMPOUND IR (■) treated with COMPOUND I alone or in combination with COMPOUND I and 5 nM (▲) or 50 nM Ko143 (▼). (E) Cytotoxicity of topotecan in Raji (●) and Raji/COMPOUND IR (■) and the combination of topotecan and 50 nM Ko143 in Raji/COMPOUND IR (▲). (F) Cytotoxicity of carboplatin in Raji (●) and Raji/COMPOUND IR (■) and the combination of carboplatin and 50 nM Ko143 in Raji/COMPOUND IR (▲). (G) Concentration-survival curves for HEK-293 transfected with pcDNA (●) and ABCG2, clone R5 (■) treated with COMPOUND I. Vertical, bars, ±SEM; **, p<0.01.
Figure 5:
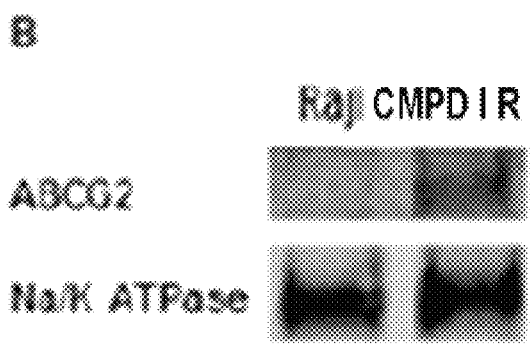
Figure 5:
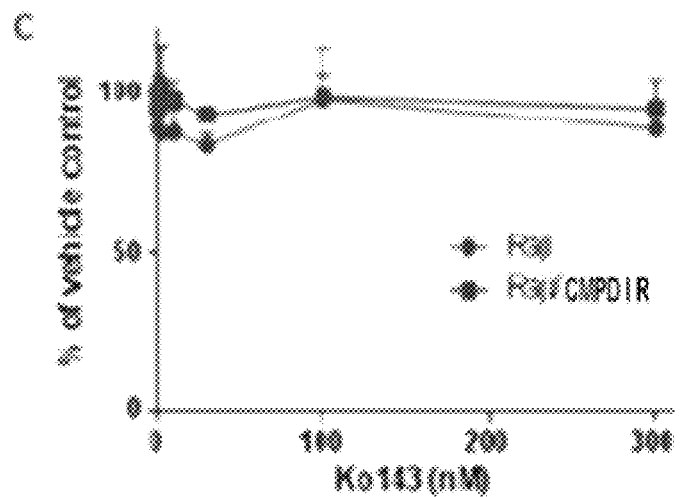
Figure 5:
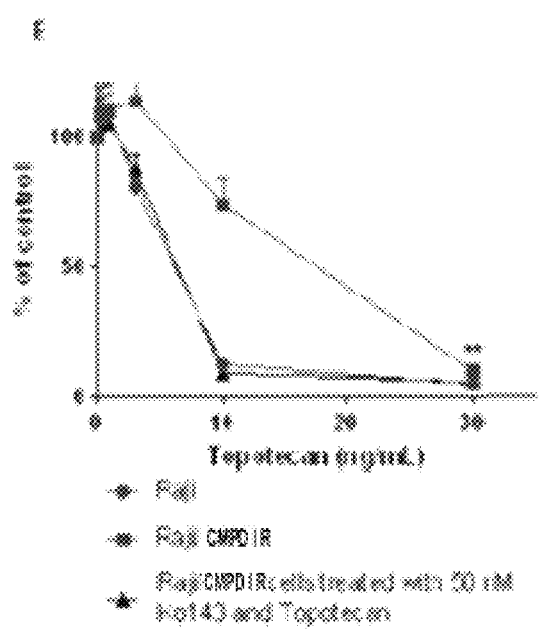
Figure 5:
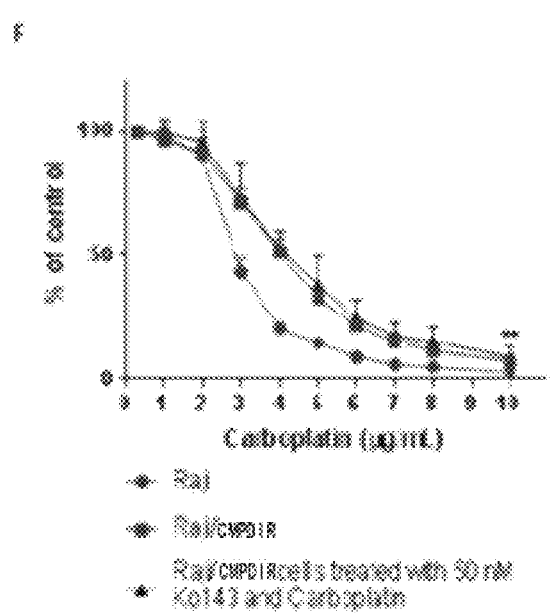
Figure 5:
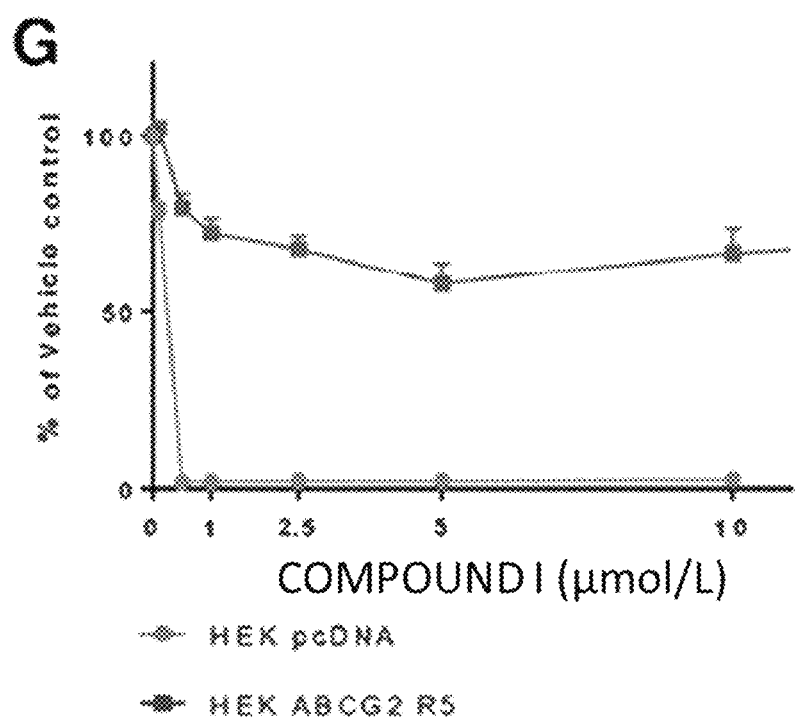

Although several other multidrug resistance ABC transporters were also up-regulated in Raji/COMPOUND IR, the increase in ABCG2 transcripts was the most prominent (Table 3). The marked up-regulation of ABCG2 in the Raji/COMPOUND IR cells was confirmed by qRT-PCR and Western blot analysis (FIGS. 5A and B).

TABLE 3

ABC transporter family member genes up-regulated in Raji/COMPOUND IR cells.

| Gene ID | Gene name | Fold increase | Adjusted p value |
|---|---|---|---|
| ENSG00000118777 | ABCG2 | 1127.3 | 2.24E−05 |
| ENSG00000160179 | ABCG1 | 0.9 | 8.56E−01 |
| ENSG00000085563 | ABCB1 (MDR1) | 4.8 | 8.24E−04 |
| ENSG00000103222 | ABCC1 (MRP1) | 1.5 | 1.25E−02 |
| ENSG00000023839 | ABCC2 (MRP2) | 3.2 | 6.09E−03 |

Ko143 is a specific ABCG2 inhibitor with more than 200-fold selectivity relative to its ability to inhibit the P-gp or MRP-1 transporters. Ko143 itself was not toxic to Raji or Raji/COMPOUND IR cells at concentrations up to 300 nM (FIG. 5C). To test the hypothesis that COMPOUND I is a substrate for ABCG2, the ability of Ko143 to reverse the resistance of the Raji/COMPOUND IR cells was evaluated. The data in Table 4 and FIG. 5D show that concurrent treatment with Ko143 significantly reversed COMPOUND I resistance in the Raji/COMPOUND IR cells.

To provide further evidence of augmented ABCG2 function, the resistant cells were tested for cross-resistance to topotecan, a well-documented ABCG2 substrate. The Raji/COMPOUND IR cells were found to be 3-fold cross-resistant to topotecan and treatment with Ko143 reversed this resistance completely (FIG. 5E). Intriguingly, Raji/COMPOUND IR was also significantly cross-resistant to carboplatin even though carboplatin is not thought to be an ABCG2 substrate; treatment with Ko143 did not reduce the carboplatin $IC_{50}$ in the Raji/COMPOUND IR cells (FIG. 5F). Surprisingly, Raji/COMPOUND IR cells were found to be hypersensitive to etoposide, an ABCG2 substrate and potent double strand break inducer. GO and pathway analysis from the RNA-seq data revealed that the DNA repair pathways were downregulated in Raji/COMPOUND IR which partially explained the hypersensitivity to etoposide.

Example 7

COMPOUND I Interaction With G-Quadruplex DNA is Linked to Inhibition of c-MYC

Current mechanistic studies demonstrated that COMPOUND I modulates c-MYC at the transcriptional level by decreasing acetylated H3K27 at its promoters and additionally by destabilizing c-MYC mRNA. In addition, differential gene expression analysis of RNA-seq and reverse phase protein array (RPPA) data highlighted a role for c-MYC in the mechanism of COMPOUND I (GO terms—Down regulated by c-MYC p-value 6E-26, Gene promoters bound by c-MYC p-value 4.2 E-10, ChIP targets of c-MYC p-value 3.3E-8). Furthermore, from the RPPA data an increase in p-Chk1, p-Chk2, γH2Ax, and total p53 and E2F1 was observed, all of which are indicative of activation of DNA damage response pathways. This was accompanied by elevated levels of XBP1, GRP78, and p-p38 that point towards cellular stress response signaling (GO term Regulation of Cell Stress, p-value 1.89E-8).

Although COMPOUND I may participate in multiple mechanistic events, the effect of COMPOUND I on c-MYC expression, cell cycle arrest and DNA damage, as well as synthetic lethality in cells with compromised DNA repair mechanisms, can be explained by the action of the Fe(COMPOUND I)$_3$ complex on G-quadruplex DNA motifs.

TABLE 4

Effect of ABCG2 inhibitor on resistance to COMPOUND I

| Cell Line | COMPOUND I Alone | | COMPOUND I + 5 nM Ko143 | | COMPOUND I + 50 nM Ko143 | |
|---|---|---|---|---|---|---|
| | $IC_{50}$ (nM)[#] | RR[§] | $IC_{50}$ (nM) | RR[§] | $IC_{50}$ (nM) | RR[§] |
| Raji/COMPOUND IR | 1387 ± 94 | 16.7 ± 3.9[b] | 853 ± 44 | 10.9 ± 1.9[c] | 200.6 ± 20.7 | 2.5 ± 0.7[a] |
| Raji | 105 ± 2.4 | — | 98.3 ± 0.8 | — | 103.1 ± 2.9 | — |

[#]Mean ± SEM
[§]Relative resistance
[a]p < 0.05;
[b]p < 0.01;
[c]p < 0.001

Example 8

Materials and Methods for Examples 9-16

Cells and Compounds

EOL-1, GRANTA-519, Jeko-1, Jurkat, Molm-13, NOMO-1, SKM-1, and SU-DHL-6 were obtained from Leibniz-Institut DSMZ. HL-60, KG-1, Mino, MV4-11, Raji, and THP-1 were obtained from ATCC. HEL92.1.7 were obtained from the European Collection of Authenticated Cell Cultures and Ramos cells were a gift from Dr. M. Andreeff (MD Anderson Cancer Center, Houston, Tex.). All cells were cultured in complete media as per the manufacturer's instructions. Early passage cells were collected and frozen within 1 month of receipt from the manufacturer. All experiments were performed on early passage cells within 6 weeks of thawing. MycoScope Mycoplasma Detection Kit (Genlantis catalog #MY01050) was used to screen for potential contamination every 6 months. Peripheral blood mononuclear cells (PBMC) were isolated from fresh healthy donor blood using Ficoll-Paque PLUS (GE Healthcare, catalog #17-1440-02). For synthesis of COMPOUND I free base, 10-phenanthroline-5,6-dione (1.2 equivalents), acetic acid (22 volumes), 2-methyl-5-fluoroindole-3-carboxaldehyde (1.0 equivalents), and ammonium acetate (15 equivalents) were reacted under medium agitation while heated at 95±5° C. for 3 to 7 hours. The reaction was cooled to between 20° C. and 25° C., filtered, rinsed with acetic acid and ethanol, and dried with $N_2$ purge, followed by a wash with 2:1 ethanol:water at 65° C. for 4 hours, cooling to 20° C. to 25° C., filtration, rinsing with 2:1 ethanol:water and EtOAc, and then dried with $N_2$ purge. The purity by HPLC was 99.5%, and the structural identity was confirmed by FT-IR, $^1$HNMR, $^{13}$C NMR, and LC/MS. For Fe(COMPOUND I)$_3$ synthesis, five molar equivalents of ferrous ion FeSO$_4$ in water was added to COMPOUND I dissolved in ethanol. The deep red precipitate produced, Fe(COMPOUND I)$_3$, was collected and dissolved in DMSO and characterized by HPLC and mass spectrometry as >95% pure. CX-5461 (7) was purchased from MedChem Express (catalog #HY-13323).

Cytotoxicity Study

Cells were plated and treated with vehicle DMSO or COMPOUND I (10 concentrations) in 96-well plates for 5 days at 37° C. and 5% CO$_2$. Cell viability was measured using CellTiter 96 AQ$_{ueous}$ one solution (MTS) cell proliferation assay (Promega, catalog #G3581), and IC$_{50}$ values were calculated using GraphPad Prism 7 software.

Uptake and Efflux Assay

Cells exposed to COMPOUND I were homogenized in acetonitrile containing 5 ng of deuterated COMPOUND I standard. Samples were analyzed at the UCSD Molecular Mass Spectrometry Facility employing an Agilent 1260 liquid chromatograph (LC) system coupled with a Thermo LCQdeca mass spectrometer using positive ion mode electrospray ionization as the ion source.

qRT-PCR

Cells were treated with vehicle or COMPOUND I at various concentrations for 24 hours or at a single concentration for 1, 3, 6, 12, and 24 hours before harvesting. Cells were lysed by QiaShredder columns (QIAGEN, catalog #79656), total RNA was isolated using QIAGEN RNeasy Plus Mini Kit (catalog #74134), and cDNA was synthesized utilizing Transcriptor Universal cDNA master mix (Roche, catalog #05893151001) and then used for qRT-PCR analysis using FastStart essential DNA probes master mix (Roche, catalog #06402682001) and Roche LightCycler96. Primer probe pairs were purchased from IDT (Table 5). Expression was calculated as fold change over vehicle treated samples after normalizing to GAPDH ($2_t^{\Delta\Delta C}$).

TABLE 5

| IDT primer probe pairs | |
|---|---|
| Gene | IDT assay name |
| GAPDH | Hs.PT.58.40035104 |
| CDKN1A (p21) | Hs.PT.58.40874346 |
| MYC | Hs.PT.58.26770695 |

Western Blotting

Cells were treated as described above. Whole-cell lysates were prepared, separated by SDS-PAGE, and transferred to nitrocellulose membranes. Detection antibodies used are listed in Table 6. Densitometry was performed using ImageJ or Image Studio Lite Version5.2 software and normalized to the density of GAPDH.

TABLE 6

| Antibodies | | |
|---|---|---|
| Antibodies | Cat# | Company |
| CCND3/Cyclin D3 | 2936 | Cell Signaling |
| CDK4 | 12790 | Cell Signaling |
| PARP1 | 9532 | Cell Signaling |
| Total TP53 | sc-126 | Santa Cruz |
| TP53 Phos-Ser15 | 2528 | Cell Signaling |
| TP53 acetyl K382 | 2525 | Cell Signaling |
| γH2AX | 9718 | Cell Signaling |
| CHEK1 phos-Ser345 | 2348 | Cell Signaling |
| CHEK1 | 2360 | Cell Signaling |
| MAPK14/p38 phos-Thr180/Tyr182 | 4511 | Cell Signaling |
| MAPK14/p38 | 8690 | Cell Signaling |
| MAPK8/JNK phos-Thr183/Tyr185 | 4668 | Cell Signaling |
| CDKN1A/p21 | sc-397 | Santa Cruz |
| GAPDH | sc-365062 | Santa Cruz |
| MYC | sc-40 | Santa Cruz |
| RIgG | sc-2025 | Santa Cruz |
| 20 Rabbit HRP | 170-8515 | Biorad |
| 20 Mouse HRP | 170-6516 | Biorad |

Flow Cytometry for Apoptosis and Cell-Cycle Analysis

Cells were treated as described above. To determine apoptosis, cells were stained with FITC-Annexin V and propidium iodide (PI; BD Pharmingen, catalog #556570) and then analyzed on BD Accuri C6 flow cytometer. To measure DNA synthesis and phases of cell cycle, treated cells were stained with 5-ethynyl-2'-deoxyuridine (Edu) Alexa Fluor 488 (Thermo Fisher Scientific, catalog #C10425) and PI (PI/RNase A staining solution, BD Biosciences, catalog #550825). The dead cells were excluded from analysis by using Live/Dead Fixable Far Red Dead Cell Stain Kit (Thermo Fisher Scientific, catalog #L34973). Staining was performed as per the manufacturers' instructions.

RNA Sequencing Analysis

Treated MV4-11 cells were subjected to total RNA extraction (as for qRT-PCR analysis) and sequenced at the UCSD genomics core facility. RNA was processed using Illumina TruSeq and single end sequenced for 50-bp reads on the Illumina HiSeq4000. Data were analyzed by the McWeeny lab at Oregon Health and Science University (Portland, Oreg.). FASTQ files were assessed for read base distribution and sequence representation using FASTQC http:// www.bioinformatics.babraham.ac.uk/projects/fastqc/.
Reads were aligned to HG37 using SubRead v1.5.0-pl keeping uniquely mapped reads. Differential expression genes with less than 50 reads (across all 4 samples) were discarded. Raw data and processed files are available on GEO (https://www.ncbi.nlm.nih.gov/geo/query/acc.cgi?acc=GSE111949) accession number GSE111949.

Reverse-Phase Protein Array Analysis

MV4-11 cells were treated as for RNA sequencing (RNA-seq) analysis and whole-cell extracts were prepared for Western blotting. Samples were processed at MD Anderson Cancer Center reverse-phase protein array (RPPA) core facility (details at https://www.mdanderson.org/research/research-resources/core-facilities/functional-proteomics-rppa-core/rppa-process.html). Protein expression levels were averaged for 3 replicates and heatmaps were drawn using GraphPad Prism 7.

Chromatin Immunoprecipitation Coupled With qPCR

MV4-11 cells were treated with vehicle DMSO or 500 nmol/L COMPOUND I for 2, 6, or 24 hours and then crosslinked with 1% formaldehyde. Chromatin was extracted by sonication and then incubated with H3K27ac (Active Motif #39133) antibody overnight. The antibody:DNA complexes were isolated with Protein G beads (Invitrogen Dynabeads catalog #10004D) and analyzed by qPCR with primers specific to the MYC promoter (Table 7). H3K27ac enrichment was calculated as fold over input DNA control.

TABLE 7

ChIP Primers

| Location | forward primer | reverse primer |
|---|---|---|
| MYC Prom1 | GAGCAGCAGCGAAAGGGAGA (SEQ ID NO. 3) | CAGCCGAGCACTCTAGCTCT (SEQ ID NO. 4) |
| MYC Prom 2 | CCGCATCCACGAAACTTTG (SEQ ID NO. 5) | GGGTGTTGTAAGTTCCAGTGCAA (SEQ ID NO. 6) |

RNA Decay Assay

Cells were treated for 3 hours with vehicle DMSO or 500 nmol/L COMPOUND I followed by 1 µmol/L actinomycin D. Aliquots of cells were taken before and then every 10 minutes after actinomycin D addition for RNA extraction and cDNA synthesis as for qRT-PCR analysis. Levels of MYC and 28s rRNA were analyzed using specific primers (Table 8) and MYC RNA expression was normalized to 28 s rRNA [$2^{\wedge}(28\ s\ C_t\ value - MYC\ C_t\ value)$].

TABLE 8

Expression Primers

| Gene | forward primer | reverse primer |
|---|---|---|
| 28s RNA | AGTAGCAAATATTCAAACGAGAACTTT (SEQ ID NO. 7) | ACCCATGTTCAACTGCTGTTC (SEQ ID NO. 8) |
| MYC | CAGTAGAAATACGGCTGCAC (SEQ ID NO. 9) | TTCGGGTAGTGGAAAACCAG (SEQ ID NO. 10) |

FRET Assay

FRET assay and data analysis was performed as described previously and modified by using dual labeled (5' FAM-3' BHQ1) single-stranded oligos. Melting temperature of each oligo was assessed in the presence of vehicle DMSO or escalating concentrations of COMPOUND I, Fe(COMPOUND I)$_3$, CX-5461, or TMPyP4 using a Roche LightCycler 96 [at 37° C. for 300 seconds followed by temperature increased in 3° C. intervals up to 91° C. (25 steps) with 300-second total incubation time at each temperature]. Drug and oligo reaction mixes were analyzed immediately or incubated for 6 hours at room temperature and then analyzed. Primer information is provided in Table 9. Longer incubation time did not affect Fe(COMPOUND I)$_3$, TMPyP4, or CX-5461 activity but enhanced COMPOUND I G4-binding ability. COMPOUND I data are presented for 6-hour time point.

TABLE 9

G-quadruplex oligos

| G4 Location | G4 oligo sequence |
|---|---|
| Telomere | 5'(FAM)-GGGTTAGGGTTAGGGTTAGGGTTAGGGTTAGGG-(BHQ1)3' (SEQ ID NO. 11) |
| MYC | 5'(FAM)-CCATGGGGAGGGTGGAGGGTGGGGAAGGT-(BHQ1)3' (SEQ ID NO. 12) |
| KIT | 5'(FAM)-TTATAGGGAGGGCGCTGGGAGGAGGGAGGAGAC-(BHQ1)3' (SEQ ID NO. 13) |
| rRNA | 5'(FAM)-AATAAGGGTGGCGGGGGGTAGAGGGGGGTAATA-(BHQ1)3' (SEQ ID NO. 14) |
| ds_DNA | 5'(FAM)-TATAGCTATA[Sp~C18]TATAGCTAT-(BHQ1)3' (SEQ ID NO. 15) |

Example 9

Figure 8:
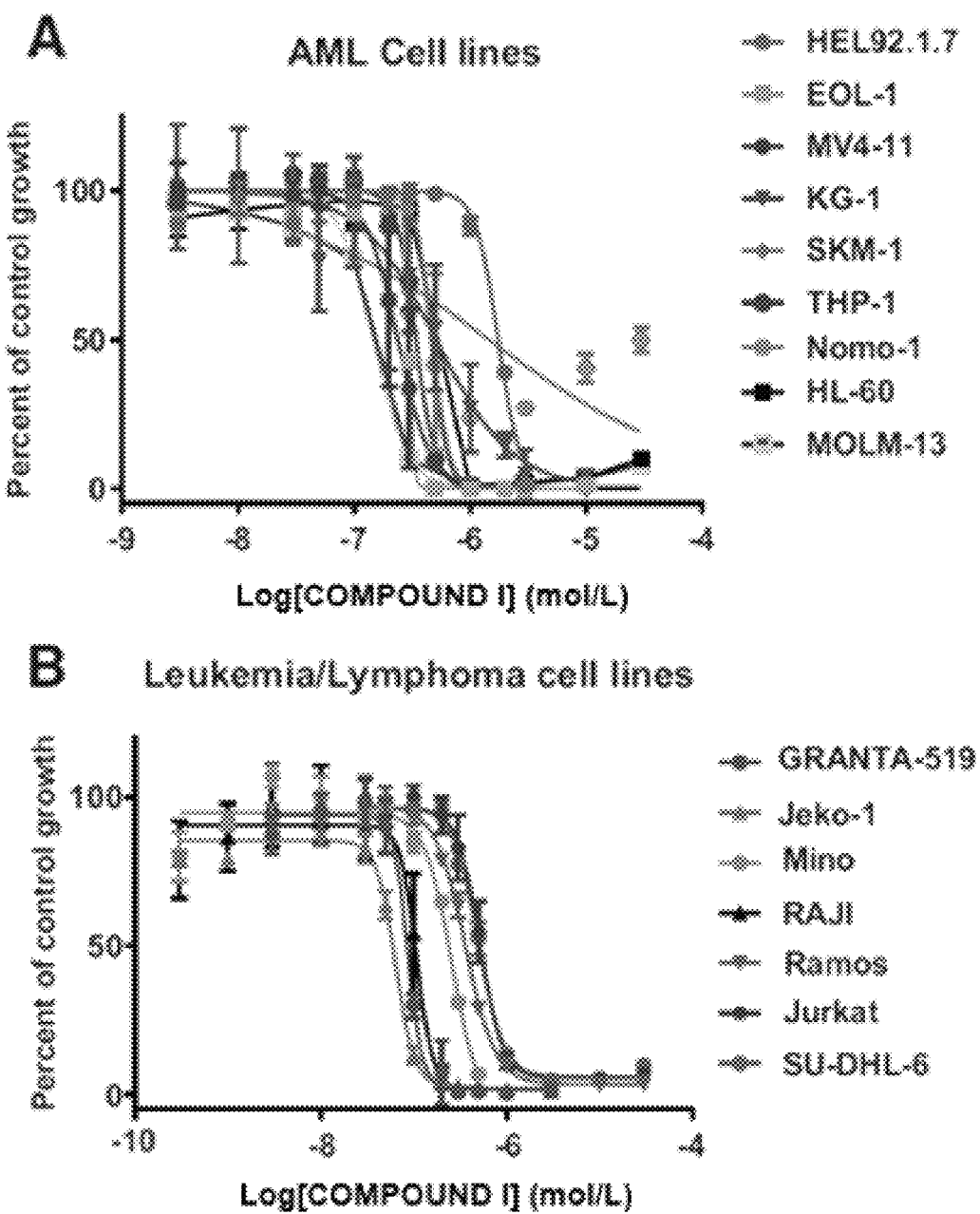
FIG. 8 shows the antiproliferative activity of COMPOUND I against leukemia and lymphoma cell lines. A) Concentration-response curves for AML cell lines treated for 5 days with COMPOUND I. Cell growth expressed as percent of growth of vehicle-treated cells. B) Concentration-response curve for other leukemia and lymphoma cell lines. Error bars, ±SD of at least three replicate assays.
Figure 9:
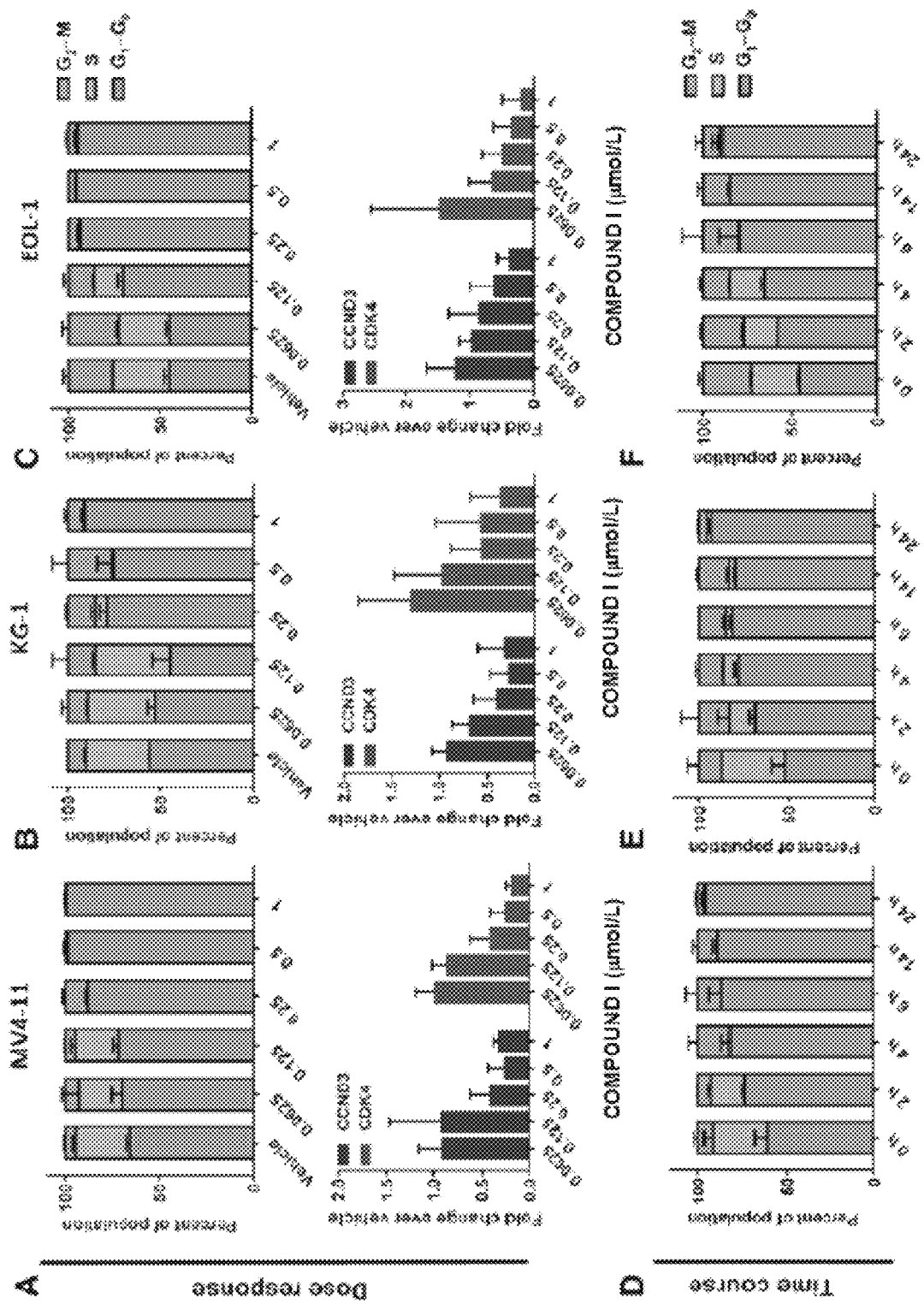
FIG. 9 shows that COMPOUND I induces G0-G1 cell-cycle arrest in a dose- and time-dependent manner in AML cell lines. A) Top, MV4-11 cells treated with COMPOUND I at indicated concentrations for 24 hours. Cell-cycle distribution assayed as described in the Materials and Methods section. Bottom, CDK4 and CCND3 protein levels in MV4-11 cells after 24-hour exposure to COMPOUND I. Protein levels quantitated from three independent Western blots, graphed as fold change over vehicle. B) and C) Effect of COMPOUND I on cell-cycle distribution in KG-1 and EOL-1 cells. D)-F), Effect of COMPOUND I on cell-cycle distribution as a function of duration of exposure (MV4-11 cells,500 nmol/L; KG-1 cells, 600 nmol/L COMPOUND I; and EOL-1 cells, 300 nmol/L COMPOUND I). Error bars, ±SD of two replicate assays for flow cytometry and three replicates for Western blots.
Figure 15:
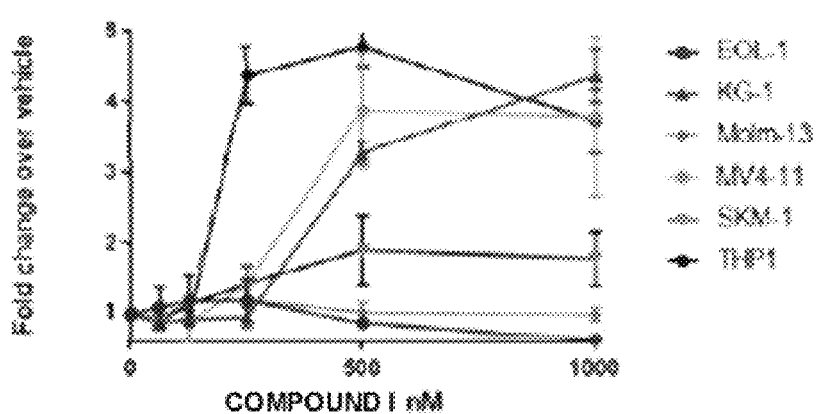
FIG. 15 shows the Induction of KLF4 and CDKN1A (p21) by COMPOUND I in AML cell lines. A) KLF4 mRNA induction after 24 hr treatment with COMPOUND I at concentrations listed. B) Concentration-dependent increase in CDKN1A mRNA expression in AML lines. C) Western blot analysis of CDKN1A protein level in MV4-11 cells after 24 h exposure to vehicle (v) or increasing concentrations of COMPOUND I. D) Time dependent increase in p21 mRNA. E) Western blot analysis of CDKN1A protein level in MV4-11 cells as a function of duration of exposure to 500 nM COMPOUND I (A) as compared with vehicle (V). All mRNA measurements were made by qRT-PCR and graphed relative to GAPDH loading control. Error bars, ±SD from 3 replicate experiments.
Figure 15:
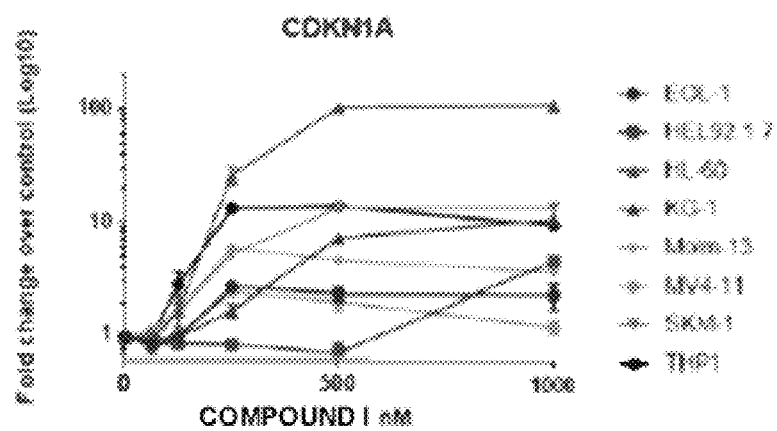
Figure 15:
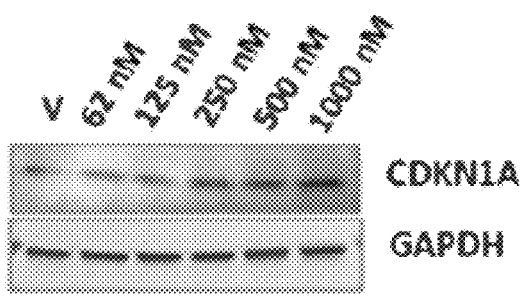
Figure 15:
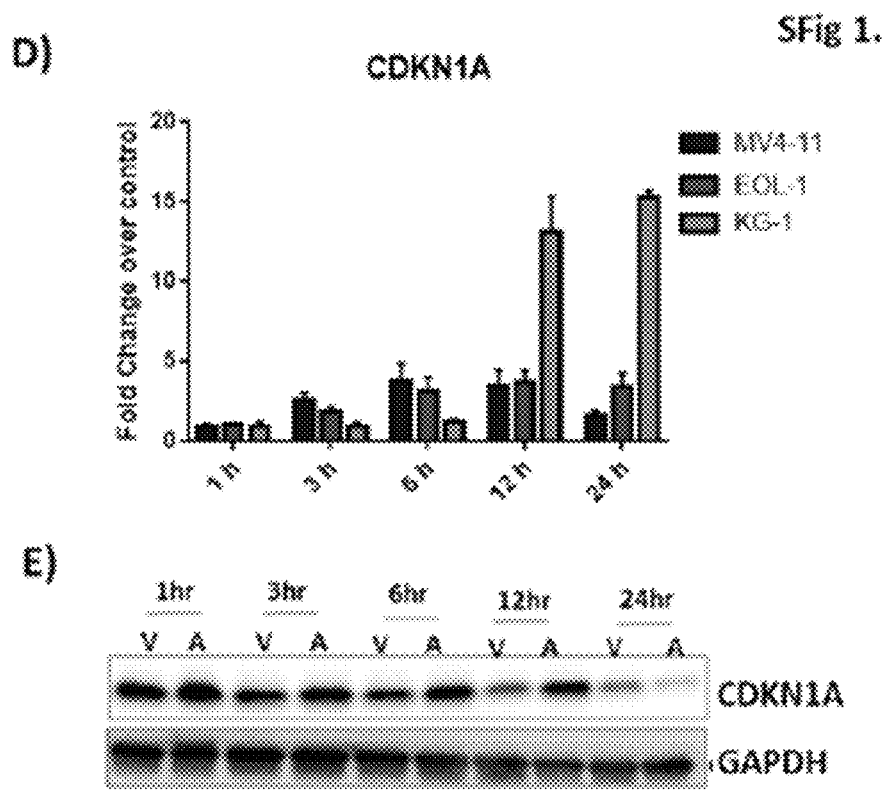
Figure 16:
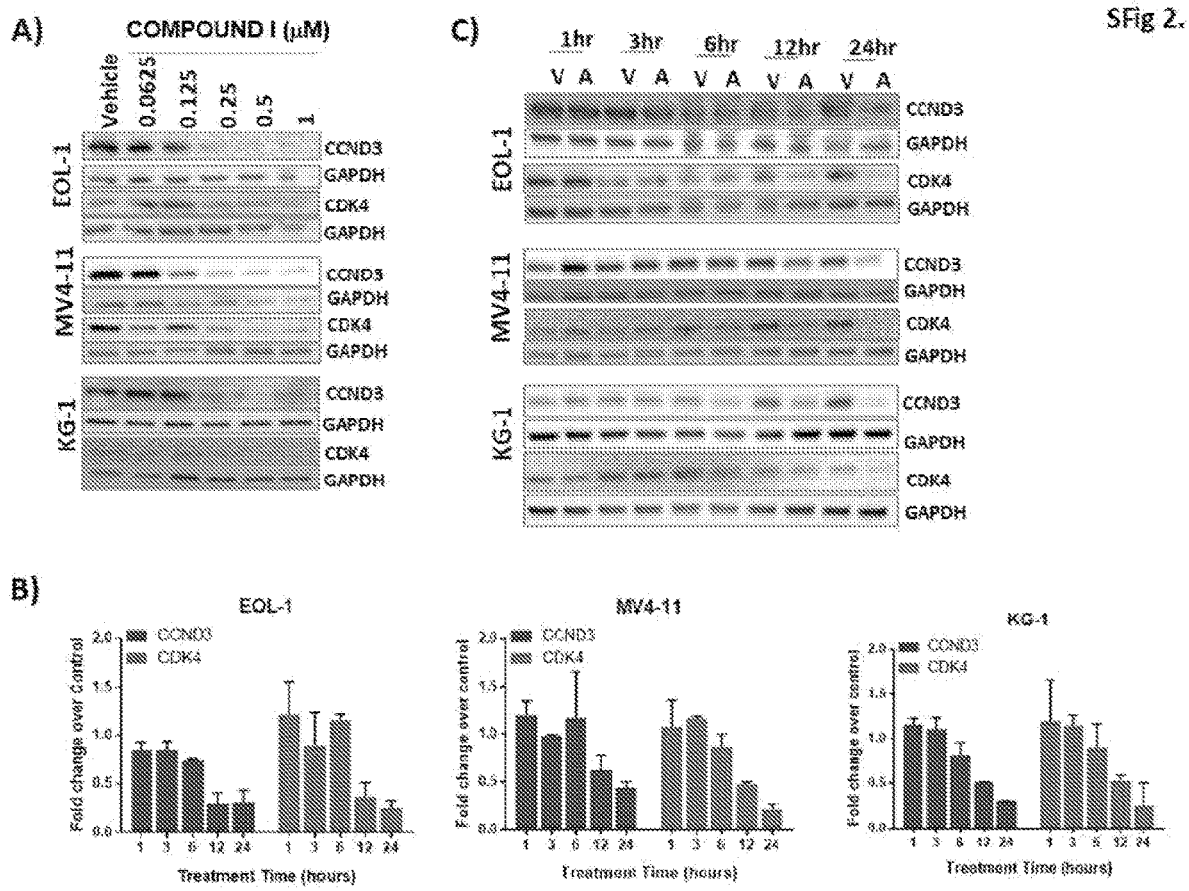
FIG. 16 shows that COMPOUND I induces $G_0/G_1$ cell cycle arrest in a dose- and time-dependent manner in AML cell lines. A) Representative western blot of CDK4 and CCND3 protein level in MV4-11, KG-1, and EOL-1 cells quantitated in lower panels of FIGS. 16A-C. B) CDK4 and CCND3 protein levels after exposure to $IC_{50}$ concentration of COMPOUND I for the times noted. Protein levels quantitated from 3 independent western blots, graphed as fold change over vehicle. Error bars, ±SD. C) Representative western blot of CDK4 and CCND3 protein levels as a function of duration of COMPOUND I exposure (MV4-11 cells 500 nM, KG-1 cells 600 nM, and EOL-1 cells 300 nM). V—vehicle, A—COMPOUND I.

COMPOUND I Induces Cytotoxicity, Upregulates p21, and Induces $G_0$-$G_1$ Cell-Cycle Arrest in AML Cells COMPOUND I inhibited proliferation in AML cell lines and various forms of lymphoma cell lines with $IC_{50}$ values ranging from 57 nmol/L to 1.75 µmol/L (FIG. 8; Table 10). The drug showed only modest variation in potency as a function of duration of exposure in MV4-11 cells with $IC_{50}$ values of 0.47, 0.40, and 0.24 µmol/L for exposures of 48, 72, and 120 hours, respectively. Previous studies reported upregulation of KLF4 and CDKN1A expression as a potential mechanism of APT0-COMPOUND I activity in tumors. Although COMPOUND I upregulates KLF4 expression in 4 of 6 AML cell lines tested (FIG. 15A), CDKN1A (p21) expression was induced in all AML cell lines in a concentration-dependent manner (FIGS. 15B and 15C). The upregulation of CDKN1A mRNA increased with duration of exposure in all AML cell lines tested (FIGS. 15D and 15E). At later time points, CDKN1A expression began to decrease, likely due to increasing cell death. Induction of CDKN1A expression is typically associated with a subsequent $G_0$-$G_1$ cell-cycle arrest, which was observed following COMPOUND I treatment of solid tumor lines. Consistent with this, a dose-dependent increase of cells in $G_0$-$G_1$ was observed with concomitant reduction in the fraction of cells in the S- and $G_2$-M phases for all AML cell lines tested (FIGS. 9A-C, top). In the case of MV4-11, all live cells had arrested in $G_0$-$G_1$ after 24-hour exposure to 1 µmol/L APT0-COMPOUND I. CCND3 (Cyclin D3) and CDK4 are known to promote $G_1$ cell-cycle progression, while CDKNIA serves to negatively regulate this process. Western blot analysis of COMPOUND I-treated AML cells revealed dose-dependent inhibition of both CDK4 and CCND3, albeit to different degrees in each of the 3 AML lines (FIGS. 9A-C, bottom; FIG. 16A).

TABLE 10

COMPOUND I $IC_{50}$ values in leukemia and lymphoma cell lines

| Disease Type | Cell Lines | $IC_{50}$ (µM) Mean |
|---|---|---|
| MCL | Jeko-1 | 0.057 |
| MCL | GRANTA-519 | 0.082 |
| Burkitt's | Raji | 0.1 |
| AML | MOLM-13 | 0.14 |
| MCL | Mino | 0.23 |
| AML | MV4-11 | 0.24 |
| AML | EOL-1 | 0.3 |
| AML | THP1 | 0.34 |
| Burkitt's | Ramos | 0.35 |
| AML | HL-60 | 0.46 |
| AML | SKM-1 | 0.48 |
| AML | KG-1 | 0.51 |
| DLBCL | SUDHL-6 | 0.51 |
| T-ALL | Jurkat | 0.52 |
| AML | Nomo-1 | 1.45 |
| AML | HEL92.1.7 | 1.75 |

To correlate cell-cycle arrest with various pathway perturbations, and to delineate the sequence of mechanistic events, cell-cycle analyses were performed after treating cells with either vehicle or COMPOUND I ($IC_{50}$ concentration) for various times up to 24 hours. There was no perturbation of cell-cycle phase distribution in cells treated with vehicle alone. An increase in the fraction of cells in $G_0$-$G_1$ was detected as early as 2 hours, and this fraction continued to increase in a time-dependent manner throughout the 24-hour period of drug exposure (FIGS. 9D-F). Western blot analysis showed a time-dependent decrease of CDK4 and CCND3 protein levels that paralleled the $G_0$-$G_1$ arrest (FIGS. 16B and 16C). These data establish that COMPOUND I produces a time- and concentration-dependent $G_0$-$G_1$ arrest in AML cells and suggest that this is mediated by established p21 and cyclin-dependent kinase pathways.

Example 10

COMPOUND I Induces Apoptosis in AML Cell Lines

Figure 10:
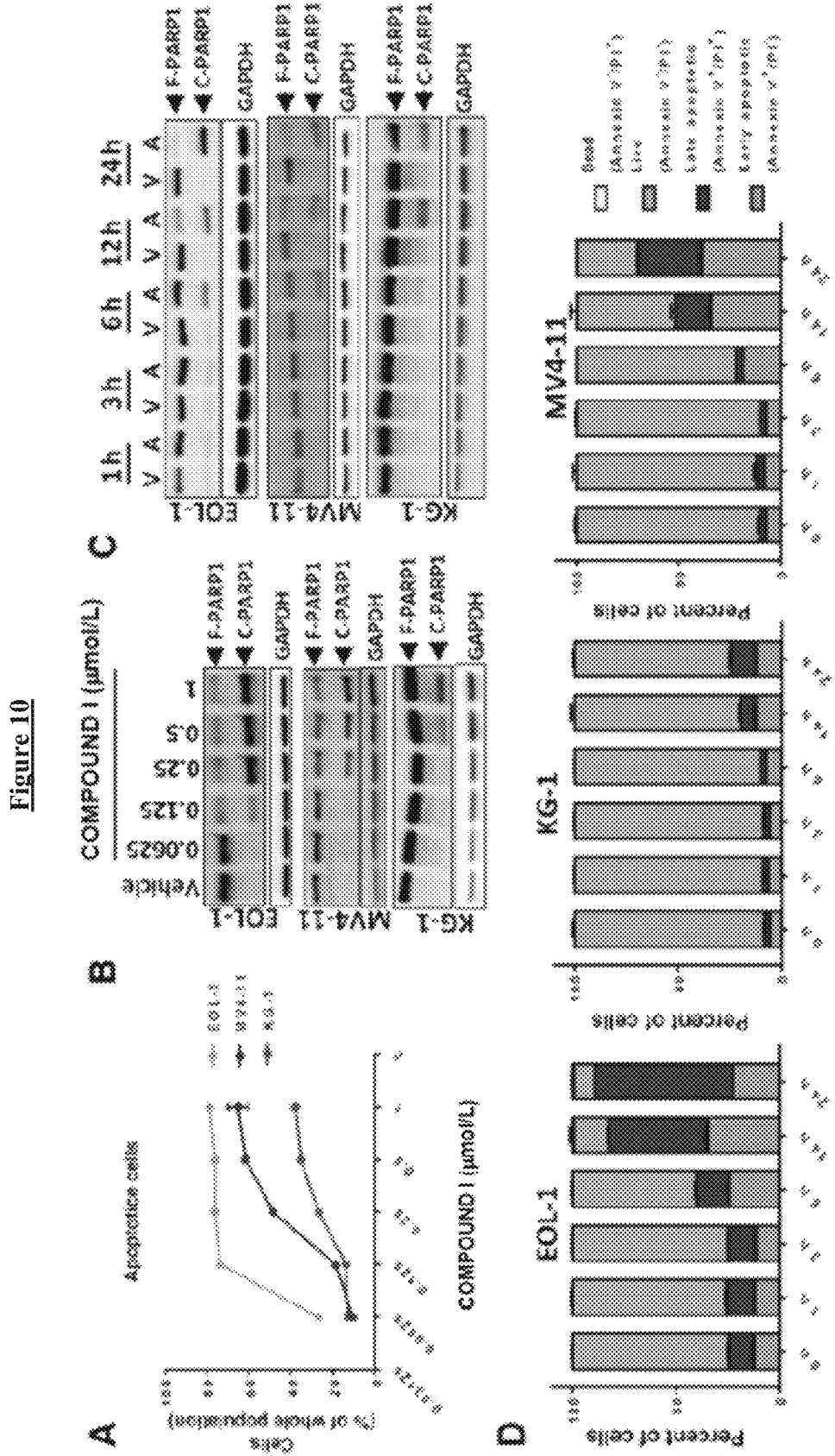
FIG. 10 shows that COMPOUND I treatment induces apoptosis in a time- and concentration-dependent manner. A, Percent apoptotic (early and late) MV4-11, KG-1, and EOL-1 cells after 24-hour exposure to COMPOUND I. Apoptosis was measured as described in the Materials and Methods section. B, Western blot analysis with PARP1-specific antibody of AML cells treated for 24 hours with V-vehicle or A-COMPOUND I. PARP1 antibody recognizes both full-length (upper band) and cleaved PARP1 (lower band). C, Western blot analysis of PARP1 cleavage in MV4-11, KG-1, and EOL-1 cells treated for 1 to 24 hours with 500 nmol/L of COMPOUND I. GAPDH is included as loading control. D, Time course of COMPOUND I induced apoptosis in MV4-11 (500 nmol/L), KG-1 (600 nmol/L), and EOL-1 (300 nmol/L) cells. Error bars, ±SD of two replicate assays.
Figure 17:
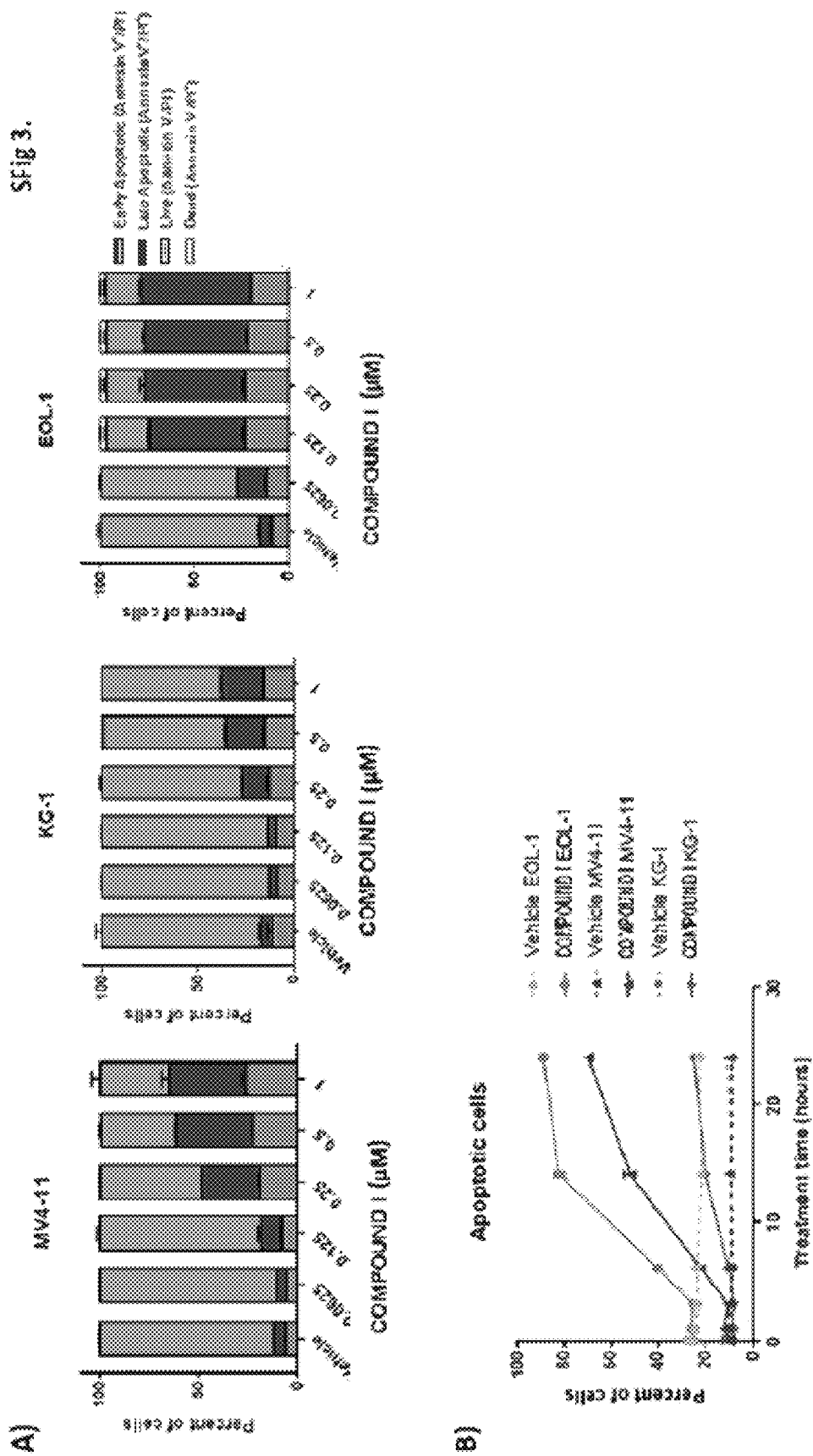
FIG. 17 shows that COMPOUND I treatment induces apoptosis in a time- and concentration-dependent manner A) Histograms showing distribution of early versus late apoptotic cells. B) Total apoptotic cells in COMPOUND I versus vehicle treated MV4-11, KG-1, and EOL-1 cells as a function of time. Error bars, ±SD from 2 replicate experiments.

To investigate the mechanism by which COMPOUND I causes cell death, MV4-11, EOL-1, and KG-1 AML cells were treated with or without COMPOUND I and subjected to apoptotic marker detection by flowcytometry and Western blotting. Cells were stained with PI and Annexin V to distinguish between live (Annexin V and PI negative), early apoptotic (Annexin V positive and PI negative), late apoptotic (Annexin V and PI positive), and dead (Annexin V negative and PI positive) cells. A concentration-dependent increase in apoptotic cells was observed at 24 hours in all cell lines (FIG. 10A; FIG. 17A). The $IC_{50}$ values based on Annexin V and PI staining paralleled antiproliferative $IC_{50}$ values. PARP cleavage (c-PARP1) is a classic signal of apoptosis downstream of both the intrinsic and extrinsic pathways. COMPOUND I induced accumulation of c-PARP1 in a concentration- and time dependent manner that paralleled apoptosis induction as measured by Annexin V/PI staining (FIGS. 10B-C; FIG. 17B). For all 3 AML cell lines, increases in apoptotic cells appeared between 3 and 6 hours after exposure to COMPOUND I (FIG. 10D), which followed $G_0$-$G_1$ cell-cycle arrest observed at 2-hour exposure.

Example 11

COMPOUND I Pharmacodynamics

To gain further insight into the pathways exploited by COMPOUND I to cause cell-cycle arrest and apoptosis, differential expression analysis was performed at both the mRNA and protein levels. MV4-11 cells were treated with either vehicle or 500 nmol/L COMPOUND I for 6 hours, and then gene expression was analyzed by RNA-seq. A total of 1,643 genes were found to be differentially regulated upon COMPOUND I treatment (>2-fold change and P<0.05) with 416 being upregulated and 1,227 being downregulated (Table 11). The RNA-seq analysis detected a 2-fold increase in KLF4 and a 4.5-fold increase in CDKN1A expression, which is validated by the qRT-PCR data with MV4-11 cells. The differentially regulated genes were analyzed for enriched pathways or GO (Gene Ontology) terms (FIG. 18A) utilizing the Broad Molecular Signatures database (http://software.broadinstitute.org/gsea/msigdb/index.jsp). As expected, apoptotic and cell-cycle pathways were enriched in the differentially expressed gene set. Unexpectedly, gene expression profiles after COMPOUND I treatment were also enriched in the DNA damage response (DDR) and endoplasmic reticulum (ER) stress/unfolded protein response pathways. In addition, upregulated genes were enriched in TP53 pathways and genes downregulated by MYC. Gene expression changes detected in MV4-11 cells raised the possibility that COMPOUND I could cause apoptosis by inducing DNA damage and activating cellular stress pathways, and/or by inhibition of expression of the MYC oncogene.

TABLE 11

Differential expression genes from RNA-seq and RPPA

| antibody/protein | fold change | p-value |
| --- | --- | --- |
| Histone-H3 | 5.08312399 | 5.45E−05 |
| H2AX_pS140 | 4.19597407 | 0.000522 |
| PAR | 2.70749443 | 0.001439 |
| Caspase-3 | 2.38247687 | 0.00075 |
| p38_pT180_Y182 | 2.02214932 | 0.000782 |
| DM-Histone-H3 | 2.00835777 | 0.000457 |
| DM-K9-Histone-H3 | 2.00341212 | 0.002556 |
| Caspase-7-cleaved | 1.67071017 | 3.46E−05 |
| Bad_pS112 | 1.55036509 | 0.002505 |
| Hif-1-alpha | 1.4823094 | 0.012889 |
| Syk | 1.43304918 | 0.031588 |
| Chk1 | 1.43276703 | 0.034112 |
| E2F1 | 1.42334521 | 0.021131 |
| N-Ras | 1.39693163 | 0.004314 |
| Ubq-Histone-H2B | 1.37487462 | 0.037092 |

TABLE 11-continued

Differential expression genes from RNA-seq and RPPA

| antibody/protein | fold change | p-value |
| --- | --- | --- |
| XBP-1 | 1.36926109 | 0.011104 |
| Cyclin-E1 | 1.36142448 | 0.0002 |
| Chk2_pT68 | 1.31238742 | 0.000457 |
| ADAR1 | 1.3084933 | 0.007035 |
| ACC_pS79 | 1.3015573 | 0.000181 |
| CD29 | 1.29122101 | 0.032909 |
| BiP-GRP78 | 1.28988582 | 0.008195 |
| p53 | 1.28815199 | 0.035039 |
| Pdcd-1L1 | 1.26162272 | 0.039318 |
| PAI-1 | 1.25745484 | 0.025156 |
| Rb_pS807_S811 | 0.64862926 | 0.005124 |
| S6_pS240_S244 | 0.64668982 | 0.002977 |
| Ets-1 | 0.60342423 | 0.014415 |
| Cyclin-B1 | 0.59444823 | 0.001083 |
| PLK1 | 0.49462682 | 0.009377 |
| NDRG1_pT346 | 0.4566332 | 5.11E−05 |

Figure 18:
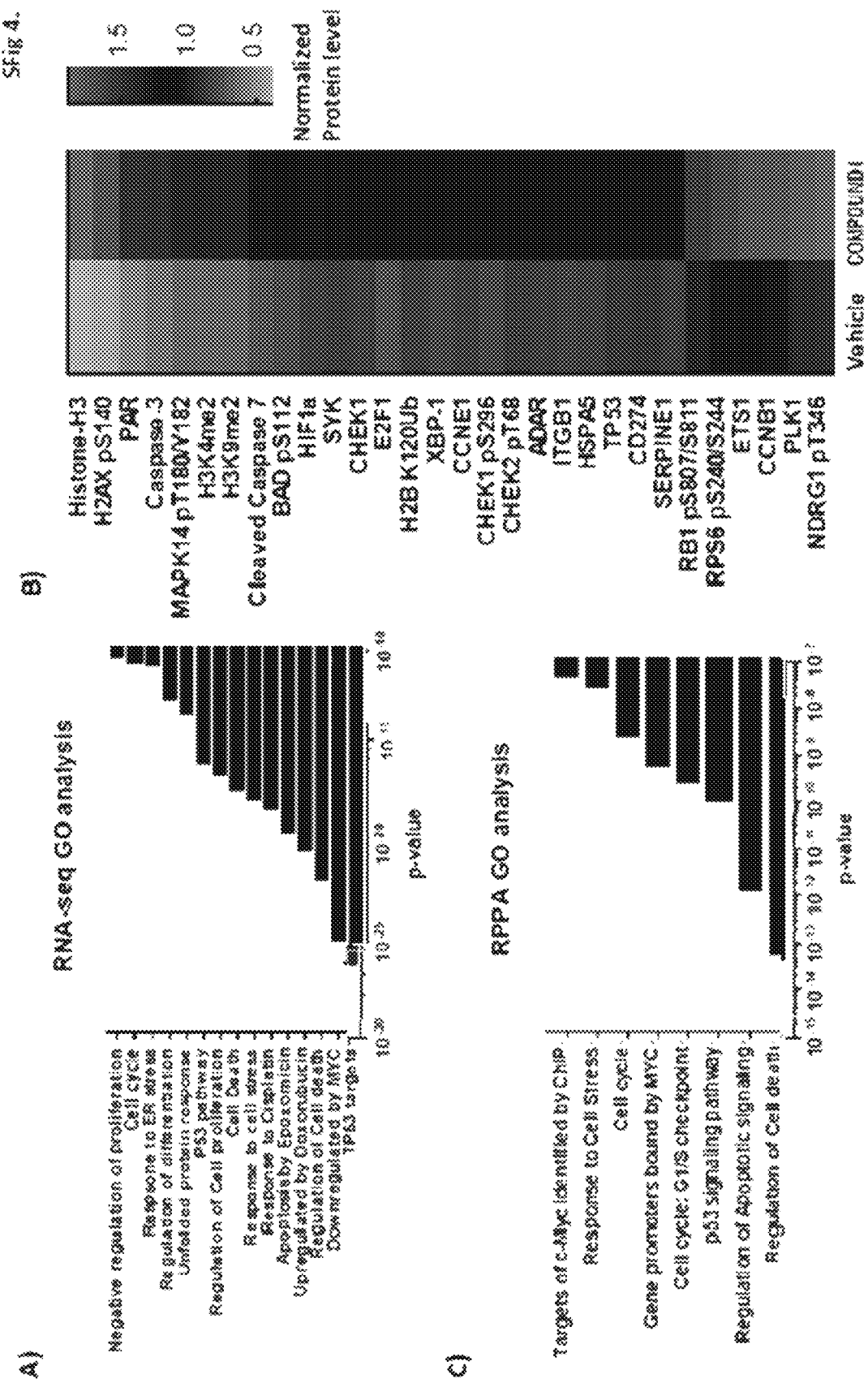
FIG. 18 shows the pathways regulated by COMPOUND I in MV4-11 cells. A) Gene Ontology analysis (GO) of differentially expressed genes detected by RNA-seq analysis of MV4-11 cells treated with vehicle or 500 nM COMPOUND I for 6 h. GO terms and p-values were computed using Broad Molecular Signatures database (MSigDB). B) Normalized protein levels in vehicle and COMPOUND I (500 nM) treated MV4-11 cells after 6 h. Protein levels detected by Reverse Phase Protein Array. Heat-map generated in GraphPad Prism, average of 3 replicate samples. C) GO analysis of differentially expressed proteins utilizing MSigDB.

To examine the effect of COMPOUND I on protein expression, MV4-11 cells were treated as above and analyzed by RPPA microarray to quantify >300 total and post-translationally modified proteins. Effects were observed on levels of both total and post-translationally modified proteins (>1.25-fold and P<0.05) with more proteins unregulated than downregulated (FIG. 18B; Table 11). Of note, there was an increase of cleaved caspase-7, which is indicative of apoptosis. GO analysis of the differentially expressed proteins was performed utilizing the Broad Molecular Signatures database. Significant GO terms included cell death and $G_1$-S cell-cycle arrest pathways, a formal description of $G_0$-$G_1$ arrest, and consistent with the cell-cycle effects detected by flow cytometry and the RNA-seq analyses (FIG. 18C). An increase in E2F1, TP53, γH2AX, CHEK1 phos-S296, and CHEK2 phos-T68 supported the concept that DNA damage pathways are triggered by COMPOUND I treatment. In addition, increases in XBP1, HSPA5, and MAPK14 (p38) phos-T180/182 were observed, indicating ER or cellular stress (P=$1.89E^{-0.8}$; ref 15). DDR pathways can also signal through the MAPK pathway activating MAPK14 and MAPK8 (JNK), and cross-talk between the DDR pathway and ER stress is a well-established phenomenon although it is unclear which pathway represents the initiating event. A significant portion of the differentially expressed proteins and mRNAs are target genes of MYC oncoprotein, which is known to be an integral part of both cell-cycle and apoptotic pathway regulation. Collectively, these data suggested that regulation of the MYC oncogene may play an early and key role in the mechanism of COMPOUND I.

Example 12

COMPOUND I Concentration- and Time Dependently Downregulates MYC mRNA and Protein Levels in AML Cells MYC expression is implicated in the pathogenesis of a wide range of cancers, including leukemia and lymphoma. A recent study demonstrated that inhibition of MYC transcription leads to apoptosis in cancer cells of hematologic origin, making MYC an attractive therapeutic target. A review of our RNA-seq dataset revealed that MYC was downregulated by COMPOUND I in MV4-11 cells at 6 hours. It was also observed that an increased transcription of genes negatively regulated by MYC in COMPOUND I-treated MV4-11 cells.

Figure 11:
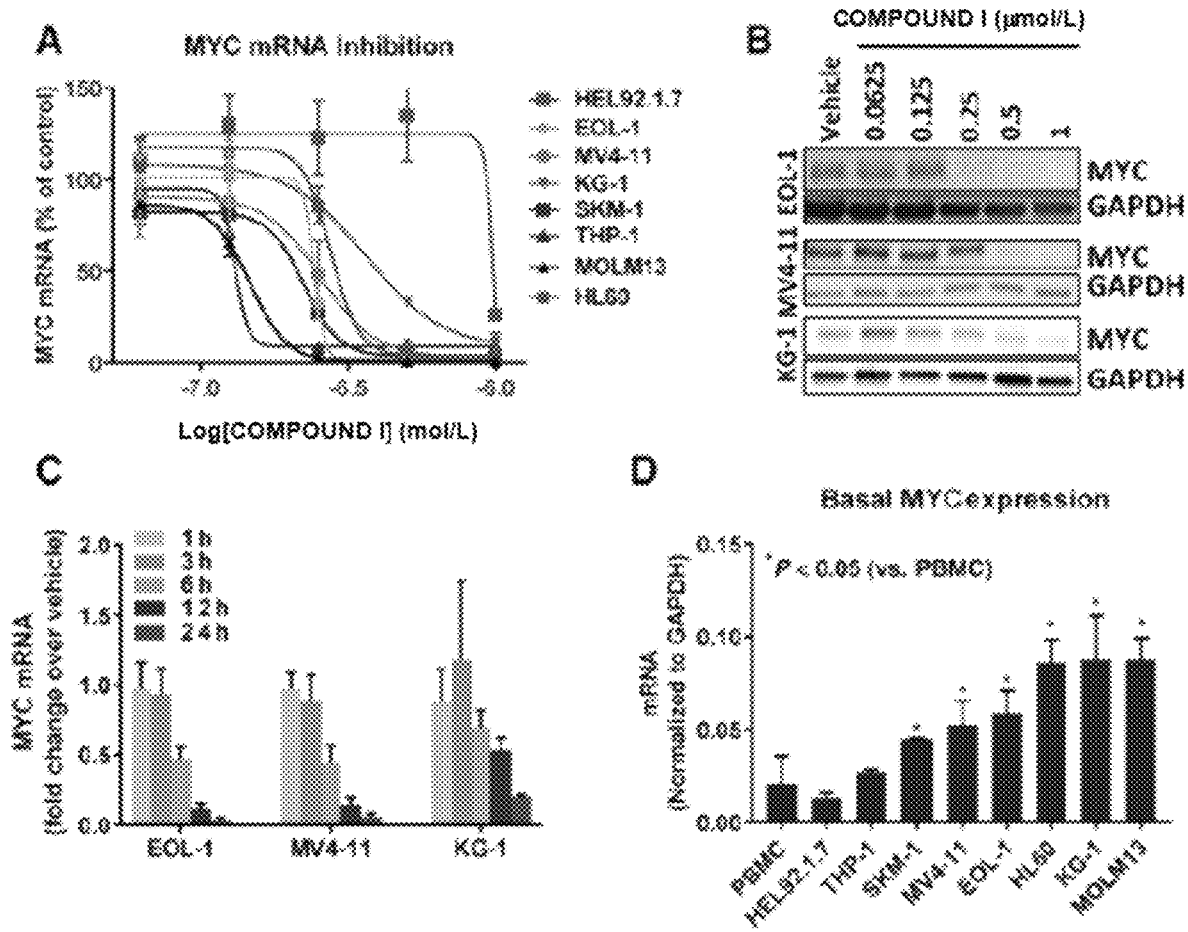
FIG. 11 shows that MYC RNA and protein expression is negatively regulated by COMPOUND I. A, AML lines were treated for 24 hours and MYC mRNA levels measured by qRT-PCR with MYC-specific primer/probe pairs. Graphed as percent of vehicle using GraphPad Prism.b, Western blot analysis of MYC protein level in MV4-11, KG-1, and EOL-1 cells treated for 24 hours at the concentrations listed. GAPDH served as a loading control. C, Histogram plot of MYC mRNA expression graphed as fold change over vehicle in MV4-11, KG-1, and EOL-1 cells treated with 500 nmol/L COMPOUND I for the times listed. D, Basal expression level of MYC mRNA in AML cell lines compared with PBMCs from healthy donors. Expression relative to GAPDH assayed by qRT-PCR. Error bars, ±SD from at least three replicate experiments.
Figure 19:
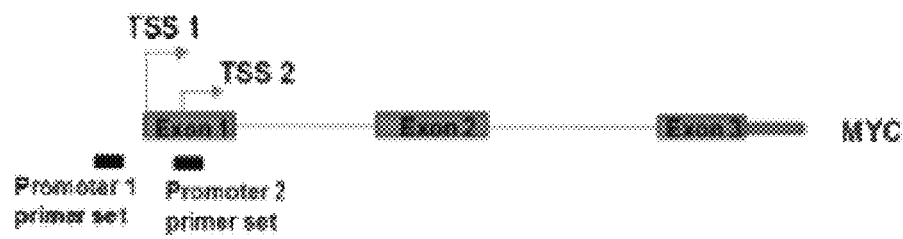
FIG. 19 shows the regulation of MYC expression by COMPOUND I in AML cells. A) Total MYC protein levels in MV4-11, KG-1, and EOL-1 cells treated with 500 nM COMPOUND I for the times noted. Protein levels quantitated from 3 independent western blots, normalized to GAPDH and graphed as fold change over vehicle. Error bars, ±SD. B) Representative western blot quantitated in A). C) Basal protein expression of MYC in AML cell lines versus PBMCs from healthy donors. D) Position of MYC specific primer pairs used in ChIP-qPCR analysis. E) ChIP-qPCR analysis of H3K27ac at MYC promoter in MV4-11 cells treated with 500 nM COMPOUND I for 2, 6, and 24 h graphed as fold change over vehicle treated after normalization to input. F) MYC mRNA level assayed by RT-qPCR in MV4-11 cells pretreated with COMPOUND I (500 nM) or vehicle for 3 h. Samples taken at time points listed after addition of 1 μM actinomycin D. Error bars, ±SD from 3 biological replicates experiments.*P-value<0.05, ** <0.005, calculated by TTEST using excel.
Figure 19:
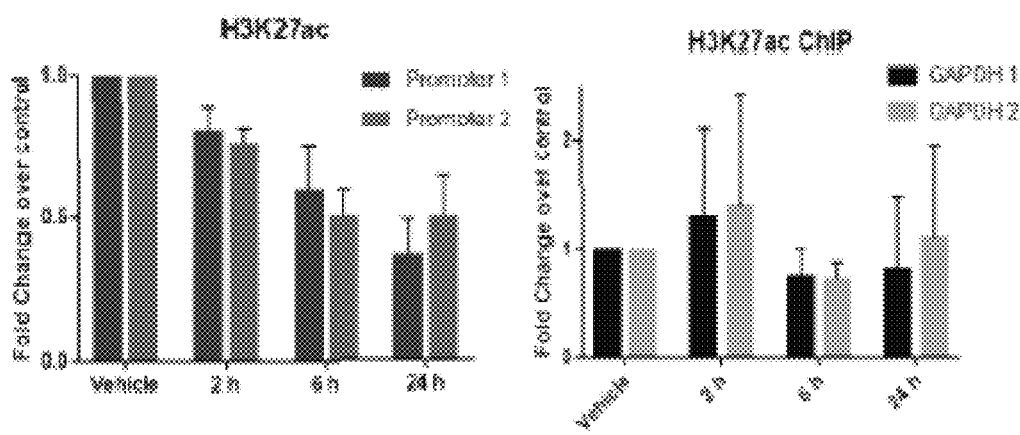
Figure 19:
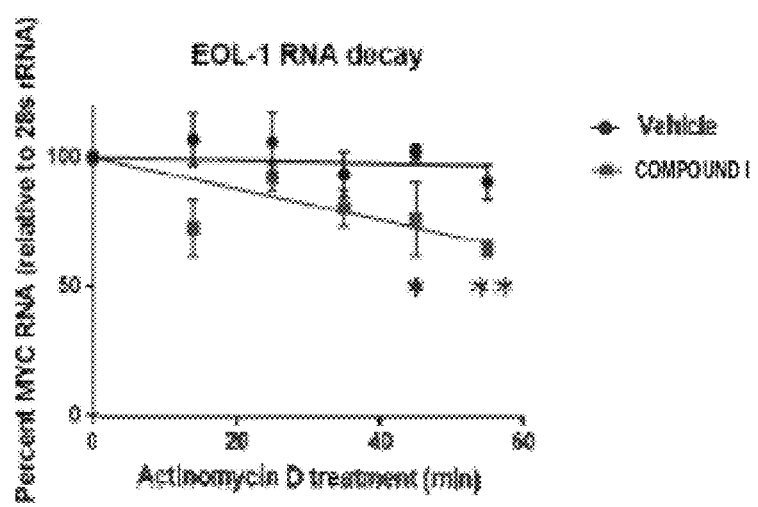

COMPOUND I produced a concentration-dependent decrease in both MYC mRNA and protein levels in all AML cell lines tested, and the $IC_{50}$ values for MYC inhibition paralleled the antiproliferative $IC_{50}$ values (FIGS. 11A and B). These changes increased as a function of exposure time up to 24 hours in the MV4-11, EOL-1, and KG-1 AML cells (FIG. 11C; FIGS. 19A and 19B). The time course of MYC protein repression in MV4-11 cells paralleled inhibition of MYC gene expression levels detected by RNA-seq. All the tested AML cell lines had significantly higher basal expression of MYC as compared with PBMCs from healthy donors (FIG. 11D; FIG. 19C). Thus, COMPOUND I downregulates MYC at the mRNA and protein level in all AML cell lines examined.

Regulation of MYC expression is a complex process that involves MYC transcription, mRNA stability, and protein turnover. ChIP-qPCR analysis for H3K27ac, a well-established marker of active chromatin, was performed to assess transcriptional competency of the MYC gene promoter after treatment with COMPOUND I (FIG. 19D). A decrease in H3K27ac at the MYC promoter in MV4-11 cells was observed as early as 2 hours and progressed over time, indicating that modification of the MYC promoter and subsequent transcriptional repression of the MYC gene is an early mediator of the COMPOUND I mechanism of action (FIG. 19E). To determine whether COMPOUND I affected MYC mRNA stability, an RNA decay assay was performed on EOL-1 cells. There was a clear decrease in MYC mRNA levels in the COMPOUND I pretreated cells versus vehicle (FIG. 19F), indicating that COMPOUND I can decrease the stability of MYC mRNA. These data suggest that COMPOUND I regulates MYC by affecting both transcription and mRNA stability.

Example 13

COMPOUND I Triggers DNA Damage and Cellular Stress Pathways

Figure 12:
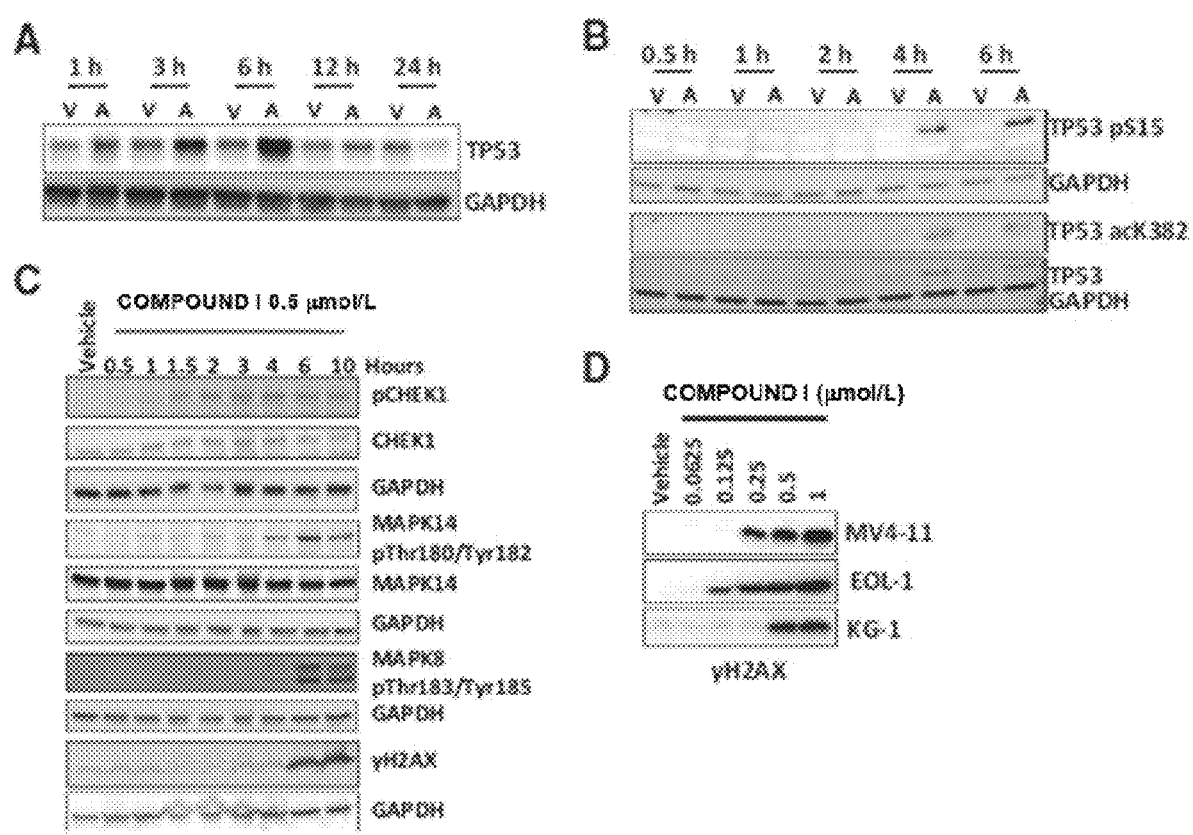
FIG. 12 shows that COMPOUND I induces DDR pathways. A, Total TP53 protein levels in MV4-11 cells treated with (V) vehicle or 500 nmol/L (A) COMPOUND I for increasing periods of time. B, Posttranslational modifications of TP53 detected by Western blot analysis in MV4-11 cells treated as in A. C, Western blot analysis of MV4-11 cells exposed to 500 nmol/L COMPOUND I. D, Western blot analysis of γ-H2AX (H2AX phos-S139) levels in MV4-11, KG-1, and EOL-1 cells treated with COMPOUND I for 24 hours at the concentrations noted.

In addition to MYC, RNA and protein differential expression analyses pointed to the involvement of TP53, DNA damage, and ER stress in the mechanism of action of COMPOUND I. Validation of the RPPA data that had demonstrated an increase in TP53 protein level after COMPOUND I treatment in MV4-11 cells was sought. Exposure of MV4-11 cells to 500 nmol/L COMPOUND I produced a significant increase in TP53 levels at early time points (1, 3, and 6 hours), followed by a return to baseline at 12 hours and a further reduction at 24 hours, presumably due to extensive cell death at this time point (FIG. 12A). The increase in total protein was concomitant with an increase in phospho-Ser15 and acetyl-K382 (FIG. 12B). TP53 is phosphorylated at Ser15 and Ser20 in response to DNA damage, which reduces MDM2 binding and proteasomal degradation of p53. Furthermore, p53 is acetylated in response to cellular stress, and this modification can further stabilize TP53 protein levels and modulate binding activity. Activation of TP53 can trigger apoptosis through upregulation of proapoptotic factors such as BBC3 (PUMA), PMAIP1 (NOXA), and BAX. The RNA-seq dataset showed a 3.95-fold increase in BBC3 and 1.38-fold increase in PMAIP1 in COMPOUND I-treated MV4-11 cells. Involvement of DNA damage and cell stress pathways was further interrogated in MV4-11 cells at early time points after treatment with 500 nmol/L COMPOUND I. An increase in phos-CHEK1 was detected at 1 hour after COMPOUND I addition with a peak at approximately 4 hours, suggesting that DNA damage was an early event (FIG. 12C). Following CHEK1 phosphorylation, there was a robust increase in the DDR marker γH2AX by 6 hours. A concentration-dependent increase in γH2AX was detected in all AML lines tested, thereby adding further credence to the concept that COMPOUND I triggers the DDR pathway (FIG. 12D). In addition, there was an increase in both MAPK14 phos-T180 and MAPK8 phos-Thr183/pTyr185 at 4- to 6-hour treatment, which indicated signaling through the DDR or ER stress pathways (FIG. 12C). Overall, the data suggest that DNA damage induced by COMPOUND I is an early event in the mechanism of COMPOUND I.

Example 14

Intracellular Pharmacokinetics of COMPOUND I

Figure 13:
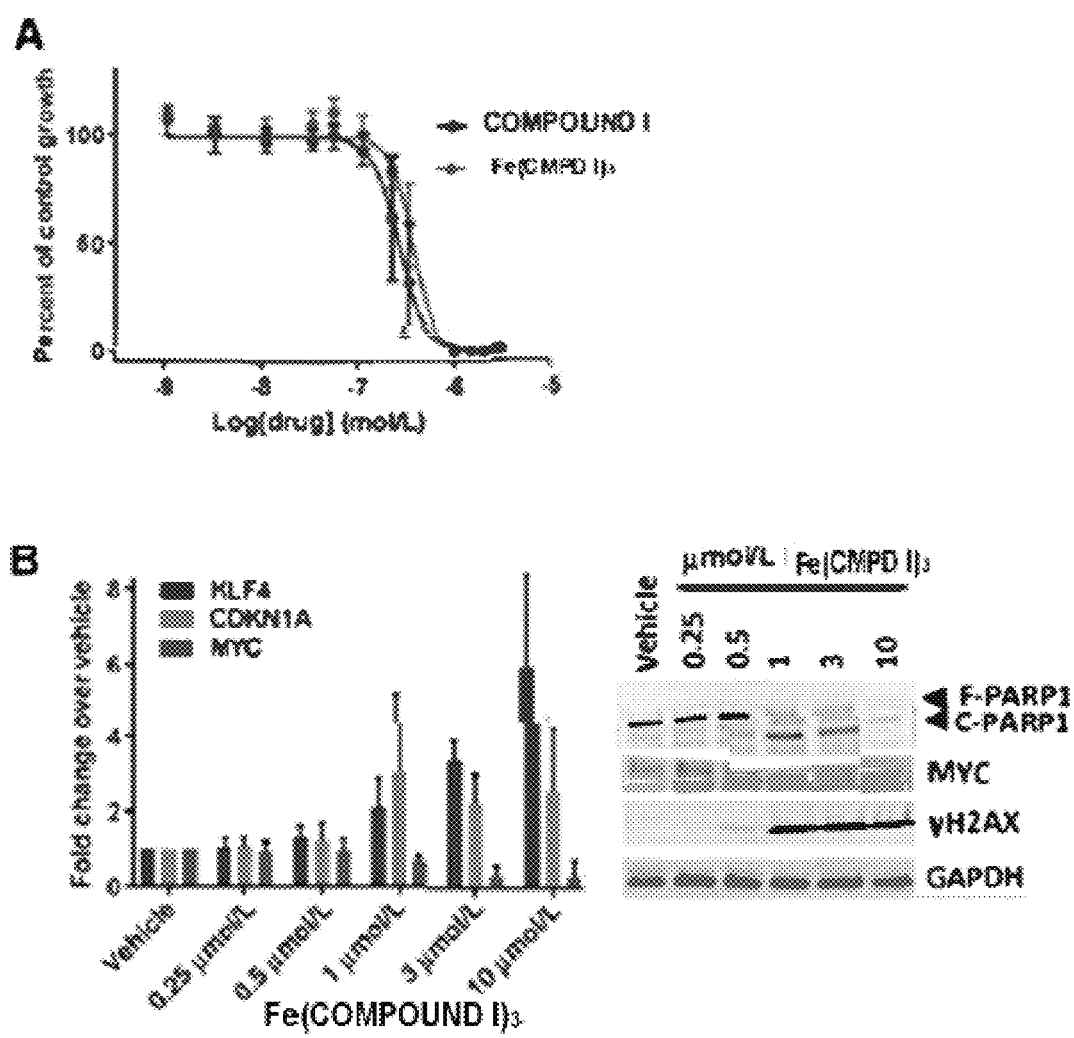
FIG. 13 shows the in vitro and cellular activity of Fe(COMPOUND I)$_3$ complex. A, Concentration-response curves for AML cell lines treated for 5 days with parental COMPOUND I or Fe(COMPOUND I)$_3$. Cell growth expressed as percent of growth of vehicle-treated cells. Error bars, mean SD from 3-5 replicate assays. B, Left, KLF4, CDKN1A, and MYC mRNA expression after 24-hour treatment with Fe(COMPOUND I)$_3$ at concentrations listed. Error bars, mean ±SD. Right, Western blot analysis of c-PARP1, MYC, and γ H2AX protein levels in MV4-11 cells after 24-hour exposure to vehicle (v) or increasing concentrations of Fe(COMPOUND I)$_3$. C, $\Delta T_{1/2}$ values calculated from FRET curves representative examples shown in FIGS. 21 and 22, with at least three replicates for each curve. The $\Delta T_{1/2}$ of each oligo is plotted against log[drug] mol/L for each compound tested.
Figure 13:
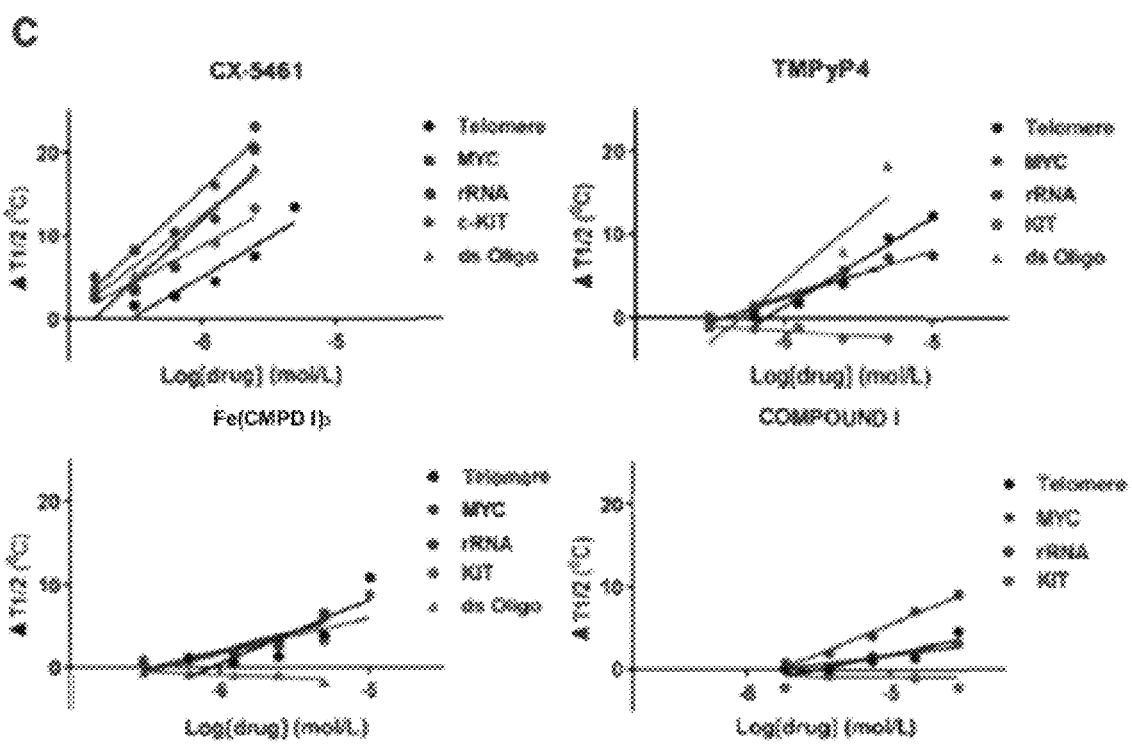
Figure 14:
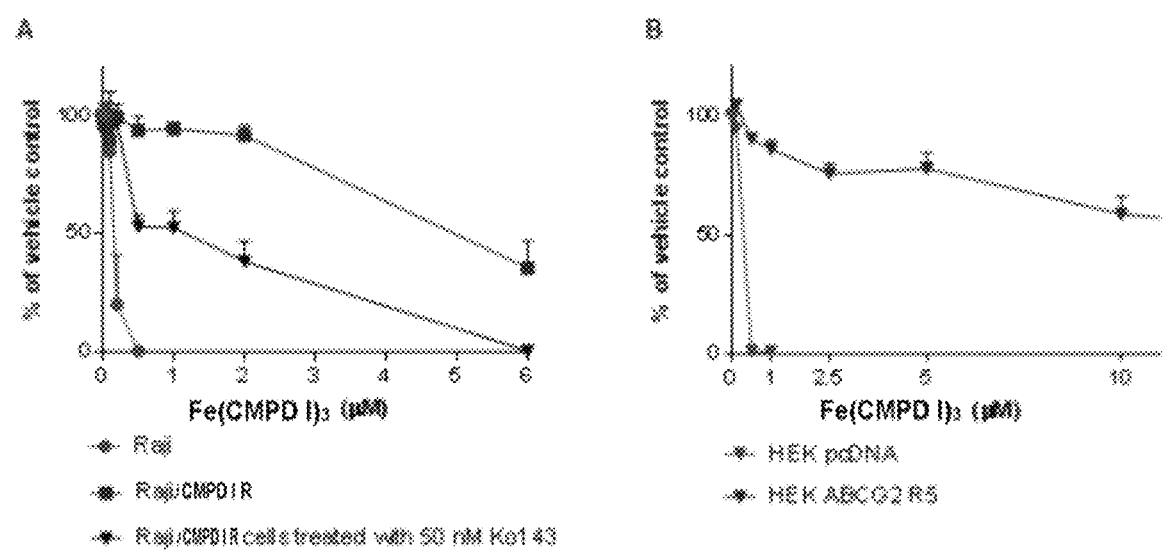
FIG. 14 shows the role of ABCG2 in resistance to Fe(COMPOUND I)$_3$. (A) Concentration-survival cures for Raji (●) and Raji/COMPOUND IR (■) treated with Fe(COMPOUND I)$_3$ alone or in combination with 50 nM Ko143 (▼). (B) Concentration-survival curves for HEK-293 clone R5 transfected with empty vector (●) or a vector expressing ABCG2 (■) treated with Fe(COMPOUND I)$_3$.
Figure 20:
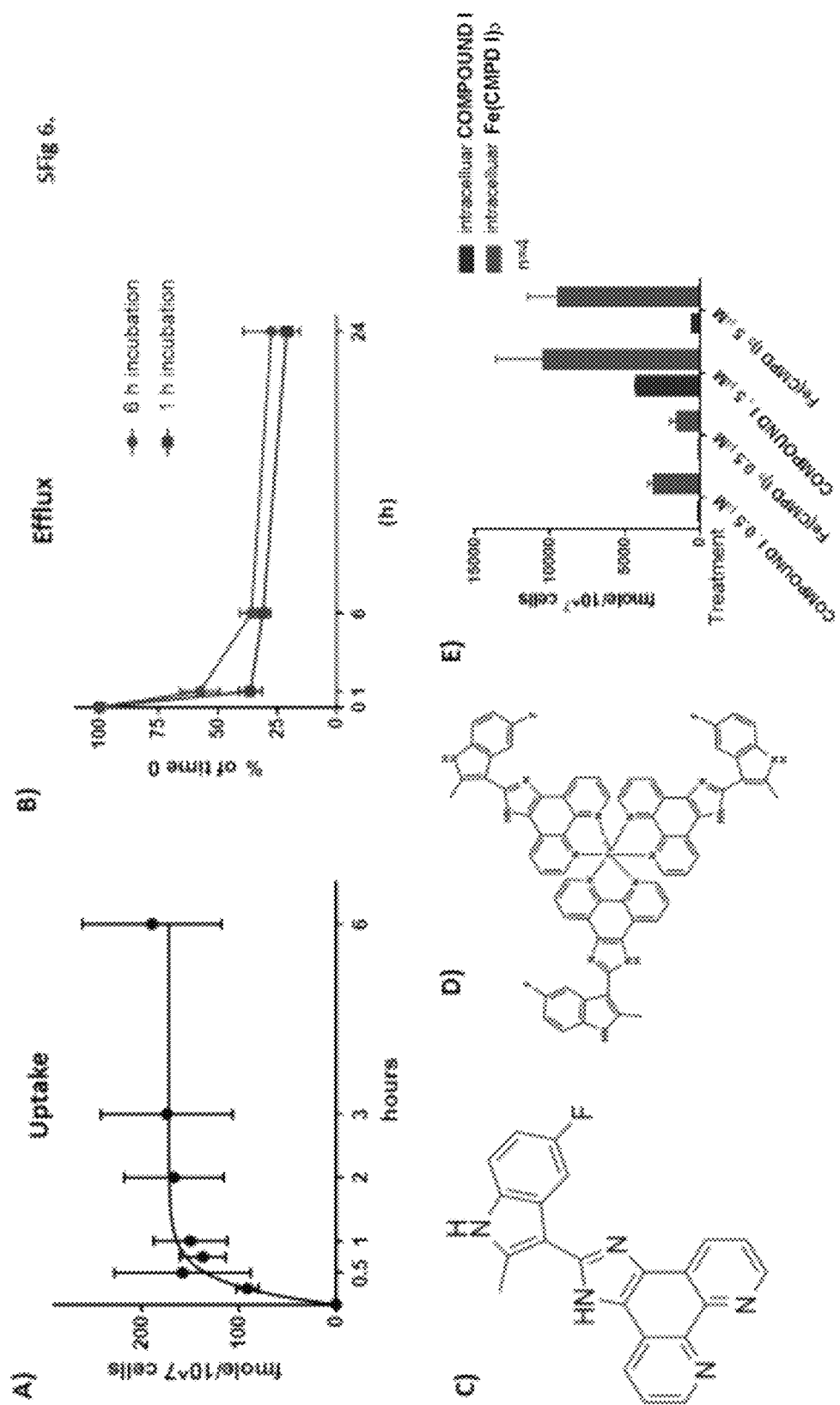
FIG. 20 shows the cellular pharmacology of COMPOUND I. A) Time course of COMPOUND I uptake into KG-1 cells. B) Efflux of COMPOUND I from cells loaded for either 1 or 6 h by exposure of KG-1 cells to 1 μM COMPOUND I. C) Structure of parental monomeric COMPOUND I. D) Structure of Fe(COMPOUND I)$_3$. E) COMPOUND I and Fe(COMPOUND I)$_3$ uptake into MV4-11 cells.

Measurement of the kinetics of uptake and efflux of COMPOUND I in KG-1 AML cells determined by mass spectrometry indicated a gradual approach to steady state and a rapid initial efflux, but a very prolonged terminal efflux (FIGS. 20A and 20B). When KG-1 cells were exposed to COMPOUND I for either 1 or 6 hours and then placed in drug-free media, the efflux pattern consisted of a rapid phase occurring during the first 30 minutes followed by a prolonged terminal phase, such that significant amounts of COMPOUND I were retained in KG-1 cells for longer than 24 hours. Consistent with these data, cellular pharmacokinetic studies disclosed that COMPOUND I is transformed intracellularly to a complex containing 1 atom of Fe and 3 molecules of COMPOUND I [Fe(COMPOUND I)$_3$] (FIGS. 20C and 20D). Indeed, the precomplexed Fe(COMPOUND I)$_3$ drug is as potent as the parental COMPOUND I monomer in cytotoxicity assays (FIG. 13A). Furthermore, Fe(COMPOUND I)$_3$ complex triggered apoptotic and DNA damage pathways, as measured by c-PARP and γH2AX respectively, in MV-4-11 cells. Fe(COMPOUND I)$_3$ also induced KLF4 and CDKN1A expression and inhibited MYC in a dose-dependent manner (FIG. 13B). However, higher concentrations of Fe(COMPOUND I)$_3$ were required to elicit an equal response to parental COMPOUND I in the 24-hour assays (in comparison with 5-day treatment in cytotoxicity assays) likely due to a slower observed influx rate for precomplexed Fe(COMPOUND I)$_3$ (FIG. 20E).

Example 15

COMPOUND I Stabilizes G-Quadruplex Sequences

The parental COMPOUND I and its intracellular Fe(COMPOUND I)$_3$ form contain certain features, such as metal-coordinating phenanthroline rings and planar structures, that may allow the agent to function as a G-quadruplex (G4) DNA ligand. G4 is a dynamic secondary DNA structure caused by guanine-rich regions folding to form planar guanine tetrads, which stack on top of one another. G4-specific sequences are found at telomeres and in the promoters of many important oncogenes. G4 sequences serve as regulators of gene expression and small-molecule ligands that stabilize G4 quadruplexes have been exploited to downregulate important oncogenes, such as KIT and MYC. Stabilization of G4 motifs in telomere DNA can cause inhibition of telomerase, telomere instability, and deprotection, all of which can trigger DDR pathways. Furthermore, origin of DNA replication sites overlap with DNA G4 sequences, and stabilization of G-quadruplex structures at such sites causes stalling of replication forks and cell-cycle arrest.

Figure 21:
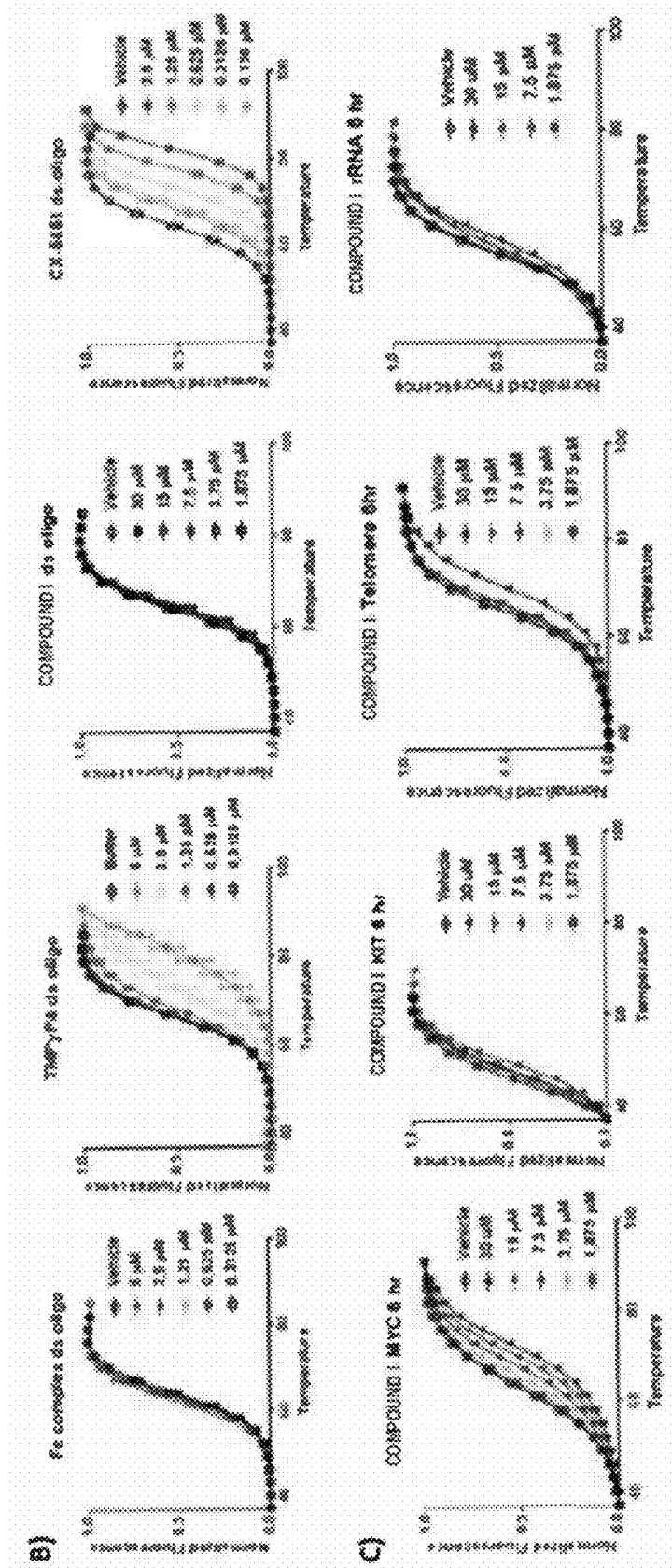
FIG. 21 shows the FRET assay analysis of G-quadruplex structures. A) Schematic of quenching FRET assay. At low temperatures, the G-quadruplex structure forms and the fluorescent FAM signal is quenched by BHQ1; as the temperature is increased the G4 structure unfolds and the FAM signal increases. Temperature at which fluorescent signal is 50% of max ($T_{1/2}$) was calculated for each drug concentration then the $\Delta T_{1/2}$ (drug $T_{1/2}$–Vehicle $T_{1/2}$) was plotted against drug concentration. B) Melting curves of ds-DNA control oligos. C) Melting curves for G4 oligos after 6 hr incubation with COMPOUND I. Error bars, ±SD from 3 biological replicates experiments.
Figure 22:
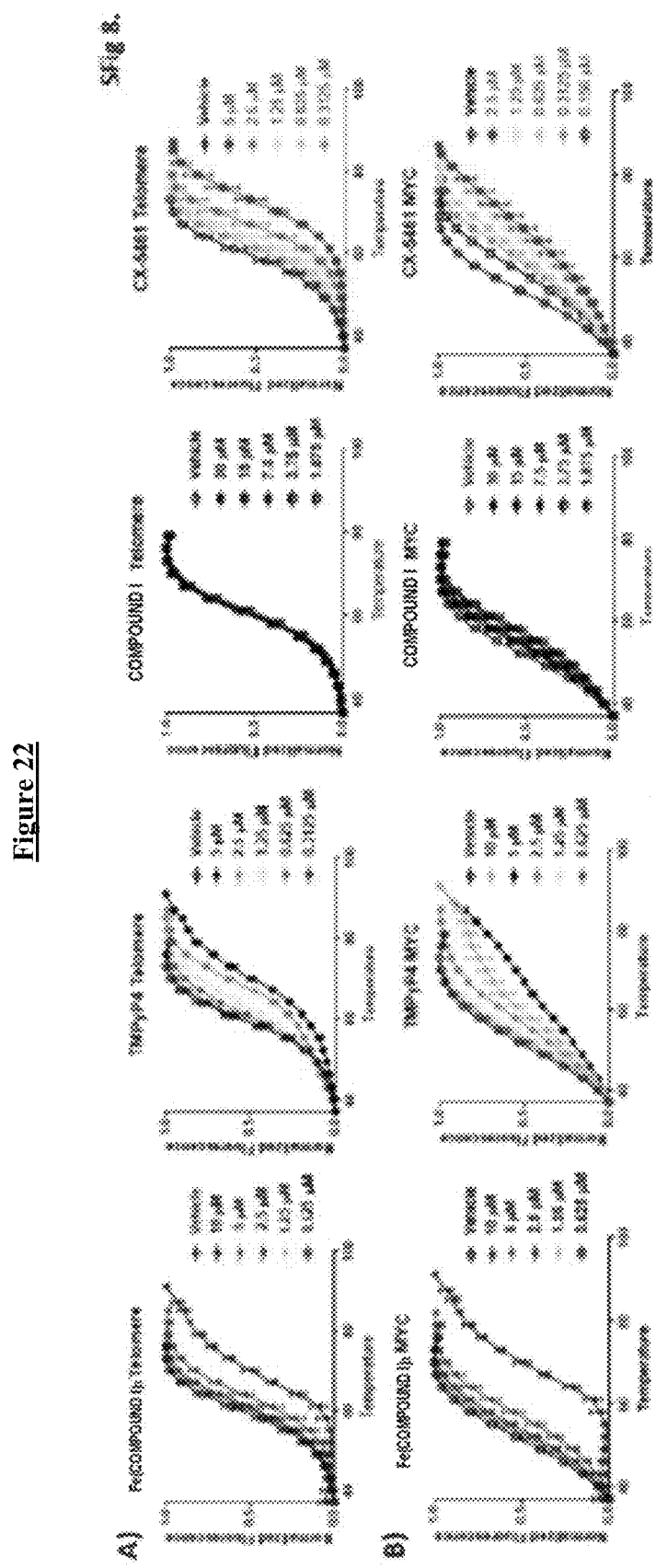
FIG. 22 shows that Fe(COMPOUND I)$_3$ stabilizes Tm of G-quadruplex oligos. A-D) Melting curves of 5' FAM-3' BHQ1 dual labeled oligos containing G-quadruples sequences for A) Human telomeres, B) MYC gene promoter, C) rRNA loci, and D) KIT gene promoter. Error bars, ±SD from 3 biological replicates experiments.
Figure 22:
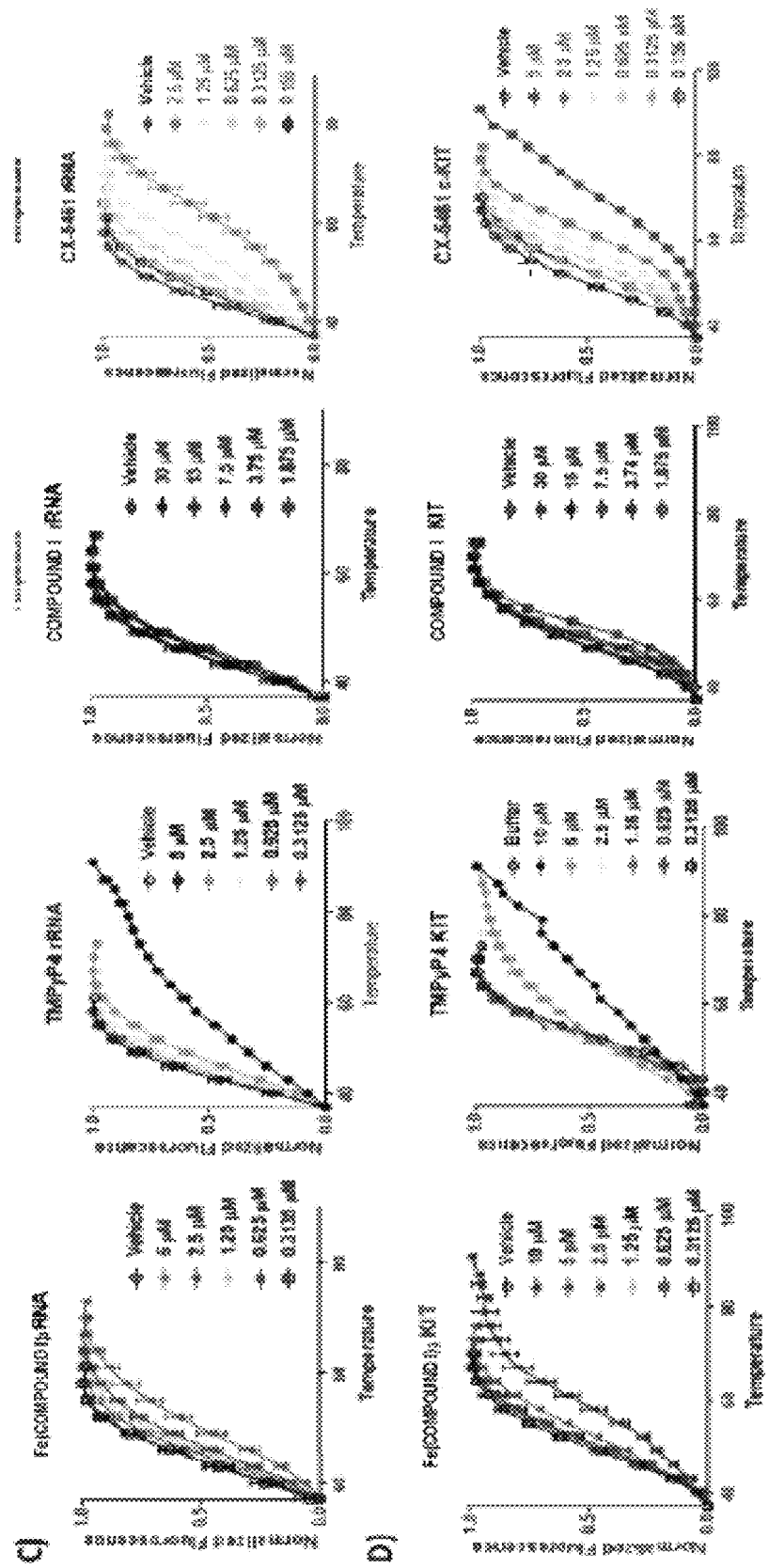

The ability of COMPOUND I (parental monomeric form of the drug) and Fe(COMPOUND I)$_3$ to bind and stabilize G4 sequences using a modified FRET assay was evaluated (FIGS. 21 and 22). TMPyP4, a well-known G4 ligand, and CX-5461, a clinical stage molecule recently reported to have G4-binding properties, were utilized as controls to assess the specificity of COMPOUND I and Fe(COMPOUND I)$_3$ for G4-stabilizing activity. As expected, CX-5461 was a potent stabilizer of all G4 sequences tested, and TMPyP4 stabilized all G4 motifs except the G4 of the KIT gene promoter (FIG. 13C). Interestingly, increasing concentrations of Fe(COMPOUND I)$_3$ stabilized the G4 structures corresponding to the MYC and KIT gene promoters, rRNA, and telomeres with a similar potency to TMPyP4 (FIG. 13C; FIG. 22). Parental monomeric COMPOUND I also showed time-dependent stabilization of G4 motifs, but it demonstrated the greatest propensity for stabilizing the MYC G4 sequences (FIG. 13C).

To assess selectivity for G4 structures over nonspecific interactions with ds-DNA, the FRET assay was repeated with a self-complimentary oligo that forms a ds-DNA hairpin in solution. Notably, Fe(COMPOUND I)$_3$ demonstrated a much higher degree of selectivity for G4 structures over ds-DNA than did both CX-5461 and TMPyP4, highlighting the fact that COMPOUND I is a more discriminating G4 ligand (FIG. 13C; FIG. 21B). Gene expression analyses showed that the expression of MYC and KIT was decreased in AML cells in response to COMPOUND I treatment (RNA-seq data, MV4-11 cells 6-hour treatment), but levels of 45 s rRNA were not. The lack of effect on 45 s rRNA may reflect differences in availability of COMPOUND I and/or Fe(COMPOUND I)$_3$ into the rRNA-rich nucleolar region of the nucleus. Nevertheless, COMPOUND I clearly can stabilize G4 structures, which provides an explanation for the inhibition of the expression of MYC and other genes. Without being bound by any particular theory, it is hypothesized that stabilization of G4 motifs by COMPOUND I results in single- and double-strand breaks at replication forks and telomeres; this G4-binding capacity of COMPOUND I identifies a mechanism by which the drug triggers DDR pathways, cell-cycle arrest, and apoptosis.

Example 16

Discussion

COMPOUND I is currently in clinical development for the treatment of AML because of its efficacy in nonclinical models and the fact that it did not produce myelosuppression in animals or in its initial phase I trial in solid tumor patients. The data reported here provide new insights into the mechanism of action of this novel agent that point the way to more precise clinical application and biomarker development. These studies confirmed that COMPOUND I is a potent inducer of $G_0$-$G_1$ cell-cycle arrest and apoptosis in AML cells. Additional new findings include that COMPOUND I produces time- and concentration-dependent downregulation of MYC through effects on both its promoters and mRNA stability, that in many AML cell lines it induces the master transcription factor and tumor suppressor KLF4, and that it induces DNA damage. In addition, the pre-complexed iron form of COMPOUND I, Fe(COMPOUND I)$_3$, causes comparable cytotoxic cellular effects, including apoptosis, DNA damage, and downregulation of MYC expression.

The discovery that COMPOUND I, whether in its parental monomeric form or the Fe(COMPOUND I)$_3$ iron complex form, stabilizes G4 motifs in DNA provides an explanation for many of the pharmacodynamic effects of this drug. Stabilization of G4s is known to disrupt telomere stability and stall replication forks, resulting in single- and double-strand DNA breaks. Such stabilization of G4 in the MYC promoter is thought to function as a gene silencer. This, coupled with targeting of KIT and telomere G4 structures by COMPOUND I, provides a mechanism through which COMPOUND I activates DDR pathways that coordinate cell-cycle arrest and promote apoptosis in AML cells.

In addition, cells harboring BRCA1/2 mutations are hypersensitive to COMPOUND I, further supporting a role for DNA damage in COMPOUND I mechanism of action. COMPOUND I consistently produced upregulation of CDKN1A, which mediates arrest in $G_0$-$G_1$. In addition, CDKN1A can be induced after DNA double-strand breaks to block cell-cycle progression to allow for sufficient time to repair DNA. In combination with CDKN1A induction, COMPOUND I increased KLF4 gene expression in many AML cell lines, which is known to regulate CDKN1A as part of the $G_1$ cell-cycle checkpoint. KLF4 is also known to be upregulated in response to DNA damage and plays a role in both $G_0$-$G_1$ arrest and apoptosis. The role of KLF4 in COMPOUND I mechanism of action is of interest for future studies. Although the structure of COMPOUND I suggests that it might be able to generate reactive oxygen species, no such species have been detected using either molecular sensors or changes in GSH in MV4-11, EOL1, or KG-1 cells.

Activation of CHEK1/2, stabilization of TP53, and induction of E2F1 also indicate that the early events after COMPOUND I treatment function to signal for cell-cycle arrest and DNA repair. Cell-cycle arrest was detected by 2 hours after COMPOUND I treatment, whereas upregulation of several proapoptotic factors at both the RNA and protein levels was observed by 6 hours. In addition to activating DNA repair processes, pCHEK1/2 and TP53 can also play a role in triggering apoptosis. If DNA repair fails, p53 can activate apoptosis via upregulation of BAX, BAD, BBC3, or PMAIP1. Increased expression of these proapoptotic factors was detected by RNA-seq analysis of COMPOUND I-treated MV4-11 cells. It is known that caspase-dependent cleavage of PARP1 is required for apoptosis to proceed. COMPOUND I produced robust and early PARP1 cleavage, adding further credence to the hypothesis that COMPOUND I functions by triggering DDR pathways. This suggests a level of DNA damage that is catastrophic to the cell and an alteration of transcriptional programs that skew the cell toward apoptosis. MYC dysregulation is a common oncogenic driver in multiple malignancies, which makes it an attractive potential therapeutic target. However, targeting MYC is challenging due to the complexity of MYC regulation and signaling. Recently, repression of MYC expression by BET bromodomain inhibitors has proven effective at triggering apoptosis in leukemia cells. However, bromodomain proteins are present on all active genes, and inhibition of bromodomain proteins can cause severe toxicities and myelosuppression. COMPOUND I produced a decrease in MYC expression at both the RNA and protein levels in all AML cell lines tested, and downregulation of MYC paralleled its cytotoxic potency in different AML cells. Higher MYC levels in AML lines than in PBMCs from healthy donors were detected, which may be linked to the differential effect of COMPOUND I on these types of cells. Recent work demonstrated that coordinated upregulation of TP53 and downregulation of MYC led to efficient clearing of leukemic stem cell populations in CML. COMPOUND I treatment of MV4-11 produced this same effect, which provides an additional rationale for its development. It has been reported that higher MYC expression correlates with a poor clinical outcome in epithelial ovarian cancer and neuroblastoma, suggesting that COMPOUND I may have a beneficial effect against these malignancies. Collectively, this data demonstrate a multifaceted mechanism of action for COMPOUND I, primarily through engagement of G-quadruplex structures, that is uniquely suited to targeting hematopoietic malignancies. Moreover, COMPOUND I represents a first-in-class MYC inhibitor that does not cause myelosuppression, making it particularly appropriate for the management of AML patients with compromised bone marrow function.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

The invention claimed is:

1. A method of reducing or treating cancer in a subject, comprising administering a therapeutically effective amount of Compound I:

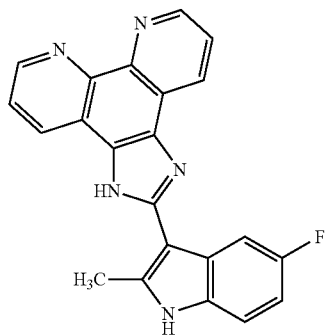 [SMILES: Cc1[nH]c2ccc(F)cc2c1-c1nc2c3cccnc3c3ncccc3c2[nH]1]

I or a pharmaceutically acceptable salt, free base, hydrate, complex, or chelate thereof to the subject; wherein the subject has a mutation in the BRCA-1 or BRCA-2 DNA repair gene, wherein the cancer is breast cancer or ovarian cancer.

2. The method of claim 1, wherein the subject is heterozygous for a mutation in BRCA1 or BRCA2.

3. The method of claim 1, wherein the subject is homozygous for a mutation in BRCA1 or BRCA2.

4. The method of claim 1, wherein the cancer is breast cancer.

5. The method of claim 1, wherein the cancer is a BRCA-associated cancer.

6. The method of claim 1, wherein the subject is human.

7. The method of claim 1, further comprising the administering of a therapeutically effective amount of a second therapeutically active agent.

8. The method of claim 7, wherein the second therapeutically active agent is administered before, during, or after the subject has been administered Compound I.

9. The method of claim 7, wherein the second therapeutically active agent is selected from one or more of the group consisting of immunotherapeutic agents, anticancer agents, and angiogenic agents.

10. The method of claim 9, wherein the second therapeutically active agent is a PARP inhibitor.

11. The method of claim 10, wherein the PARP inhibitor is olaparib.

12. The method of claim 1, wherein the subject experiences less than a 90% decrease in bone marrow activity relative to a subject who was not administered a therapeutically effective amount of Compound I

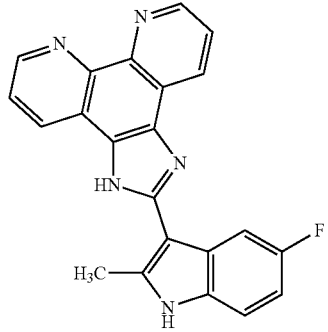

or a pharmaceutically acceptable salt, free base, hydrate, complex, or chelate thereof.

13. The method of claim 12, wherein the subject experiences less than a 10% decrease in bone marrow activity.

14. The method of claim 12, wherein the subject experiences no decrease in bone marrow activity.

15. The method of claim 1, wherein the subject experiences a reduction or decrease in size of a tumor associated with a cancer.

16. The method of claim 15, wherein the subject experiences complete elimination of the tumor associated with cancer.

17. The method of claim 1, wherein the subject experiences an inhibition, decrease, or reduction of neo-vascularization or angiogenesis in a tumor associated with a cancer.

18. A method for killing cancer cells, comprising contacting said cells with a therapeutically effective amount of Compound I

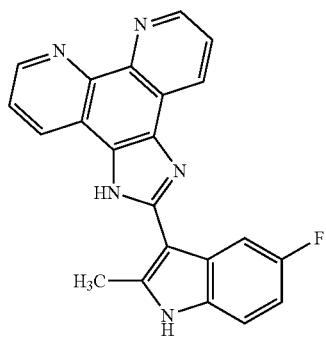 [SMILES: Cc1[nH]c2ccc(F)cc2c1-c1nc2c3cccnc3c3ncccc3c2[nH]1]

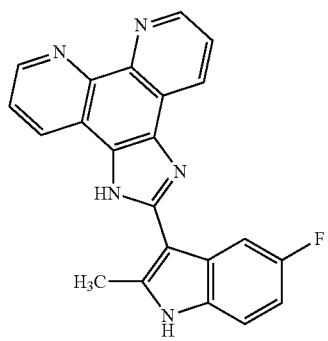 [SMILES: Cc1[nH]c2ccc(F)cc2c1-c1nc2c3cccnc3c3ncccc3c2[nH]1]

or a pharmaceutically acceptable salt, free base, hydrate, complex, or chelate thereof, wherein said cancer cells exhibit one or more mutations in a BRCA-1 or BRCA-2 DNA repair gene wherein the cancer cells are breast cancer cells or ovarian cancer cells.

19. A method for inducing cell cycle arrest in cancer cells, comprising contacting said cells with a therapeutically effective amount of Compound I

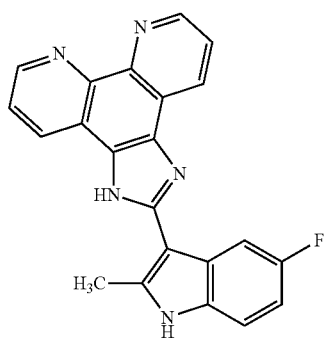 [SMILES: Cc1[nH]c2ccc(F)cc2c1-c1nc2c3cccnc3c3ncccc3c2[nH]1]

or a pharmaceutically acceptable salt, free base, hydrate, complex, or chelate thereof, wherein said cancer cells exhibit one or more mutations in a BRCA-1 or BRCA-2 DNA repair gene, wherein the cancer cells are breast cancer cells or ovarian cancer cells.

20. A method of reducing or treating cancer in a subject, comprising administering a therapeutically effective amount of one or more molecules of in complex with one or more metal atoms, wherein the subject has a mutation in the BRCA-1 or BRCA-2 DNA repair gene, and wherein the cancer is breast cancer or ovarian cancer.

21. The method of claim 20, wherein the one or more metal atoms are selected from the group consisting of iron, zinc, aluminum, magnesium, platinum, silver, gold, chromium, nickel, titanium, copper, scandium, zirconium, vanadium, molybdenum, manganese, tungsten and cobalt.

22. The method of claim 21, wherein the one or more metal atoms are iron.

23. The method of claim 22, wherein the complex has the following structure:

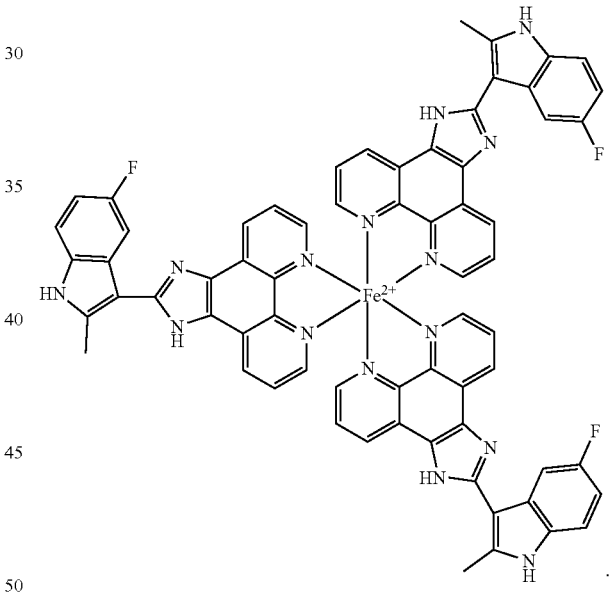

* * * * *